US007105537B2

(12) United States Patent
Gavai et al.

(10) Patent No.: US 7,105,537 B2
(45) Date of Patent: Sep. 12, 2006

(54) 2-SUBSTITUTED CYCLIC AMINES AS CALCIUM SENSING RECEPTOR MODULATORS

(75) Inventors: Ashvinikumar V. Gavai, Princeton Junction, NJ (US); Roy J. Vaz, Branchburg, NJ (US); John K. Dickson, Jr., Apex, NC (US); Jacques Y. Roberge, Princeton, NJ (US); Wu Yang, Princeton, NJ (US); Timur Gungor, Pennington, NJ (US); James R. Corte, Lawrenceville, NJ (US); David P. Rotella, Newtown, PA (US); Yufeng Wang, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 28 days.

(21) Appl. No.: 10/766,086

(22) Filed: Jan. 27, 2004

(65) Prior Publication Data

US 2004/0229860 A1 Nov. 18, 2004

Related U.S. Application Data

(60) Provisional application No. 60/443,255, filed on Jan. 28, 2003.

(51) Int. Cl.
*A61K 31/4439* (2006.01)
*A61K 31/4709* (2006.01)
*C07D 215/18* (2006.01)
*C07D 215/20* (2006.01)
*C07D 401/06* (2006.01)

(52) U.S. Cl. .................. 514/314; 514/343; 546/176; 546/177; 546/276.4

(58) Field of Classification Search .............. None
See application file for complete search history.

(56) References Cited

U.S. PATENT DOCUMENTS

| 4,411,890 | A | 10/1983 | Momany |
| 5,688,938 | A | 11/1997 | Brown et al. |
| 5,763,569 | A | 6/1998 | Brown et al. |
| 6,022,894 | A | 2/2000 | Del Mar et al. |
| 6,031,003 | A | 2/2000 | Nemeth et al. |
| 6,211,244 | B1 | 4/2001 | Van Wagenen et al. |
| 6,436,904 | B1 * | 8/2002 | Ashwell et al. ........... 514/19 |

FOREIGN PATENT DOCUMENTS

| EP | 0342613 B1 | 11/1992 |
| EP | 0449011 B1 | 10/1997 |
| WO | WO 89/07110 | 8/1989 |
| WO | WO 89/07111 | 8/1989 |
| WO | WO 93/04081 | 3/1993 |
| WO | WO 94/18959 | 9/1994 |
| WO | WO 97/37967 | 10/1997 |
| WO | WO 98/45255 | 10/1998 |
| WO | WO 99/51241 | 10/1999 |
| WO | WO 99/51569 | 10/1999 |
| WO | WO 00/45816 | 8/2000 |

OTHER PUBLICATIONS

Delmas, P. and Meunier, P., "The Management of Paget's Disease of Bone," N. Engl. J. Med., vol. 336(8), pp. 558-566 (Feb. 20, 1997) at p. 560, col. 2, lines 24-28; p. 561, Table 1; and p. 563, col. 1, lines 10-22.*

Ashwell et al., STN International (2006) HCAPLUS Database, Columbus, OH, Accession No.: 2000:513717.*

Brown, E.M. et al., "Cloning and characterization of an extracellular $Ca^{2+}$-sensing receptor from bovine parathyroid", Nature, vol. 366, pp. 575-580 (1993).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Edwards, J.P. et al., "Nonsteroidal Androgen Receptor Agonists Based on 4-(trifluoromethyl)-2H-pyrano[3,2-g]quinolin-2-one", Bioorganic & Medicinal Chemistry Letters, vol. 9, pp. 1003-1008 (1999).

Gowen, M. et al., "Antagonizing the parathyroid calcium receptor stimulates parathyroid hormone secretion and bone formation in osteopenic rats", The Journal of Clinical Investigation, vol. 105, No. 11, pp. 1595-1604 (2000).

Greene, T.W. et al., Protective Groups in Organic Synthesis, Third Edition, John Wiley & Sons, Inc., publ., pp. xi-xii (table of contents) (1999).

Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, No. 2, pp. 210-212 (1999).

(Continued)

*Primary Examiner*—Kamal A. Saeed
*Assistant Examiner*—Andrew B. Freistein
(74) *Attorney, Agent, or Firm*—Burton Rodney

(57) ABSTRACT

The present invention relates to modulators of the calcium sensing receptor having the formula I

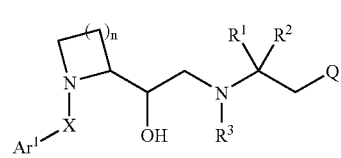

wherein
$Ar^1$, X, n, $R^1$, $R^2$, $R^3$ and Q are as defined herein.

7 Claims, No Drawings

OTHER PUBLICATIONS

Hudlicky, M., Oxidations in Organic Chemistry: ACS Monograph 186, American Chemical Society, publ., pp. ix-xiii (table of contents) (1990).

Larock, R.C., Comprehensive Organic Transformations: A Guide to Functional Group Preparations, VCH Publishers, Inc., publ., pp. xiii-xxviii (table of contents) (1989).

Neer, R.M. et al., "Effect of Parathyroid Hormone (1-34) on Fractures and Bone Mineral Density in Postmenopausal Women with Osteoporosis", The New England Journal of Medicine, vol. 344, No. 19, pp. 1434-1441 (2001).

Wermuth, C.G. et al., Chapter 31:, "Designing Prodrugs and Bioprecursors I: Carrier Prodrugs", The Practice of Medicinal Chemistry, Academic Press, publ., Wermuth, C.G., ed., pp. 671-696 (1996).

Whitfield, J.F. et al., "Parathyroid Hormone, Its Fragments and Their Analogs for the Treatment of Osteoporosis", Treat. Endocrinal., vol. 1, No. 3, pp. 175-190 (2002).

Zaragoza, F. et al., "(Cyanomethyl)trialkylphosphonium Iodides: Efficient Reagents for the Intermolecular Alkylation of Amines with Alcohols in Solution and on Solid Phase", J. Org. Chem., vol. 66, No. 7, pp. 2518-2521 (2001).

Betts, M.J. et al., " ' Hidden' axial chirality as a stereodirecting element in reactions involving enol(ate) intermediates. Part 2. Cyclisation reactions of methyl (4R)-3-(2-diazo-3-oxobutanoyl)-1,1-dioxo-$1\lambda^6$,3-(and 1-oxo-$1\lambda^4$,3-) thiazolidine-4-carboxylates", J. Chem. Soc., Perkin Trans. 1, pp. 1067-1072 (1999).

Florvall, L. et al., "Selective Monoamine Oxidase Inhibitors. 3. Cyclic Compounds Related to 4-Aminophenethylamine. Preparation and Neuron-Selective Action of Some 5-(2-Aminoethyl)-2,3-dihydroindoles", J. Med. Chem., vol. 29, No. 8, pp. 1406-1412 (1986).

Greenstein, J.P. et al., Chemistry of the Amino Acids, vol. 3, Robert E. Krieger Publishing Company, Inc., publ., pp. v-xiii (table of contents) (1984.

Lee, D.G., Chapter 11: "Phase Transfer Assisted Permanganate Oxidations", Oxidation in Organic Chemistry, Part D, Academic Press, publ., Trahanovsky, W.S., ed., pp. 147-204 (1982).

Moed, H.D. et al., "Synthesis of β-phenyl-ethylamine Derivaties. III) Bronchodilators", Recl. Trav. Chim. Pays-Bas, vol. 74; pp. 919-936 (1955).

Nichols, D.E. et al., "Effects of Certain Hallucinogenic Amphetamine Analogues on the Release of [$^3$H]Serotonin from Rat Brain Synaptosomes", J. Med. Chem., vol. 25, No. 5, pp. 530-535 (1982).

Norris, R.K. et al., "Kinetics and Stereochemistry of Elimination of Nitrous Acid from 1-p-Nitrophenyl-2-nitroethyl Derivatives", Aust. J. Chem., vol. 39, pp. 281-294 (1986).

Stewart, R., Chapter 1: "Oxidation by Permanganate", Oxidation in Organic Chemistry, Part A, Academic Press, publ., Wiberg, K.B., ed., pp. 1-68 (1965).

Heindl et al., Enantiospecific synthesis and receptor binding of novel dopamine receptor ligands employing natural 4-hydroxyproline as a practical and flexible building block, Tetrahedron: Asymmetry, Oct. 17, 2003, vol. 14, pp. 3153-3172.

* cited by examiner

2-SUBSTITUTED CYCLIC AMINES AS CALCIUM SENSING RECEPTOR MODULATORS

CROSS-REFERENCE TO RELATED APPLICATION

This application claims the benefit of U.S. Provisional Application No. 60/443,255 filed Jan. 28, 2003, incorporated herein by reference in its entirety.

FIELD OF THE INVENTION

The present invention relates to novel 2-substituted cyclic amines, pharmaceutical compositions containing these compounds and their use as modulators of the calcium sensing receptor.

BACKGROUND OF THE INVENTION

Certain cells in the body respond not only to chemical signals, but also to ions such as extracellular calcium ions ($Ca^{2+}$). Changes in the concentration of extracellular $Ca^{2+}$ (referred to herein as "$[Ca^{2+}]$") alter the functional responses of these cells. One such specialized cell is the parathyroid cell which secretes parathyroid hormone (PTH). PTH is the principal endocrine factor regulating $Ca^{2+}$ homeostasis in the blood and extracellular fluids.

PTH, by acting on bone and kidney cells, increases the level of $Ca^{2+}$ in the blood. This increase in $[Ca^{2+}]$ then acts as a negative feedback signal, depressing PTH secretion. The reciprocal relationship between $[Ca^{2+}]$ and PTH secretion forms the essential mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in $[Ca^{2+}]$ has been confirmed. See Brown et al., Nature 366:574, 1993. In parathyroid cells, this protein, the calcium sensing receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, as reviewed in Nemeth et al., Cell Calcium 11:319, 190. Specifically the osteoclast in bone, the juxtaglomerular, proximal tubule cells in the kidney, the keratinocyte in the epidermis, the parafollicular cell in the thyroid, intestinal cells, and the trophoblast in the placenta, have the capacity to sense changes in $[Ca^{2+}]$. It has been suggested that cell surface calcium sensing receptors may also be present on these cells, imparting to them the ability to detect and to initiate or enable a response to changes in $[Ca^{2+}]$.

Accordingly, compounds which mimic the effects of extracellular $Ca^{2+}$ on a calcium sensing receptor molecule may be useful as calcium modulators which are active at $Ca^{2+}$ receptors. Such compounds could be useful in the treatment of various disease states characterized by abnormal levels of one or more components, e.g., polypeptides, such as hormones, enzymes or growth factors, the expression and/or secretion of which is regulated or affected by activity at one or more $Ca^{2+}$ receptors. Target diseases or disorders for these compounds include diseases involving abnormal bone and mineral homeostasis.

Abnormal calcium homeostasis may be characterized by one or more of the following activities: abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels, such as PTH and calcitonin; and an abnormal change in the response elicited by messengers which affect serum calcium levels.

In extensive animal experiments and in clinical trials, intermittent injection of low doses of PTH has been shown to be a safe and effective stimulator of bone formation (see Whitfiled J F, et al. (2002) Treat Endocrinol (2002) 1(3): 175–190). A double blind, randomized, placebo-controlled trial in postmenopausal women, the PTH peptide fragment (1–34) was shown to reduce the risk of spine fractures and non-traumatic, non-spine fractures 65% and 54%, respectively (Neer R M, et al. (2001) N Engl J Med 344:1434–1441.). In contrast to the anabolic effects observed after intermittent administration, it is well documented that continuous exposure to the hormone results in increases in bone turnover with a subsequent loss in bone mass.

Other than applying a PTH peptide fragment, conceivably, one could make use of the endogenous stores of PTH in the parathyroid gland, in order to stimulate bone formation through the release of PTH.

Proof-of-principle for the calcilytic approach includes a study in osteopenic ovariectomized (OVX) rats in which oral administration of a calcilytic agent NPS-2143 (Gowen M, et al. (2000) J. Clin. Invest. 105:1595–1604) resulted in an increase in bone mas in the presence of an anti-resorptive agent. Intravenous bolus injection of NPS-2143 resulted in a transient increase in serum PTH compatible with the anabolic profile of the hormone. These results indicate that calcilytic agents can serve as a novel class of anabolic agents for the treatment of established osteoporosis.

Thus, the identification of compounds which demonstrate activity as calcium sensing receptor modulators, preferably calcium sensing receptor antagonists, would be of significant value for the treatment of diseases or disorders associated with abnormal bone or mineral homeostasis.

SUMMARY OF THE INVENTION

In accordance with the present invention, compounds are provided that are capable of modulating the function of a calcium sensing receptor, preferably the compounds are antagonists of the calcium sensing receptor, and have the general formula I

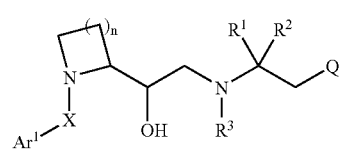

wherein:
    $Ar^1$ is a substituted or unsubstituted aryl or substituted or unsubstituted heteroaryl;

X is a linking group selected from the group consisting of alkylene, CO, alkyleneCO, OCO, alkyleneOCO, $SO_2$ and alkyleneSO$_2$;

n is an integer from 1 to 4;

$R^1$ and $R^2$ are each independently substituted or unsubstituted $C_1$–$C_4$ alkyl, or $R^1$ can be cyclized with $R^2$ to form (—$CH_2$—)$_m$ where m is an integer from 2 to 5;

$R^3$ is hydrogen(H) or alkyl;

Q is $Ar^1$ or G;

G is

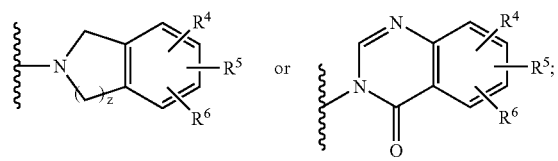

z is 1 or 2; and $R^4$, $R^5$ and $R^6$ are each independently selected from the group consisting of hydrogen, halo, haloalkyl, alkyl, alkoxy, haloalkoxy, hydroxy, cyano, nitro, amino, alkylamino and alkylthio;

including all prodrug esters, pharmaceutically acceptable salts or stereoisomers thereof.

The definition of formula I above includes all pharmaceutically acceptable salts, stereoisomers and prodrug esters of formula I.

The compounds of formula I function as modulators of the calcium sensing receptor. Preferably, the compounds of formula I exhibit activity as antagonists of the calcium sensing receptor and may be used in the treatment of diseases or disorders associated with calcium sensing receptor activity, such as abnormal bone and mineral homeostasis, particularly, hypoparathyroidism, osteosarcoma, chondrosarcoma, periodontal disease, fracture healing, osteoarthritis, Paget's disease, osteopenia, glucocorticoid induced osteoporosis, osteomalacia, osteoporosis, metastatic bone disease or joint replacement.

The present invention provides for compounds of formula I, pharmaceutical compositions employing such compounds and for methods of using such compounds. In particular, the present invention provides for a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with calcium sensing receptor activity, such as the diseases or disorders defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another type of therapeutic agent, is administered, concurrently or sequentially, to a human patient in need of treatment.

DETAILED DESCRIPTION OF THE INVENTION

[1] Thus, in a first embodiment, the present invention provides for compound of the formula I

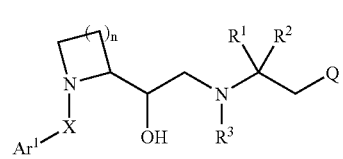

wherein:

$Ar^1$ is a substituted or unsubstituted aryl or substituted or unsubstituted heteroaryl;

X is a linking group selected from the group consisting of alkylene, CO, alkyleneCO, OCO, alkyleneOCO, $SO_2$ and alkyleneSO$_2$;

n is an integer from 1 to 4;

$R^1$ and $R^2$ are each independently substituted or unsubstituted $C_1$–$C_4$ alkyl, or $R^1$ can be cyclized with $R^2$ to form (—$CH_2$—)$_m$ where m is an integer from 2 to 5;

$R^3$ is hydrogen(H) or alkyl;

Q is $Ar^1$ or G;

G is

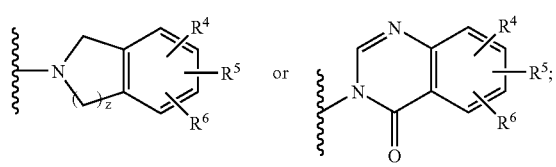

z is 1 or 2; and $R^4$, $R^5$ and $R^6$ are each independently selected from the group consisting of hydrogen, halo, haloalkyl, alkyl, alkoxy, haloalkoxy, hydroxy, cyano, nitro, amino, alkylamino and alkylthio;

including all prodrug esters, pharmaceutically acceptable salts or stereoisomers thereof.

[2] In a preferred embodiment, the present invention provides a compound of formula I wherein:

X is alkylene n is an integer from 1 to 3;

$R^3$ is hydrogen(H) or methyl; and

Q is selected from $Ar^1$, substituted or unsubstituted phenyl, substituted or unsubstituted napthyl or substituted or unsubstituted benzothiophene;

including all prodrug esters, pharmaceutically acceptable salts or stereoisomers thereof.

[3] In another preferred embodiment, the present invention provides the compound of formula I wherein:

X is alkylene;

n is 2;

$R^1$ and $R^2$ are methyl, or $R^1$ can be cyclized with $R^2$ to form a cyclopropyl ring;

$R^3$ is hydrogen; and

Q is substituted or unsubstituted phenyl or substituted or unsubstituted napthyl.

[4] In another preferred embodiment, the present invention provides compound of formula I wherein:
X is alkylene;
n is 2;
$R^1$ and $R^2$ are methyl, or $R^1$ can be cyclized with $R^2$ to form a cyclopropyl ring;
$R^3$ is hydrogen;
Q is G where G is

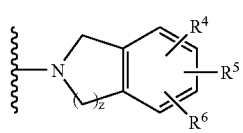

z is 2; and
$R^4$, $R^5$ and $R^6$ are H.

[5] In a more preferred embodiment, the present invention provides compound of formula I wherein the compound is selected from:

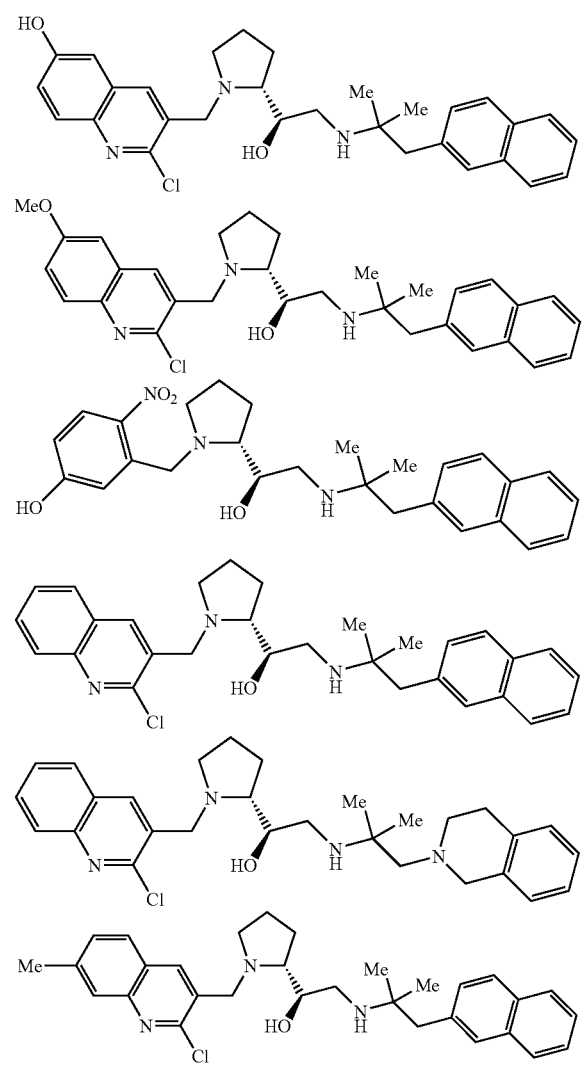

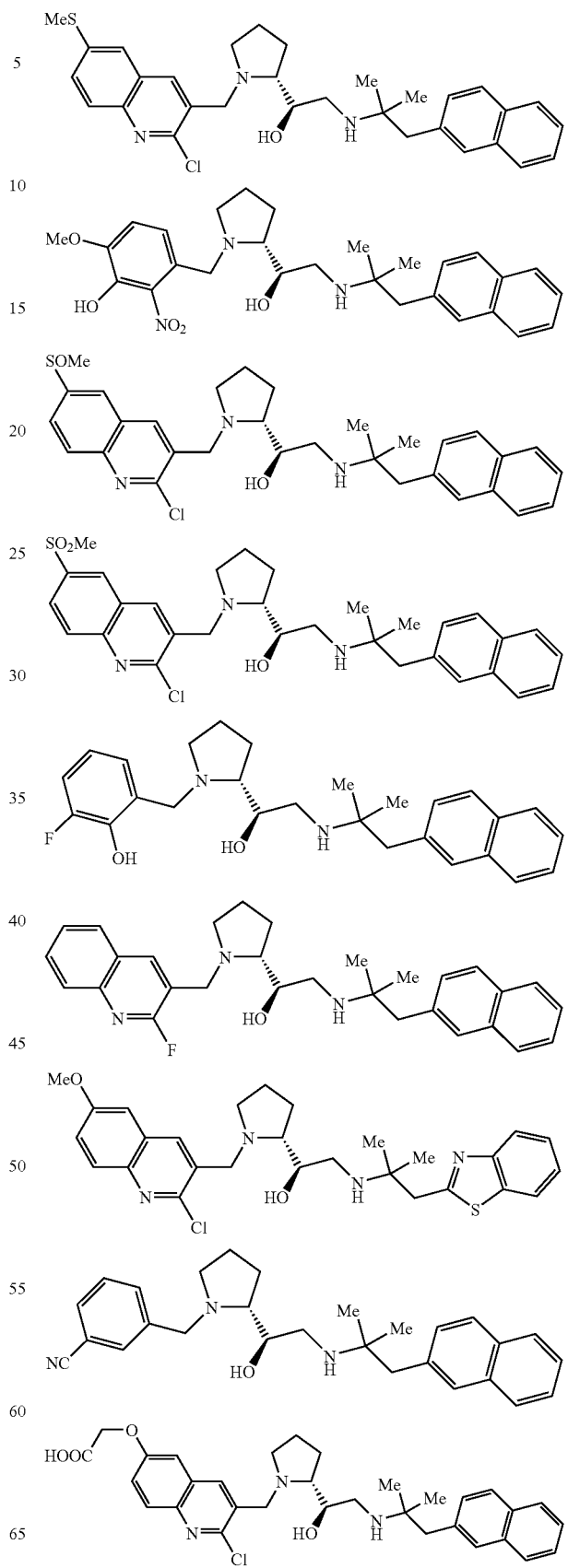

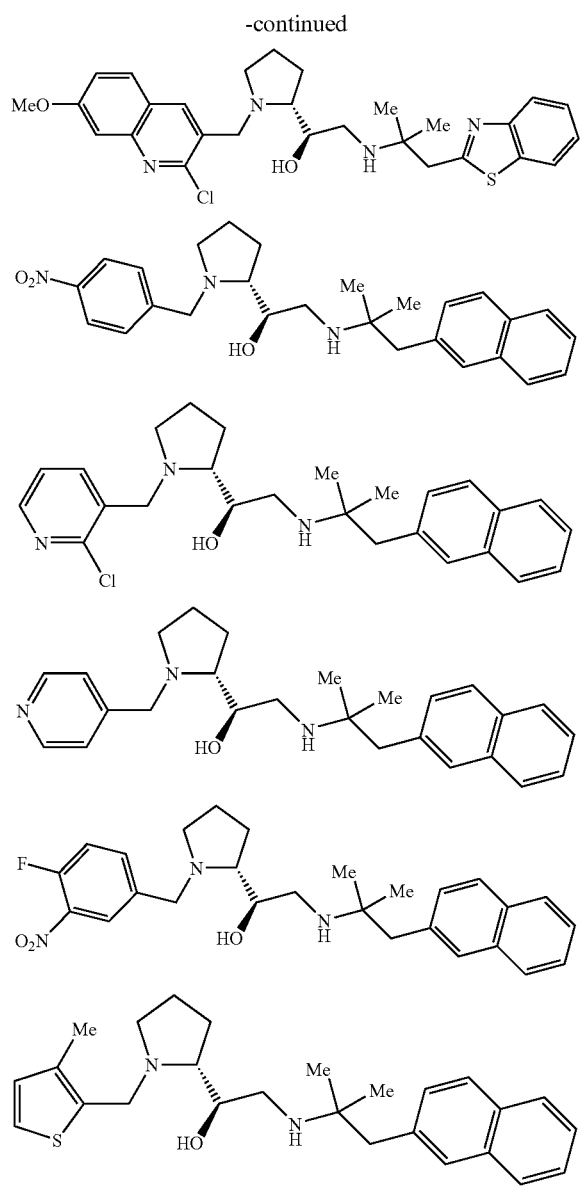

[6] In another more preferred embodiment, the present invention provides compound of formula I wherein the compound is selected from:

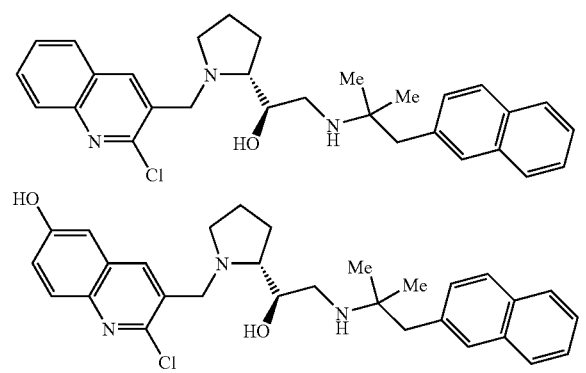

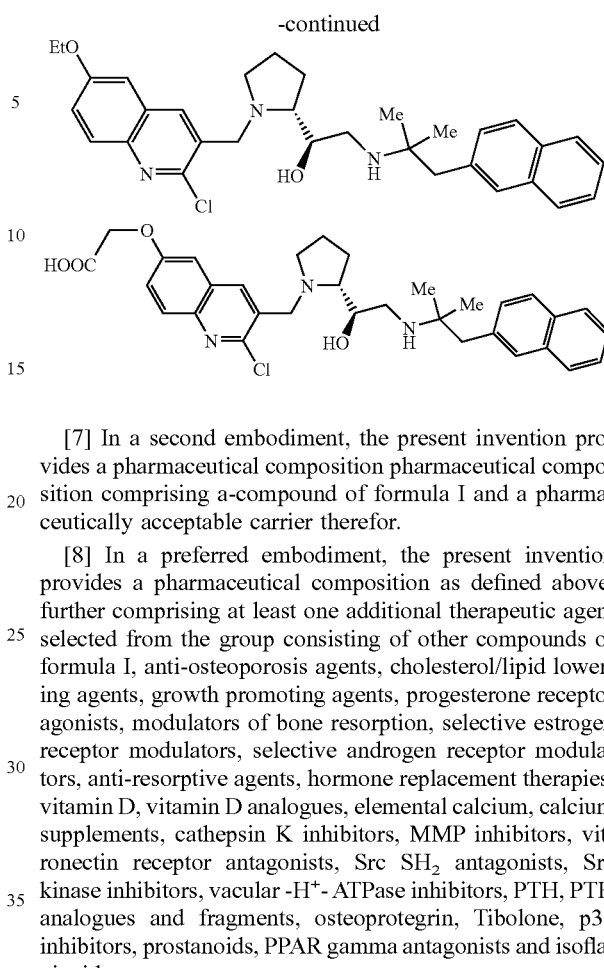

[7] In a second embodiment, the present invention provides a pharmaceutical composition pharmaceutical composition comprising a-compound of formula I and a pharmaceutically acceptable carrier therefor.

[8] In a preferred embodiment, the present invention provides a pharmaceutical composition as defined above, further comprising at least one additional therapeutic agent selected from the group consisting of other compounds of formula I, anti-osteoporosis agents, cholesterol/lipid lowering agents, growth promoting agents, progesterone receptor agonists, modulators of bone resorption, selective estrogen receptor modulators, selective androgen receptor modulators, anti-resorptive agents, hormone replacement therapies, vitamin D, vitamin D analogues, elemental calcium, calcium supplements, cathepsin K inhibitors, MMP inhibitors, vitronectin receptor antagonists, Src $SH_2$ antagonists, Src kinase inhibitors, vacular -$H^+$- ATPase inhibitors, PTH, PTH analogues and fragments, osteoprotegrin, Tibolone, p38 inhibitors, prostanoids, PPAR gamma antagonists and isoflavinoids.

[9] In a third embodiment, the present invention provides a method for treating or delaying the progression or onset of hypoparathyroidism, osteosarcoma, chondrosarcoma, periodontal disease, fracture healing, osteoarthritis, Paget's disease, osteopenia, glucocorticoid induced osteoporosis, osteomalacia, osteoporosis, metastatic bone disease or joint replacement, which comprises administering to a mammalian species in need of treatment a therapeutically effective amount of a compound of formula I.

[10] In another preferred embodiment, the present invention provides a method as defined above, further comprising administering, concurrently or sequentially, a therapeutically effective amount of at least one additional therapeutic agent selected from the group consisting of other compounds of formula I, anti-osteoporosis agents, cholesterol/lipid lowering agents, growth promoting agents, progesterone receptor agonists, modulators of bone resorption, selective estrogen receptor modulators, selective androgen receptor modulators, anti-resorptive agents, hormone replacement therapies, vitamin D, vitamin D analogues, elemental calcium, calcium supplements, cathepsin K inhibitors, MMP inhibitors, vitronectin receptor antagonists, Src $SH_2$ antagonists, Src kinase inhibitors, vacular -$H^+$- ATPase inhibitors, PTH, PTH analogues and fragments, osteoprotegrin, Tibolone, p38 inhibitors, prostanoids, PPAR gamma antagonists and isoflavinoids.

[11] In another preferred embodiment, the present invention provides a method of enhancing bone formation in a mammalian species comprising administering a therapeutically effective amount of a compound of formula I to a patient in need thereof.

[12] In a fourth embodiment, the present invention provides a pharmaceutical composition capable of modulating the calcium sensing receptor comprising a compound of formula I

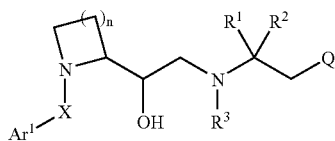

wherein:

Ar¹ is a substituted or unsubstituted aryl or substituted or unsubstituted heteroaryl;

X is a linking group selected from the group consisting of alkylene, CO, alkyleneCO, OCO, alkyleneOCO, $SO_2$ and alkyleneSO$_2$;

n is an integer from 1 to 4;

$R^1$ and $R^1$ are each independently substituted or unsubstituted $C_1$–$C_4$ alkyl, or $R^1$ can be cyclized with $R^2$ to form (—CH$_2$—)$_m$ where m is an integer from 2 to 5;

$R^3$ is hydrogen(H) or alkyl;

Q is Ar¹ or G;

G is

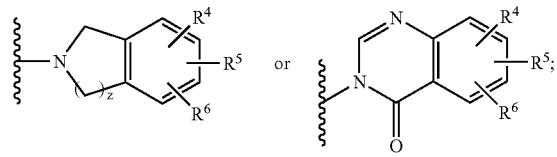

z is 1 or 2; and $R^4$, $R^5$ and $R^6$ are each independently selected from the group consisting of hydrogen, halo, haloalkyl, alkyl, alkoxy, haloalkoxy, hydroxy, cyano, nitro, amino, alkylamino and alkylthio;

including all prodrug esters, pharmaceutically acceptable salts or stereoisomers thereof.

[13] In a preferred embodiment, the present invention provides a pharmaceutical composition as defined above wherein said composition is a calcium sensing receptor antagonist.

The following definitions apply to the terms as used throughout this specification, unless otherwise limited in specific instances.

The term "alkyl" or "lower alkyl" as employed herein, alone or as part of another group, includes both straight and branched chain hydrocarbons, containing 1 to 12 carbons, preferably 1 to 8 carbons, more preferably 1 to 4 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. As defined and claimed herein, the term "alkyl" includes alkyl groups as defined above optionally substituted with one or more substituents commonly attached to such chains, such as, but not limited to halo, for example F, Br, Cl or I or CF$_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, haloalkyl, trihaloalkyl, alkylthio, carboxyl, and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

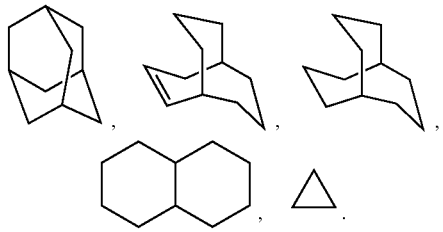

As defined and claimed herein, the term "cycloalkyl" includes cycloalkyl groups as defined above optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl."

The term "halogen" or "halo" as used herein alone or as part of another group refers to chlorine, bromine, fluorine, and iodine.

Unless otherwise indicated, the term "aryl", "aromatic" or "Ar" as employed herein alone or as part of another group refers to monocyclic and polycyclic (conjugated or fused) aromatic groups containing 5 to 14 carbons in the ring portion (such as phenyl or naphthyl, including 1-naphthyl and 2-naphthyl) and may optionally include one to three additional rings fused to a carbocyclic ring or a heterocyclic ring (such as aryl, cycloalkyl, heteroaryl or cycloheteroalkyl rings, for example

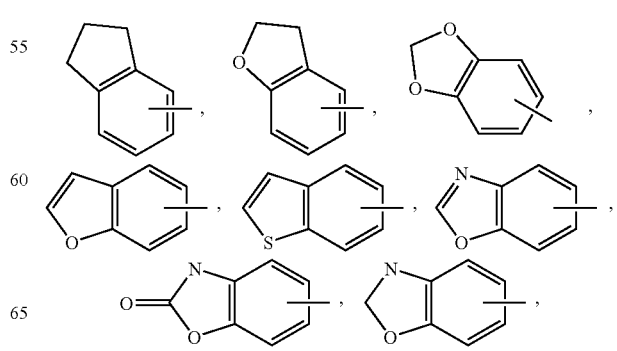

-continued

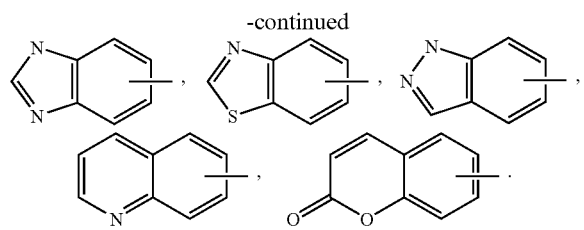

As defined and claimed herein, the term "aryl", "aromatic" or "Ar" includes aryl groups as defined above optionally substituted through any available carbon atoms with one or more substitutents, such as hydrogen, halo, haloalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, heteroarylalkyl, aryloxy, aryloxyalkyl, alkoxyalkyl, arylalkoxy, alkoxycarbonyl, aryloxycarbonyl, arylalkoxycarbonyl, arylalkenyl, heteroarylalkenyl, heteroarylheteroaryl, heteroaryloxy, heteroarylalkoxy, heteroaryloxyalkyl, aminocarbonylalkyl, aminocarbonylaryl, arylthio, arylalkylthio, heteroarylalkylthio, arylazo, hydroxy, nitro, cyano, carboxyl, carboxylalkoxy, alkoxycarbonylalkoxy, amino, substituted amino, wherein the amino includes 1 or 2 substituents such as alkyl, aryl (or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, alkylsulfonyl, arylsulfonyl, heteroarylsulfonyl, cycloheteroalkylsulfonyl, alkylsulfinyl, arylsulfinyl, arylsulfinylalkyl, arylsulfonylamino, arylsulfonaminocarbonyl and/or any of the alkyl substituents set out herein.

The term "fused" refers to aromatic or heteroaromatic rings that share a pair of carbon atoms, and includes multiple fused aromatic or heteroaromatic rings, for example naphthalene or naphthyridine.

Unless otherwise indicated, the term "heteroaryl" or "heteroaromatic" as used herein alone or as part of another group refers to a 5- or 6-membered aromatic ring which includes 1, 2, 3 or 4 hetero atoms such as nitrogen, oxygen, or sulfur, and such rings fused to an aryl, cycloalkyl, heteroaryl or cycloheteroalkyl ring (e.g. benzothiophenyl, indole), and includes possible N-oxides. As defined and claimed herein, the term "heteroaryl" or "heteroaromatic" includes heteroaryl groups as defined above optionally substituted through any available carbon atoms with one or more substituents such as any of the alkyl or aryl substituents set out above. Examples of heteroaryl groups include the following:

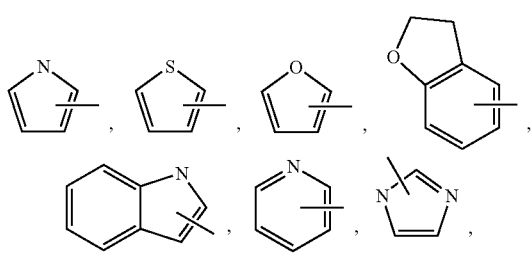

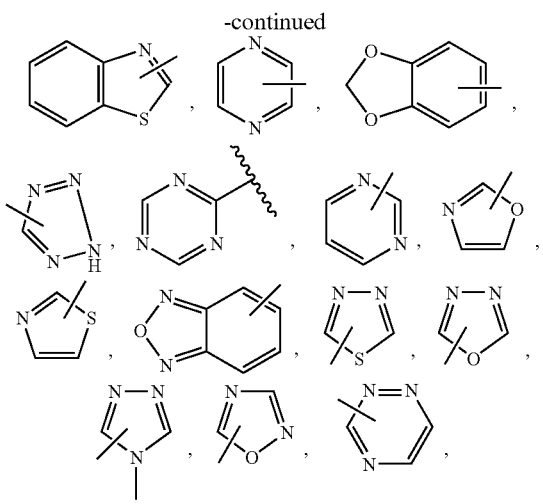

and the like.

Unless otherwise indicated, the term "alkoxy", "aryloxy" or "arylalkoxyl" as employed herein alone or as part of another group includes any of the above alkyl, arylalkyl or aryl groups linked to an oxygen atom.

Unless otherwise indicated, the term "alkylthio" or "arylthio" as employed herein alone or as part of another group includes any of the above alkyl, arylalkyl or aryl groups linked through a sulfur atom.

Unless otherwise indicated, the term "alkylamino" or "arylamino" as employed herein alone or as part of another group includes any of the above alkyl, aryl or arylalkyl groups linked through a nitrogen atom.

Unless otherwise indicated, the term "haloalkyl" or "haloalkoxy" as employed herein alone or as part of another group includes a halo group, linked through an alkyl group or alkoxy group, respectively.

The term "cyano," as used herein, refers to a —CN group.

The term "carboxyl" denotes —C(O)O—.

The term "nitro" as used herein, refers to a —NO$_2$ group.

The term "hydroxy" as used herein, refers to —OH.

The term "amino" refers to a group of the formula —NZ$_1$Z$_2$ wherein Z$_1$ and Z$_2$ are each hydrogen, or Z$_1$ and Z$_2$ may each independently be alkyl, aryl or any of the substituents described for substituted alkyl or substituted aryl above.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluene- sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

*The Practice of Medicinal Chemistry*, Camille G. Wermuth et al., Ch 31, (Academic Press, 1996);

*Design of Prodrugs*, edited by H. Bundgaard, (Elsevier, 1985); and

*A Textbook of Drug Design and Development*, P. Krogsgaard-Larson and H. Bundgaard, eds. Ch 5, pgs 113–191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

Scheme 1

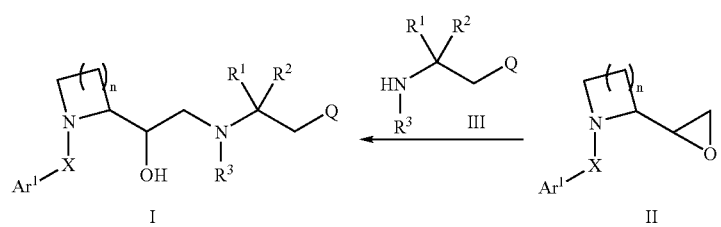

-continued

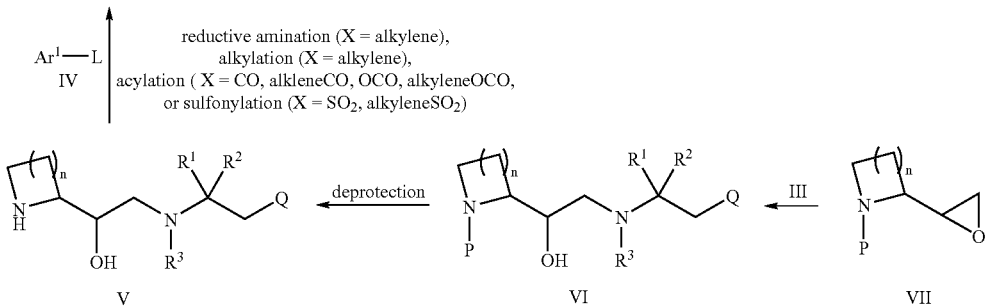

P = a protecting group

Compound I can be prepared from the N-functionalized epoxide II by coupling of the amine III, either by heating the mixture neat or, preferably, in an alcoholic solvent, such as ethanol or isopropanol, as given in Scheme 1. Alternatively, the unfunctionalized amine V can be reacted with the appropriate alkylating, acylating, or sulfonylating reagent to provide compound I. In the cases where X contains an alkylene group, this can be accomplished by reductive amination with the appropriate aldehyde and a reducing agent, such as sodium borohydride, sodium cyanoborohydride, or sodium triacetoxyborohydride, in a solvent such as methanol, THF, or DMF; or, alkylation can be performed by reaction of the appropriate alkyl halide (Cl, Br, or I) and an inorganic or tertiary amine base, such as potassium carbonate or triethylamine, in a polar solvent such as DMF or acetonitrile. In the cases where X contains a carbonyl group, this can be accomplished by acylation with the appropriate acid halide, preferably in the presence of a tertiary amine base such as triethylamine or N,N-diisopropylethylamine, in a solvent such as dichloromethane or chloroform; or, the appropriate carboxylic acid can coupled through the reaction of standard acylation reagents such as 1-(3-dimethylaminopropyl)-3-ethylcarbodiimide (EDC) and 1-hydroxybenztriazole (HOBt), or bromotripyrrolidinophosphonium hexafluorophosphate (PyBroP) according to the literature. In the cases where X contains a sulfonyl group, this can be accomplished by sulfonylation with the appropriate sulfonyl chloride, with or without a tertiary amine base such as triethylamine, in a solvent such as dichloromethane, but preferably in pyridine.

Compound V can be prepared from the protected cyclic amine, compound VI, where P is a protecting group. Suitable protecting groups or references thereto can be found, along with the appropriate deprotection conditions, in Greene, Theodora W.; Wuts, Peter G. M. Protective Groups in Organic Synthesis, 3$^{rd}$ ed.; Wiley & Sons: New York, 1999. Preferably, P is a carbamate protecting group, such as benzyloxycarbonyl (Cbz) or tert-butoxycarbonyl (BOC). The protected amine VI can be prepared from coupling of the epoxide VII and the amine III in a manner similar to that for the preparation of compound I.

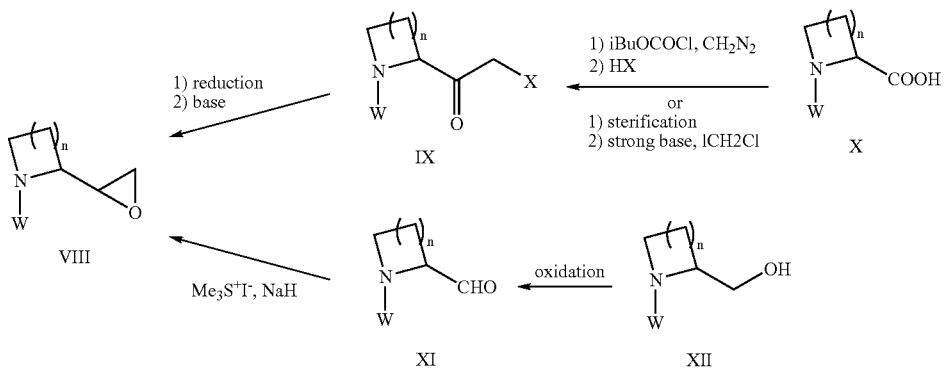

Scheme 2

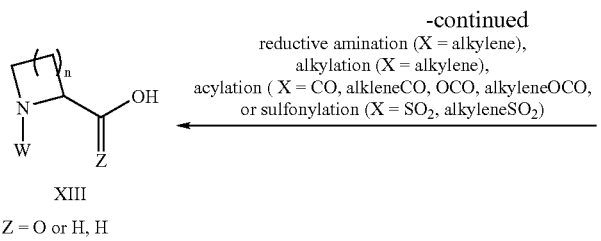

XIII  
Z = O or H, H

XIV

The intermediate epoxides II and VII can be prepared according to Scheme 2. Reduction of the carbonyl group of the halomethyl ketone IX, with a reagent such as sodium borohydride or L-selectride, preferably at a temperature between −78° C. and 0° C., in a solvent such as THF, followed by treatment with a base such as potassium hydroxide in methanol can provide compound VIII. Alternatively, epoxide formation can arise from treatment of the aldehyde XI with a methylsulfonium ylide. The halomethyl ketone IX can be prepared from the corresponding carboxylic acid through reaction of an acylating agent, preferably a mixed anhydride, with diazomethane followed by treatment with the appropriate hydrogen halide; or, by esterification followed by treatment with the reagent formed by reaction of a strong base with chloroiodomethane. The aldehyde XI can be prepared by oxidation of the alcohol XII under standard conditions, as referred to in Hudlicky, M. Oxidations in Organic Chemistry; ACS Monograph 186; Wiley & Sons: New York, 1990 or Larock, R. C. Comprehensive Organic Transformations; American Chemical Society: Washington, D.C., 1989.

The functionalized amines X and XII can be prepared by reacting the unfunctionalized amine XIV with the appropriate alkylating, acylating, or sulfonylating reagent (see Scheme 1) to provide compound XIII. The amine starting materials XIV are either commercially available, known in the literature, or can be prepared according to the synthesis of similar analogs prepared in the literature.

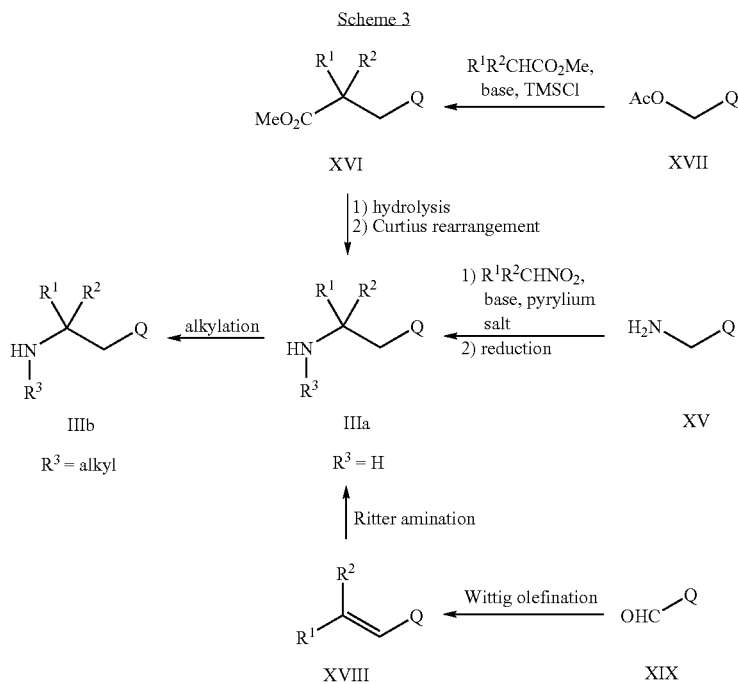

Preparation of compound III is provided in Scheme 3. Treatment of the appropriate primary amine XV with a pyrylium salt, such as 2,4,6-triphenylpyrylium tetrafluoroborate, followed by reaction of an appropriately substituted nitroalkane in the presence of a strong base, such as sodium methoxide, provides an intermediate nitro compound, which can be reduced to the corresponding primary amine IIIa, under reducing conditions such as hydrogen gas (at atmospheric pressure or up to 80 psig) over a Pd catalyst or Raney nickel, in a solvent such as methanol or ethyl acetate. Alternatively, IIIa can arise from ester XVI via hydrolysis to the carboxylic acid, using for example aqueous sodium hydroxide in methanol, followed by Curtius rearrangement, using for example diphenylphosphoryl azide and benzyl alcohol followed by hydrogenolysis. Ester XVI can be prepared from reaction of the appropriate ketene acetal with the acetate XVII. Preparation of IIIa is also possible via amination of the olefin XVIII under Ritter conditions, such as through treatment with sodium cyanide, acetic acid, and sulfuric acid, followed by base hydrolysis of the intermediate amide. Wittig olefination of the appropriate aldehyde XIX can provide olefin XVIII. The starting materials XV, XVII, and XIX are either commercially available, known in the literature, or can be prepared according to the synthesis of similar analogs prepared in the literature.

Utilities & Combinations

A. Utilities

Diseases or disorders which can be treated by modulating calcium sensing receptor activity can be identified based on the functional responses of cells regulated by calcium receptor activity. Functional responses of cells regulated by the calcium sensing receptor are known in the art, including parathyroid hormone ("PTH") secretion by parathyroid cells, calcitonin secretion by C-cells, bone reabsorption by osteoclasts and $Ca^{2+}$ secretion by kidney cells.

The compounds of the present invention preferably function as modulators of the calcium sensing receptor, particularly as antagonists of the calcium sensing receptor. Accordingly, the compounds of the invention may be used to stimulate a functional response by parathyroid cells whereby such cells release PTH, preferably a transient release of PTH. Thus, the compounds of the present invention may be used in the treatment of diseases or disorders which can be affected by modulating one or more activities or functions of a calcium sensing receptor, wherein treatment comprises prevention, partial alleviation or cure of the condition or disorder. Modulation may occur locally, for example with certain tissues of the subject, or more extensively throughout a subject being treated for such a condition or disorder.

The compounds of the present invention can be administered animals, including humans, for the treatment of a variety of conditions and disorders, including, but not limited to bone and mineral-related diseases or disorders, (e.g., hypoparathyroidism, osteosarcoma, chondrosarcoma, periodontal disease, fracture healing, osteoarthritis, Paget's disease, osteopenia, glucocorticoid induced osteoporosis, osteomalacia and osteoporosis); metastatic bone disease; joint replacement; diseases involving excess water reabsorption by the kidney, such as syndrome of inappropriate ADA secretion (SIADH), cirrhosis, congestive heart failure and nephrosis; hypertension; diseases involving abnormally low serum parathyroid levels; preventing and/or decreasing renal toxicity from cationic antibiotics (e.g., amionglycoside antibiotics); renal osteodystrophy; gutmotility disorders, such as diarrhea and spastic colon, GI ulcer diseases; GI diseases with excessive calcium absorption; Sarcoidosis; autoimmune diseases and organ transplant rejection; inflammatory diseases, such as ashthma, rheumatoid arthritis, inflammatory bowel disease, transplant rejection, and chronic obstructive pulmonary disease; and diseases caused by excess gastric acid secretion.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s) or other pharmaceutically active materials.

The compounds of the present invention may be employed in combination other modulators of the calcium sensing receptor or other suitable therapeutic agents useful in the treatment of the aforementioned disorders including: anti-osteoporosis agents, cholesterol/lipid lowering agents, growth promoting agents and/or progesterone receptor agonists.

Examples of suitable anti-osteoporosis agents for use in combination with the compounds of the present invention include bisphosphonates (e.g., alendronate, risedronate, ibandronate and zolendrate) parathyroid hormone, PTH fragment, calcitonins, RANK ligand antagonists, TRAP inhibitors and AP-1 inhibitors.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)).

Examples of suitable growth promoting agents for use in combination with the compounds of the present invention include growth hormone secretagogues, such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine.

Examples of suitable progesterone receptor agonists for use in combination with the compounds of the present invention include levonorgestrel and medroxyprogesterone acetate (MPA).

The compounds of the present invention may further be used in combination with modulators of bone resorption (e.g., estrogen); selective estrogen receptor modulators (e.g., tamoxifen, lasofoxifene, TSE-424 and raloxifene); or selective androgen receptor modulators, such as those disclosed in Edwards, J. P. et al., *Bio. Med. Chem. Let.*, 9, 1003–1008 (1999) and Hamann, L. G. et al., *J. Med. Chem.*, 42, 210–212 (1999).

In addition, compounds of the present invention may be used in combination with therapeutic agents such as antiresorptive agents; hormone replacement therapies; vitamin D and analogues thereof (e.g., 1,25-dihydroxy vitamin D3); elemental calcium and calcium supplements; cathepsin K inhibitors; MMP inhibitors; vitronectin receptor antagonists; Src $SH_2$ antagonists; Src kinase inhibitors; vacular -$H^+$-ATPase inhibitors; PTH and its analogues and fragments; osteoprotegrin; Tibolone; p38 inhibitors; prostanoids; PPAR gamma antagonists or isoflavinoids (e.g., genistein, iprifla-vone and testosterone).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral-oil gelled with polyethylene).

The effective amount of a compound of the present invention can be determined by one of ordinary skill in the art, and includes exemplary dosage amounts for a adult human of from about 0.001 to 100 mg/kg of body weight of active compound per day, preferably 0.01 to 1 mg/kg of body weight of active compound per day,that can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

The following examples serve to better illustrate, but not limit, some of the preferred embodiments of the invention.

The following abbreviations are employed in the Examples:
AcOH=acetic acid
aq.=aqueous
Ar=argon
Bn=benzyl
BOC=tert-butoxycarbonyl
BOP reagent=benzotriazol-1-yloxy-tris (dimethylamino) phosphonium hexafluorophosphate
br=broad
Bu butyl
c=concentration
° C.=degrees Centigrade
CAN=ceric ammonium nitrate
CBZ=carbobenzyloxy or carbobenzoxy or benzyloxycarbonyl
$CDCl_3$=chloroform-d
$CD_3OD$=methanol-$d_4$
$CH_2Cl_2$=dichloromethane
$CHCl_3$=chloroform
$Cs_2CO_3$=cesium carbonate
d=doublet
DBU=1,8-diazabicyclo[5.4.0]undec-7-ene
DEAD=diethylazodicarboxylate
DIAD=diisopropylazodicarboxylate
DIBAL=diisobutylaluminum hydride
DMAP=4-dimethylaminopyridine
DME=1,2-dimethoxyethane
DMF=dimethylformamide
DMSO=dimethylsulfoxide
EDC=3-ethyl-3'-(dimethylamino)propylcarbodiimide hydrochloride
ES+=electrospray positive ionization
Et=ethyl
$Et_3N$=triethylamine
EtOAc=ethyl acetate
$Et_2O$=diethyl ether
EtOH=ethanol
FMOC=fluorenylmethoxycarbonyl
g=gram(s)
h=hour(s)
HCl=hydrochloric acid
hex=hexane or hexanes
$HNO_3$=nitric acid
$H_2O$=water
HOAc=acetic acid
HOAT=1-Hydroxy-7-azabenzotriazole
HOBT=1-hydroxybenzotriazole hydrate
HPLC=high performance liquid chromatography
$H_3PO_4$=phosphoric acid
$H_2SO_4$=sulfuric acid
Hz=hertz iPr=isopropyl
iPr$_2$NEt=diisopropylethylamine
iPrOH=isopropanol
K$_2$CO$_3$=potassium carbonate
KF=potassium fluoride
KHMDS=potassium bis(trimethylsilyl)amide
KHSO$_4$=potassium hydrogen sulfate
KOH=potassium hydroxide
L=liter(s)
LAH=lithium aluminum hydride
LC/MS=high performance liquid chromatography/mass spectrometry
LDA=lithium diisopropylamide
LiAlH$_4$=lithium aluminum hydride
LiHMDS=lithium bis(trimethylsilyl)amide
LiOH=lithium hydroxide
m=multiplet
M=molar
mCPBA=3-chloroperoxybenzoic acid
Me=methyl
MeOH=methanol
meq=milliequivalent(s)
mg=milligram(s)
MgSO$_4$=magnesium sulfate
MHz=megahertz
□L=microliter(s)
min=minute(s)
mL=milliliter(s)
mm=millimeter(s)
mmol=millimole(s)
MnO$_2$=manganese dioxide
mol=mole(s)
mp=melting point
MS or Mass Spec=mass spectrometry
N$_2$=nitrogen
NaBH$_4$=sodium borohydride
NaBH(OAc)$_3$=sodium triacetoxyborohydride
NaCNBH$_3$=sodium cyanoborohydride
NaHCO$_3$=sodium bicarbonate
NaHMDS=sodium bis(trimethylsilyl)amide
NaOH=sodium hydroxide
NaOMe=sodium methoxide
Na$_2$SO$_4$=sodium sulfate
nBuLi=n-butyllithium
NMM=N-methylmorpholine
NMO=N-methylmorpholine N-oxide
NMR=nuclear magnetic resonance
Pd/C=palladium on carbon
Pd(OAc)$_2$=Palladium acetate
Ph=phenyl
Ph$_3$P=triphenylphosphine
(Ph$_3$P)$_4$Pd=tetrakistriphenylphosphine palladium
P$_2$O$_5$=phosphorus pentoxide
POCl$_3$=phosphorus oxychloride
Pr=propyl
PtO$_2$=platinum oxide
RT=room temperature
s=singlet
sat or sat'd=saturated
t=triplet
TBS=tert-butyldimethylsilyl
tBu=tertiary butyl
TFA=trifluoroacetic acid
THF=tetrahydrofuran
Ti(OiPr)$_4$=titanium isopropoxide
TLC=thin layer chromatography
TMS=trimethylsilyl or trimethylsilane
UV=ultraviolet HPLC analysis of the exemplified compounds was carried out under one of the following reverse phase methods, with the appropriate method and retention time noted in the Examples.

Method A: YMC S5 ODS 4.6×50 mm column, gradient elution 0–100% B/A over 4 min (solvent A=10% MeOH/H$_2$O containing 0.2% H$_3$PO$_4$, solvent B=90% MeOH/H$_2$O containing 0.2% H$_3$PO$_4$), flow rate 4 mL/min, UV detection at 220 nm.

Method B: Phenomenex Luna S5 ODS 4.6×50 mm column, gradient elution 0–100% B/A over 4 min (solvent A=10% MeOH/H$_2$O containing 0.2% H$_3$PO$_4$, solvent B=90% MeOH/H$_2$O containing 0.2% H$_3$PO$_4$), flow rate 4 mL/min, UV detection at 220 nm.

Method C: Zorbax SB C18 4.6×75 mm column, gradient elution 0–100% B/A over 8 min (solvent A=10% MeOH/H$_2$O containing 0.2% H$_3$PO$_4$, solvent B=90% MeOH/H$_2$O containing 0.2% H$_3$PO$_4$), flow rate 2.5 mL/min, UV detection at 220 nm.

Method D: YMC S5 ODS 4.6×50 mm column, gradient elution 0–100% B/A over 4 min (solvent A=10% MeOH/H$_2$O containing 0.1% TFA, solvent B=90% MeOH/H$_2$O containing 0.1% TFA), flow rate 4 mL/min, UV detection at 220 nm.

Method E: Phenomenex S5 ODS 4.6×50 mm column, gradient elution 0–100% B/A over 4 min (solvent A=10% MeOH/H$_2$O containing 0.1% TFA, solvent B=90% MeOH/H$_2$O containing 0.1% TFA), flow rate 4 mL/min, UV detection at 220 nm.

Method F: YMC S5 ODS 4.6×75 mm column, gradient elution 0–100% B/A over 8 min (solvent A=10% MeOH/H$_2$O containing 0.2% H$_3$PO$_4$, solvent B=90% MeOH/H$_2$O containing 0.2% H$_3$PO$_4$), flow rate 2.5 mL/min, UV detection at 220 nm.

Preparative reverse phase HPLC purification of the exemplified compounds was carried out under one of the following methods, with the appropriate method and conditions noted in the Examples.

Method 1: Shimadzu VP ODS 20×100 mm column; solvent A=10% MeOH/H$_2$O containing 0.1% TFA, solvent B=90% MeOH/H$_2$O containing 0.1% TFA; flow rate 25 mL/min; UV detection at 220 nm.

Method 2: Shimadzu VP ODS 20×250 mm column; solvent A=10% MeOH/H$_2$O containing 0.1% TFA, solvent B=90% MeOH/H$_2$O containing 0.1% TFA; flow rate 20 mL/min; UV detection at 220 nm.

Method 3: YMC S5 ODS 30×250 mm column; solvent A=10% MeOH/H$_2$O containing 0.1% TFA, solvent B=90% MeOH/H$_2$O containing 0.1% TFA; flow rate 25 mL/min; UV detection at 220 nm.

Method 4: YMC S5 ODS 30×100 mm column; solvent A=10% MeOH/H$_2$O containing 0.1% TFA, solvent B=90% MeOH/H$_2$O containing 0.1% TFA; flow rate 40 mL/min; UV detection at 220 nm.

Method 5: Shimadzu VP ODS 20×50 mm column; solvent A=10% MeOH/H$_2$O containing 0.1% TFA, solvent B=90% MeOH/H$_2$O containing 0.1% TFA; flow rate 20 mL/min; UV detection at 220 nm.

EXAMPLE 1

A.

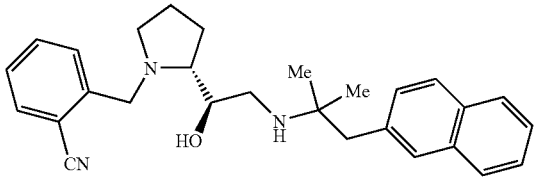

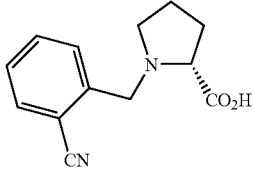

To a solution of (D)-proline (4.9 g, 42.56 mmol) and KOH (7.16 g, 127.6 mmol) in isopropanol (30 mL) was added 2-cyanobenzylbromide (10 g, 51.0 mmol). The reaction mixture was maintained at 40° C. for 6 h. The reaction mixture was allowed to cool to room temperature and the pH was adjusted to 5 with concentrated HCl. Dichloromethane (12 mL) was added and stirring continued for 1 h. The precipitate was filtered and washed with $CH_2Cl_2$. The organic layers were combined and concentrated to a yellow gum which was purified by flash chromatography on silica gel eluting with 10% MeOH in $CH_2Cl_2$ to give the title compound (6.8 g, 69%) as a white solid (mp 130–133° C.).

MS (ES+) m/z 231 [M+H]. $^1$H NMR (500 MHz, $CD_3OD$): δ 1.90–2.00 (m,1H); 2.08–2.18 (m, 2H); 2.42–2.52 (m,1H); 3.20–3.28 (m,1H); 3.54–3.62 (m,1H); 3.92–4.00 (m,1H); 4.50 (d,1H J=15.0 Hz); 4.70 (d,1H, J=15.0 Hz); 7.63 (dd,1H, J=10.0, 5.0 Hz); 7.79 (dd,1H, J=5.0, 10.0 Hz); 7.84 (d,1H, J=10.0 Hz); 7.94 (d,1H, J=10.0 Hz). $^{13}$C NMR (125.65 MHz, $CD_3OD$): δ 6 23.81; 29.68; 55.41; 56.70; 70.03; 114.69; 118.19; 131.23; 133.21; 134.45; 134.72; 136.25; 174.13. $[α]_D$:+15.57 (C=0.92, MeOH).

B.

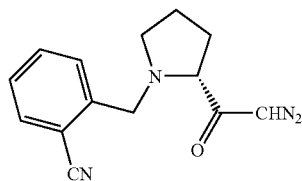

Preparation of diazomethane: To a mixture of 40% aqueous KOH (37.34 mL) and diethyl ether (125 mL) at 0° C. was added 1-methyl-3-nitro-1-nitrosoguanidine (11.7 g, 79.54 mmol) in small portions. The mixture was swirled several times. After 10 min, the yellow ethereal solution was decanted into a flask and dried over KOH pellets for 1 h at 0° C.

To a stirred slurry of the Part A compound (6.0 g, 26.06 mmol) in dry THF (60 mL) was added $Et_3N$ (3.81 mL, 27.34 mmol) at room temperature under argon. The reaction mixture was cooled to −15° C. after 40 min. To this cooled reaction mixture was added isobutyl chloroformate (3.38 mL, 26.06 mmol) over 5 min. The reaction mixture was stirred at −15° C. for 30 min and at room temperature for 20 min. The reaction mixture was filtered under nitrogen atmosphere into a cold (0° C.) flask. The precipitate was washed with ether (15 mL). The organic layers were combined and the solution of diazomethane in ether was added dropwise at 0° C. The reaction mixture was stirred at 0° C. for 30 min and at room temperature for 20 min. Excess of diazomethane was removed with a gentle stream of nitrogen. The crude diazomethylketone thus obtained was purified by flash chromatography on silica gel eluting with 20% ethyl acetate in hexane to give the title compound (5.5 g, 83%) as a yellow gum.

MS (ES+) m/z 255 [M+H]. $^1$H NMR (400 MHz, $CDCl_3$): 1.75–1.95 (m,3H); 2.18–2.30 (m,1H); 2.35–2.42 (m,1H); 2.98–3.05 (m,1H); 3.20–3.28 (m,1H); 3.75 (d,1H, J=13.64 Hz); 4.01 (d,1H, J=13.64 Hz); 6.09 (s,1H); 7.39 (dd,1H, J=7.48, 7.44 Hz); 7.50 (d,1H, J=7.48 Hz); 7.58 (dd,1H, J=6.60, 7.48 Hz); 7.67 (d,1H, J=7.48 Hz). $^{13}$C NMR (100.40 MHz, $CDCl_3$): 23.58; 30.66; 51.98; 53.89; 57.66; 72.05; 112.61; 118.02; 127.84; 130.16; 132.72; 133.06; 142.08; 198.40.

C.

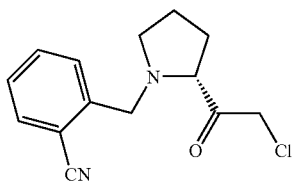

To a solution of the Part B compound (5.5 g, 21.63 mmol) in anhydrous ether (150 mL) at 0° C. was added slowly a solution of HCl in 1,4-dioxane (7.5 mL, 4M, 30.0 mmol) under argon. The reaction mixture was allowed to warm up to room temperature overnight. The reaction mixture was concentrated, diluted with $CH_2Cl_2$ (120 mL) and washed successively with 10% aqueous $NaHCO_3$, $H_2O$, and brine. The organic layer was dried over anhydrous $MgSO_4$ and concentrated. The crude product thus obtained was purified by flash chromatography on silica gel eluting with 10% ethyl acetate in hexane to provide the title compound (4.5, 79%) as a light brown gum.

MS (ES+) m/z 263 [M+H]. $^1$H NMR (400 MHz, $CDCl_3$): δ 1.84–1.96 (m,3H); 2.20–2.30 (m,1H); 2.46–2.54 (m,1H); 3.06–3.12 (m,1H); 3.48–3.54 (m,1H); 3.90 (Abq,2H); 4.38 (Abq,2H); 7.38–7.42 (m,1H); 7.52–7.62 (m,2H); 7.64–7.68 (m,1H). $^{13}$C NMR (100.40 MHz, $CDCl_3$): 23.90; 29.10; 46.10; 54.09; 57.46; 71.64; 112.39; 117.61; 127.92; 129.97; 132.84; 132.91; 141.85; 203.79.

D.

D1

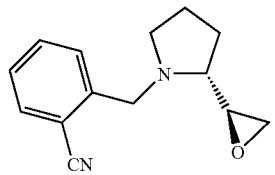

-continued

D2

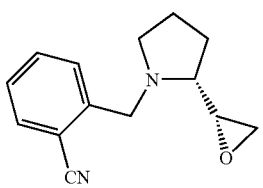

To a solution of the Part C compound (4.5 g, 17.12 mmol) in a mixture of MeOH and THF (60 mL, 1:1 v/v) at −10° C. was added sodium borohydride (650 mg, 17.18 mmol) in small portions under argon. The reaction mixture was allowed to stir at −10° C. for 1.5 h. The reaction was quenched with 5% aqueous KHSO$_4$ and concentrated. The residue was diluted with H$_2$O and extracted with ethyl acetate. The organic layer was washed with aqueous NaHCO$_3$ and brine, dried over MgSO$_4$ and concentrated to provide 4.5 g of the intermediate alcohol.

To a solution of the alcohol (4.5 g, 17.0 mmol) in EtOH (200 mL) was added under argon a solution of KOH (1.31 g, 2.04 mmol) in EtOH (10 mL). After 40 min of stirring, the solvent was removed under reduced pressure and the residue was dissolved in ethyl acetate (300 mL). The organic layer was washed with water followed by brine, dried over MgSO$_4$ and concentrated to give 3.85 g of the crude product. Flash chromatography on silica gel eluting with 1:1:3 (v/v/v) of ethyl acetate: hexanes: dichloromethane provided a diastereomeric mixture of compound D1 (350 mg, 9%) and compound D2 (350 mg, 9%) and 1.5 g of a mixture of compounds D1 and D2.

Compound D1:
MS (ES+) m/z 229 [M+H]. $^1$H NMR (400 MHz, CDCl$_3$): δ 1.70–1.90 (m,3H); 2.02–2.12 (m,1H); 2.28–2.46 (m,2H); 2.58–2.62 (m,1H); 2.72–2.78 (m,1H); 2.90–2.98 (m,2H); 3.66 (d, 1H, J=13.60 Hz); 4.16 (d,1H, J=13.64 Hz); 7.30–7.38 (m,1H); 7.52–7.68 (m,3H). $^{13}$C NMR (100.40 MHz, CDCl$_3$): □ 22.91; 28.68; 46.54; 54.28; 54.40; 57.22; 65.42; 112.20; 117.64; 127.28; 129.73; 132.44; 132.64; 143.64. [□]$_D$:+31.43 (C=0.75, MeOH)

Compound D2:
MS (ES+) m/z 229 [M+H]. $^1$H NMR (400 MHz, CDCl$_3$): δ 1.70–1.84 (m,3H); 1.88–2.00 (m,1H); 2.18–2.30 (m,2H); 2.48–2.50 (m,1H); 2.74–2.76 (m,1H); 2.88–2.96 (m,1H); 3.04–3.10 (m,1H); 3.62 (d,1H, J=14.08 Hz); 4.45 (d,1H, 14.08 Hz); 7.31–7.36 (m,1H); 7.52–7.58 (m,1H); 7.60–7.66 (m,1H). $^{13}$C NMR (100.40 MHz, CDCl$_3$): □ 22.62; 27.43; 43.06; 53.97; 54.83; 56.61; 67.02; 112.45; 117.86; 127.22; 130.03; 132.46; 132.71; 143.57. [α]$_D$:+45.64 (C=0.95, MeOH).

E.

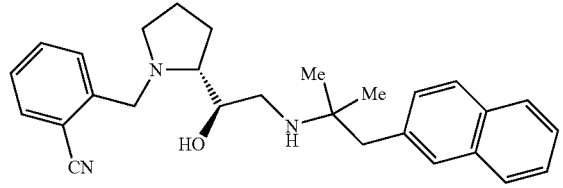

A mixture of the Part D1 compound (40 mg, 0.18 mmol) and 1,1-dimethyl-2-(2-naphthyl)ethylamine (35 mg, 0.18 mmol) (U.S. Pat. No. 6,022,894) in EtOH (0.5 ml) was stirred at 110° C. in a pressure tube under argon for 60 h. The reaction mixture was concentrated and purified by flash chromatography on silica gel eluting with 50% ethyl acetate in hexane followed by a step gradient of 5% to 10% methanol in dichloromethane to give the crude product. The crude product was further purified by preparative HPLC (Method 1, gradient elution 20–100% B/A over 15 min) to provide the title compound (28 mg, 21%) as a white foam.

MS (ES+) m/z 428 [M+H]. $^1$H NMR (500 MHz, CD$_3$OD): □ 1.41 (s,3H); 1.42 (s, 3H); 1.88–1.98 (m, 1H); 2.00–2.10 (m,1H); 2.19–2.28 (m,1H); 2.40–2.48 (m,1H); 3.23 (s,2H); 3.28–3.32 (m,2H); 3.38–3.48 (m,2H); 3.85–3.90 (m,1H); 4.20–4.28 (m,1H); 4.56 (d,1H, J=15.0 Hz); 5.10 (d,1H, J=15.0 Hz); 7.39–7.43 (m,1H); 7.46–7.52 (m,2H); 7.66–7.72 (m,1H); 7.79–7.92 (m,7H). $^{13}$C NMR (100.40 MHz, CD$_3$OD): □ 23.37; 23.51; 24.31; 28.45; 44.79; 46.17; 55.85; 58.55; 62.26; 69.29; 72.20; 115.98; 118.25; 127.22; 127.46; 128.65; 128.74; 129.22; 129.71; 130.77; 132.08; 133.36; 133.66; 134.12; 134.85; 134.93. HPLC retention time=2.033 min (Method A). [□]$_D$:−2.33 (c=0.21, MeOH). Elemental analysis calculated for 2.85 moles of TFA. Theoretical: % C: 53.79; % H: 4.80; % N: 5.58. Observed: % C: 53.89; % H: 4.89; % N: 5.61.

EXAMPLE 2

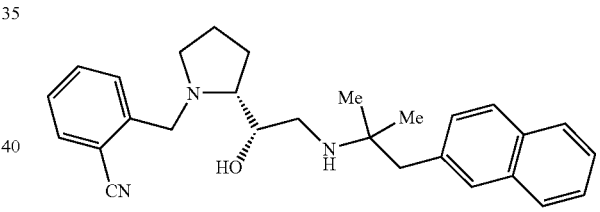

The procedure for Example 1 Part E, utilizing the Example 1 Part D2 compound (70 mg, 0.3 mmol), was followed to give the title compound (38 mg, 17%) as a white foam.

MS (ES+) m/z 428 [M+H]. $^1$H NMR (400 MHz, CD$_3$OD): □ 1.41 (s,6H); 1.98–2.08 (m, 1H); 2.12–2.30 (m,3H); 3.10–3.18 (m,1H); 3.23 (s,2H); 3.35–3.46 (m,2H); 3.48–3.55 (m,1H); 3.82–3.88 (m,1H); 4.48 (d,1H, J=13.60 Hz); 4.65 (d,1H, J=10.12 Hz); 4.86 (d,1H, J=13.64 Hz); 7.40–7.44 (m,1H); 7.46–7.52 (m,2H); 7.68–7.72 (m,1H); 7.79 (s,1H); 7.82–7.92 (m,6H). $^{13}$C NMR (125.65 MHz, CD$_3$OD): □ 22.82; 23.27; 23.44; 23.69; 44.76; 45.81; 55.64; 55.76; 62.14; 64.93; 71.09; 115.79; 118.77; 127.19; 127.43; 128.65; 128.75; 129.17; 129.74; 130.79; 132.12; 133.40; 133.91; 134.11; 134.81; 135.00. HPLC retention time=1.970 min (Method A). [□]$_D$:+5.83 (c=0.21, MeOH). Elemental analysis calculated for 2.55 moles of TFA. Theoretical: % C: 55.34; % H: 4.99; % N: 5.85. Observed: % C: 55.43; % H: 4.98; % N: 5.79.

EXAMPLE 3

A.

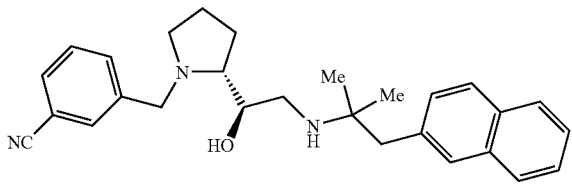

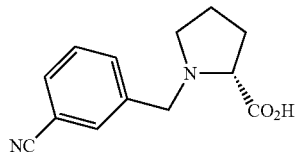

The procedure for Example 1 Part A, utilizing 3-cyanobenzylbromide (10.0 g, 51.0 mmol), was followed to give the title compound (4.05 g, 41%) as a white solid (mp 175–178° C.).

MS (ES+) m/z 231 [M+H]. $^1$H NMR (400 MHz, CD$_3$OD): □ 1.88–2.02 (m,1H); 2.06–2.18 (m,2H); 2.40–2.52 (m,1H); 3.12–3.24 (m,1H); 3.52–3.60 (m,1H); 3.88–3.92 (m,1H); 4.34 (1,d, J=12.72 Hz); 4.52 (d,1H, J=12.76 Hz); 7.58–7.64 (m,1H); 7.77–7.81 (m,1H); 7.85–7.90 (m,1H); 7.97 (1,s). $^{13}$C NMR (100.40 MHz, CD$_3$OD): □ 23.94; 29.97; 55.47; 58.25; 69.96; 114.01; 119.10; 131.15; 134.14; 134.33; 135.23; 136.23; 173.30. [α]$_D$:+10.74 (C=0.6, MeOH).

B.

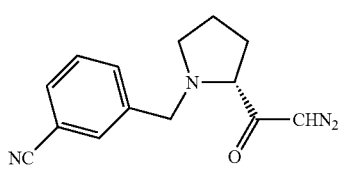

The procedure for the Example 1 Part B compound, utilizing the Part A compound (4.0 g, 17.37 mmol), was followed to give the title compound (3.45 g, 78%) as a white foam.

MS (ES+) m/z 255 [M+H]. $^1$H NMR (400 MHz, CDCl$_3$): □ 1.78–1.98 (m,3H); 2.18–2.32 (m,2H); 2.98–3.04 (m,1H); 3.18–3.26 (m,1H); 3.46 (d,1H, J=13.64 Hz); 3.96 (d,1H, J=13.64 Hz); 5.98 (s,1H); 7.44–7.48 (m,1H); 7.54–7.60 (m,2H); 7.66 (s,1H). $^{13}$C NMR (100.40 MHz, CDCl$_3$): □ 23.51; 30.37; 51.71; 53.81; 58.39; 71.71; 112.32; 118.68; 129.08; 130.77; 131.84; 132.86; 140.17; 198.26.

C.

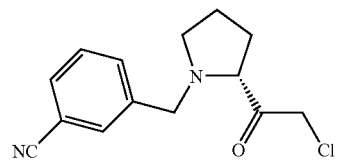

The procedure for the Example 1 Part C compound, utilizing the Part B compound (3.45 g, 13.57 mmol), was followed to give the title compound (3.5 g, 100%) as a yellow gum.

MS (ES+) m/z 263 [M+H]. $^1$H NMR (400 MHz, CDCl$_3$): 1.80–1.96 (m,3H); 2.15–2.30 (m,1H); 2.32–2.40 (m,1H); 2.98–3.08 (m,1H); 3.45–3.52 (m,1H); 3.55 (d,1H, J=13.64); 3.90 (d,1H, J=13.64 Hz); 4.38 (Abq,2H); 7.42–7.48 (m,1H); 7.52–7.62 (m,2H); 7.64 (s,1H). $^{13}$C NMR (100.40 MHz, CDCl$_3$): □ 23.75; 28.95; 46.04; 53.70; 58.52; 71.31; 112.43; 118.60; 129.20; 130.98; 131.84; 132.89; 139.86; 203.63.

D.

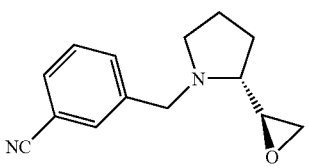
D1

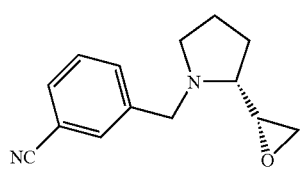
D2

To a solution of the Part C compound (3.4 g, 12.94 mmol) in a mixture of MeOH and THF (50 mL, 1:1 v/v) at −10° C. was added sodium borohydride (490 mg, 12.95 mmol) in small portions under argon. The reaction mixture was allowed to stir at −10° C. for 1.5 h. The reaction was quenched with 5% aqueous KHSO$_4$ and concentrated. The residue was diluted with H$_2$O and extracted with ethyl acetate. The organic layer was washed with aqueous NaHCO$_3$ and brine, dried over MgSO$_4$ and concentrated to provide 1.8 g of the intermediate alcohol.

To a solution of the alcohol (1.8 g, 6.8 mmol) in EtOH (75 mL) was added under argon a solution of KOH (525 mg, 0.82 mmol) in EtOH (5 mL). After 40 min of stirring, solvent was removed under reduced pressure and the residue was dissolved in ethyl acetate (150 mL). The organic layer was washed with water followed by brine, dried over MgSO$_4$ and concentrated to give the crude product. Flash chromatography over silica gel eluting with 1:1:3 (v/v/v) of ethyl acetate: hexanes: dichloromethane provided a diastereomeric mixture of compound D1 (315 mg, 20%) and compound D2 (110 mg, 7%), and 1.0 g of a mixture of compounds D1 and D2.

Compound D1:

MS (ES+) m/z 229 [M+H]. $^1$H NMR (500 MHz, CDCl$_3$): δ 1.70–1.86 (m,3H); 1.90–1.98 (m,1H); 2.10–2.20 (m,2H); 2.46–2.50 (m,1H); 2.72–2.78 (m,1H); 2.88–2.94 (m,1H); 2.96–3.02 (m,1H); 3.38 (d,1H, J=13.75 Hz); 4.35 (d,1H, 14.30 Hz); 7.39–7.44 (m,1H); 7.50–7.54 (m,1H); 7.60–7.63 (m,1H); 7.70 (s,1H). $^{13}$C NMR (125.7 MHz, CDCl$_3$): □ 22.45; 27.30; 42.90; 53.75; 54.88; 57.72; 66.67; 111.97; 118.89; 128.73; 130.30; 132.05; 133.04; 141.06. [□]$_D$:+ 39.68(C=0.70, MeOH).

Compound D2:

MS (ES+) m/z 229 [M+H]. $^1$H NMR (400 MHz, CDCl$_3$): δ 1.72–1.88 (m,3H); 2.02–2.08 (m,1H); 2.18–2.26 (m,1H); 2.38–2.44 (m,1H); 2.56–2.60 (m,1H); 2.68–2.72 (m,1H);

2.88–2.96 (m,2H); 3.42 (d,1H, J=13.64 Hz); 4.05 (d,1H, 13.20 Hz); 7.38–7.44 (m,1H); 7.52–7.60 (m,2H); 7.66 (s,1H). $^{13}$C NMR (100.40 MHz, CDCl$_3$): □ 22.96; 28.59; 46.15; 54.35; 54.49; 58.80; 64.91; 112.15; 118.86; 128.88; 130.48; 131.88; 132.81; 141.60. [α]$_D$:+40.98 (c=0.65, MeOH).

E.

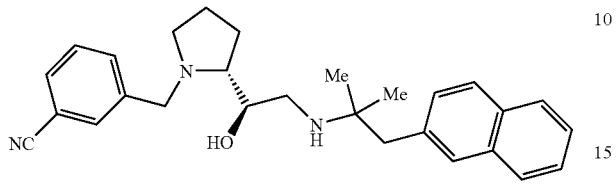

A mixture of the Part D1 compound (40 mg, 0.18 mmol) and 1,1-dimethyl-2-(2-naphthyl)ethylamine (35 mg, 0.18 mmol) in EtOH (0.5 mL) was stirred at 110° C. in a pressure tube under argon for 60 h. The reaction mixture was concentrated and purified by flash chromatography on silica gel eluting with 50% ethyl acetate in hexane followed by a step gradient of 5% to 10% methanol in dichloromethane to give the crude product. The crude product was purified by preparative HPLC (Method 1, gradient elution 20–100% B/A over 15 min) to provide the title compound (38 mg, 29%) as a white foam.

MS (ES+) m/z 428 [M+H]. $^1$H NMR (400 MHz, CD$_3$OD): □ 1.22 (s,3H); 1.24 (s, 3H); 1.65–1.80 (m, 3H); 1.88–2.02 (m,1H); 2.24–2.32 (m,1H); 2.78–2.92 (m,3H); 2.98–3.08 (m,3H); 3.50 (d,1H, J=13.60 Hz); 3.72–3.80 (m,1H); 4.15 (d,1H, J=13.64 Hz); 7.36–7.41 (m,1H); 7.42–7.50 (m,3H); 7.58–7.62 (m,1H); 7.64–7.68 (m,1H); 7.74 (s,2H); 7.78–7.86 (m,3H). $^{13}$C NMR (100.40 MHz, CD$_3$OD): □ 24.92; 25.23; 25.68; 27.77; 45.63; 46.83; 55.64; 57.49; 60.78; 68.22; 72.79; 113.33; 119.81; 126.77; 127.15; 128.57; 128.67; 128.72; 130.05; 130.34; 130.45; 131.83; 133.38; 133.86; 134.60; 134.82; 135.47; 142.89. HPLC retention time=1.997 min (Method A). [□]$_D$:-3.99 (c=0.24, MeOH) Elemental analysis calculated for 2.75 moles of TFA. Theoretical: % C: 54.29; % H: 4.86; % N: 5.67. Observed: % C: 54.37; % H: 5.03; % N: 5.63.

EXAMPLE 4

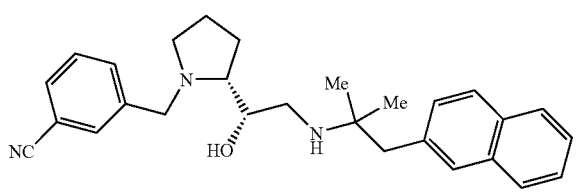

The procedure for Example 3 Part E, utilizing the Example 3 Part D2 compound (55 mg, 0.24 mmol), was followed to give the title compound (20 mg, 12%) as a white foam.

MS (ES+) m/z 428 [M+H]. $^1$H NMR (500 MHz, CD$_3$OD): □ 1.41 (s,6H); 1.98–2.08 (m, 1H); 2.14–2.28 (m,3H); 3.04–3.10 (m,1H); 3.20 (s,2H); 3.28–3.36 (m,2H); 3.38–3.46 (m,1H); 3.72–3.80 (m,1H); 4.32 (d,1H, J=15.0 Hz); 4.42 (d,1H, J=10.0 Hz); 4.67 (d,1H, J=15.0 Hz); 7.38–7.42 (m,1H); 7.46–7.52 (m,2H); 7.68 (t,1H); 7.78 (s,1H); 7.84–7.88 (m,4H); 7.91 (d,1H); 8.01 (s,1H). $^{13}$C NMR (125.65 MHz, CD$_3$OD): □ 22.55; 23.23; 23.43; 23.87; 44.77; 45.66; 55.53; 57.14; 62.10; 64.70; 70.78; 14.58; 118.87; 127.21; 127.45; 128.66; 128.73; 129.19; 129.72; 130.79; 131.52; 132.93; 133.36; 134.12; 134.85; 135.77; 136.78. HPLC retention time=1.900 min (Method A). [□]$_D$:-6.46 (c=0.17, MeOH) Elemental analysis calculated for 2.60 moles of TFA. Theoretical: % C: 55.07; % H: 4.96; % N: 5.80. Observed: % C: 54.97; % H: 5.05; % N: 5.74.

EXAMPLE 5

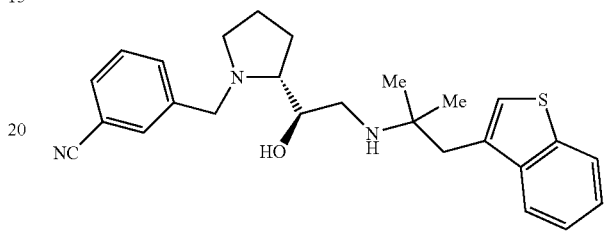

A.

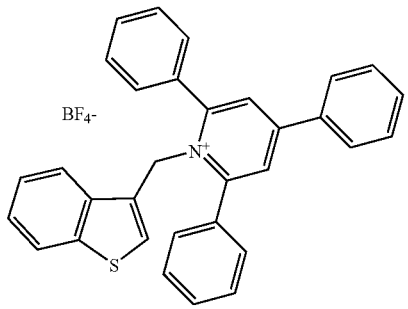

To a stirred suspension of C-Benzo[b]thiophen-3-yl-methylamine (2.0 g, 12.25 mmol) in ethanol (40 mL) was added 2,4,6-triphenylpyrylium tetrafluoroborate (4.9 g, 12.37 mmol) at room temperature under argon. The reaction mixture was stirred at room temperature for 20 h. The yellow precipitate formed was collected by filtration, washed with anhydrous ether and air-dried to give the title compound (6.2 g, 94%) as a yellow powder.

MS (ES+) m/z 454 [M+H]. $^1$H NMR (500 MHz, CD$_3$OD+ DMSO-d6): □ 5.85 (s,2H); 7.12–7.18 (m,2H); 7.21(s,1H); 7.26 (t,1H); 7.42–7.50 (m,5H); 7.60–7.72 (m,6H); 7.74–7.81 (m,2H); 7.13 (d,2H); 8.42 (s,2H); 8.52 (d,1H).

B.

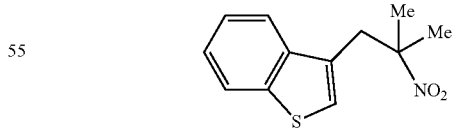

Sodium hydride (60 wt % in mineral oil, 1.38 g, 34.5 mmol) was added to anhydrous methanol (19 mL) at 0° C. under argon. The reaction mixture was stirred at 0° C. for 5 min and 2-nitropropane (3.06 g, 34.35 mmol) was added. The reaction mixture was stirred at room temperature for 30 min and concentrated to provide a white powder. To this powder, under argon, was added a solution of the Part A compound (6.2 g, 13.7 mmol) in DMSO (40 mL) at room temperature. The reaction mixture was stirred at 60° C. for 20 h, allowed to cool to room temperature and carefully quenched with water. Extraction with ethyl acetate was followed by washing with water, drying over MgSO$_4$ and concentration provided a red sticky solid. The solid was dissolved in ether (200 mL) and stirred with Amberlyst 15 ion-exchange resin (80 g) at room temperature for 20 h. The mixture was filtered and concentrated to provide the title compound (2.5 g, 93%) as a dark brown gum.

MS (ES+) m/z 253 [M+NH$_4$]. $^1$H NMR (400 MHz, CDCl$_3$): ☐ 1.63 (s, 6H); 3.50 (s,2H); 7.18 (s,1H); 7.35–7.45 (m,2H); 7.72 (d, 1H, J=7.92 Hz); 7.86 (d, 1H, J=9.92 Hz). $^{13}$C NMR (100.40 MHz, CDCl$_3$): ☐ 26.01; 38.54; 80.80; 121.61; 122.94; 124.21; 124.36; 125.55; 129.98.

C.

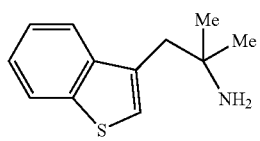

A mixture of the Part B compound (230 mg, 0.98 mmol) and Raney Nickel (50% suspension in water, 200 mg) was hydrogenated at 50 psi for 20 hr. The catalyst was filtered and the filtrate was concentrated to provide the title compound (160 mg, 80%) as a yellow gum.

MS (ES+) m/z 206 [M+H]. $^1$H NMR (400 MHz, CD$_3$OD): ☐ 1.35 (s,6H); 3.23 (s,2H); 7.36–7.46 (m,2H); 7.55 (s, 1H); 7.78–7.86 (m,2H). $^{13}$C NMR (100.40 MHz, CD$_3$OD): ☐ 23.72; 45.63; 46.22; 117.44; 117.54; 118.81; 118.95; 119.33; 135.06; 135.45; 143.23.

D.

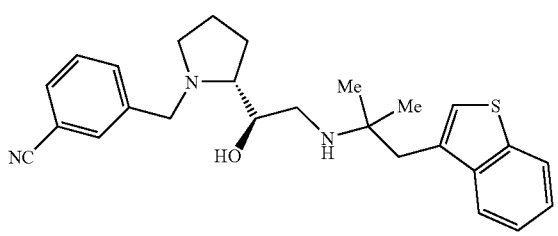

A mixture of the Part C compound, the Example 3 Part D1 compound (55 mg, 0.24 mmol), methylene chloride (0.25 mL) and 2-propanol (0.25 mL) was sonicated for 1 min and concentrated. The mixture was heated at 90° C. for 24 h. The crude reaction mixture was purified by preparative HPLC (Method 1, gradient elution 15–100% B/A over 20 min) to give the title compound (20 mg, 12%) as a white foam.

MS (ES+) m/z 434 [M+H]. $^1$H NMR (500 MHz, CD$_3$OD): ☐ 1.38 (s,3H); 1.39 (s,3H); 1.80–1.90 (m,1H); 1.98–2.08 (m,1H); 2.16–2.24 (m,1H); 2.34–2.42 (m,1H); 3.18–3.25 (m,1H); 3.293.42 (m,5H); 3.72–3.80 (m,1H); 4.18–4.22 (m,1H); 4.38 (d,1H, J=13.2 Hz); 4.92 (d,1H, J=12.1 Hz); 7.36–7.41 (m,1H); 7.43–7.60 (m,1H); 7.53 (s,1H); 7.67–7.71 (m,1H); 7.79–7.84 (m,2H); 7.88–7.96 (m,3H). $^{13}$C NMR (125.65 MHz, CD$_3$OD): ☐ 23.61; 23.71; 24.25; 28.47; 36.66; 46.08; 55.67; 60.85; 62.38; 69.36; 71.64; 114.56; 118.86; 123.24; 123.97; 125.42; 125.61; 127.60; 130.52; 131.53; 133.57; 134.787; 135.55; 136.57; 140.70; 141.68. HPLC: Retention time=2.463 min (Method A).

EXAMPLE 6

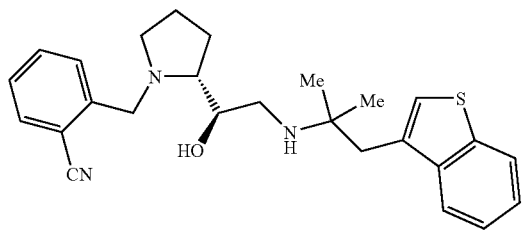

The procedure for the Example 5 Part D compound, utilizing the Example 1 Part D1 compound (70 mg, 0.3 mmol), was followed to give the title compound (38 mg, 17%) as a white foam.

MS (ES+) m/z 434 [M+H]. $^1$H NMR (500 MHz, CD$_3$OD): ☐ 1.39 (s,3H); 1.41 (s,3H); 1.88–1.96 (m,1H); 2.00–2.10 (m,1H); 2.19–2.28 (m,1H); 2.38–2.46 (m,1H); 3.28–3.48 (m,6H); 3.82–3.90 (m,1H); 4.20–4.28 (m,1H); 4.55 (d,1H, J=13.2 Hz); 5.05 (d,1H, J=13.2 Hz); 7.36–7.41 (m,1H); 7.43–7.60 (m,1H); 7.53 (s,1H); 7.67–7.71 (m,1H); 7.79–7.84 (m,2H); 7.88–7.96 (m,3H). $^{13}$C NMR (125.65 MHz, CD$_3$OD): ☐ 23.65; 23.73; 24.37; 28.39; 36.64; 46.15; 55.87; 59.38; 62.39; 69.35; 72.02; 115.47; 118.31; 123.28; 123.93; 125.40; 125.59; 127.60; 130.58; 131.97; 133.58; 134.92; 140.72; 141.67. HPLC: Retention time=2.473 min (Method A).

EXAMPLE 7

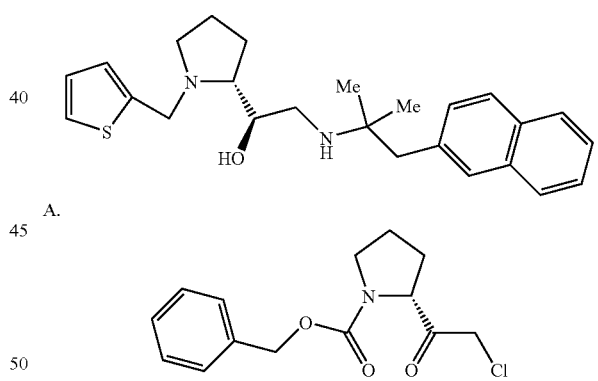

A.

To a stirred slurry of (+)-carbobenzyloxy-D-proline (10.0 g, 40.2 mmol) in dry THF (100 mL) was added N-methyl-morpholine (4.85 mL, 44.1 mmol) at room temperature under argon. The reaction mixture was cooled to −13° C. and isobutyl chloroformate (5.2 mL, 40.2 mmol) was added over 5 min. The reaction mixture was stirred at −15° C. for 5 min and filtered under nitrogen atmosphere into a cold (−15° C.) flask. The precipitate was washed with ether (15 mL). The organic layers were combined and a solution of diazomethane in ether (prepared from 18 g of 1-methyl-3-nitro-1-nitrosoguanidine in 190 mL of diethyl ether and 60 mL of 40% KOH in water, as described in Aldrichimica Acta, 1983, vol 16, page 3) was added dropwise at 0° C. The reaction mixture was stirred at room temperature for 1 h. Excess of diazomethane was removed with a gentle stream of nitrogen.

The reaction mixture was cooled to 0° C. and dry HCl was bubbled through until the disappearance of the yellow color. The reaction mixture was diluted with water and extracted with ethyl acetate (2×200 mL). The organic layer was washed successively with 10% aqueous NaHCO₃, H₂O, brine, dried over anhydrous sodium sulfate and concentrated to provide the title compound (11.0, 100%) as a colorless oil.

B.

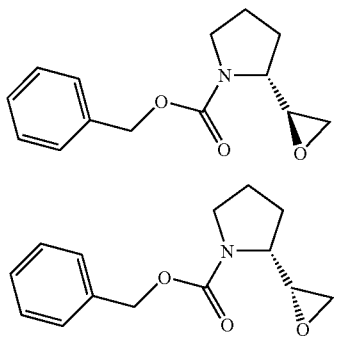

To a solution of the Part A compound (10.6 g, 37.5 mmol) in a mixture of MeOH and THF (150 mL, 1:1 v/v) at −78° C. was added sodium borohydride (3.23 g, 37.5 mmol) under argon. The reaction mixture was allowed to warm to room temperature overnight, diluted with H₂O and extracted with ethyl acetate. The organic layer was washed with aqueous NaHCO₃ and brine, dried over sodium sulfate and concentrated to provide 10.07 g of the intermediate alcohol. The alcohol was dissolved in isopropanol (140 mL) and aqueous 1N potassium hydroxide (57 mL, 57 mmol) was added. After 1 h of stirring, solvent was removed under reduced pressure and the residue was dissolved in ethyl acetate (300 mL). The organic layer was washed with water followed by brine, dried over sodium sulfate and concentrated to give 10 g of the crude product. Proton NMR (400 MHz) showed that the product was a 1:1 mixture of diastereomers. Flash chromatography on silica gel eluting with 2:3 ethyl acetate: hexanes provided compound B1 (3.5 g, 40%) and compound B2 (3.5 g, 40%) and 1.5 g of a mixture of compounds B1 and B2.

Compound B1:

MS (ES+) m/z 248 [M+H]. ¹H NMR (500 MHz, CDCl₃): δ 1.80–2.10 (m,4H); 2.40–2.70 (m,2H); 3.00–3.10 (m,1H); 3.40–3.50 (m,2H); 4.00–4.25 (m,1H); 5.10–5.20 (m,2H); 7.30–7.42 (m,5H). ¹³C NMR (125.65 MHz, CDCl₃): □ 23.50; 24.30; 28.41; 28.91; 44.31; 44.44; 46.94; 47.22; 53.89; 56.33; 66.83; 127.80; 127.94; 128.45; 136.75; 136.85; 155.55. HPLC: Retention time=2.90 min (Method D).

Compound B2:

MS (ES+) m/z 248 [M+H]. ¹H NMR (500 MHz, CDCl₃): δ 1.85–2.03 (m,4H); 2.50–3.04 (m,3H); 3.40–3.75 (m,3H); 5.06–5.20 (m,2H); 7.30–7.42 (m,5H). ¹³C NMR (125.65 MHz, CDCl₃): □ 23.17; 24.05; 27.30; 28.63; 46.75; 47.18; 47.45; 47.64; 52.51; 52.92; 58.49; 59.09; 66.75; 67.13; 127.79; 127.90; 128.23; 128.47; 136.45; 136.72; 154.55.

HPLC: Retention time=2.84 min (Method D).

C.

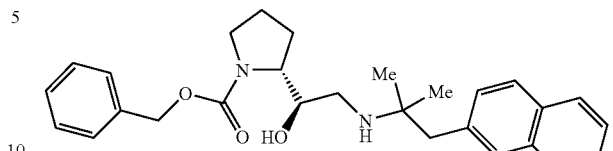

A mixture of the Part B1 compound (1.86 g, 7.50 mmol) and 1,1-dimethyl-2-(2-naphthyl)ethylamine (1.50 g, 7.50 mmol) was heated at 90° C. in a pressure tube under argon for 8 h. The reaction mixture was cooled to room temperature then purified by silica gel flash chromatography eluting with a step gradient of methanol in dichloromethane to give the title compound (1.80 g, 55%) as a white solid.

MS (ES+) m/z 447 [M+H]. ¹H NMR (400 MHz, CDCl₃): δ 0.84–1.20 (m,6H); 1.72–2.10 (m,5H); 2.45–3.00 (m,4H); 3.30–3.70 (m,3H); 4.00–4.10 (m,1H); 5.10–5.20 (m, 2H); 7.20–7.85 (m, 12H). HPLC: Retention time=3.06 min (Method D).

D.

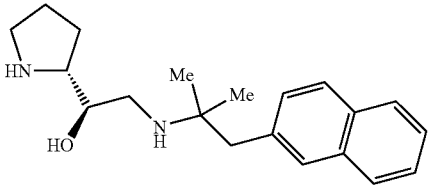

A mixture of the Part C compound (1.80 g, 4.0 mmol), palladium acetate (170 mg, 0.76 mmol), and 5% palladium on activated carbon (450 mg) in ethanol (30 mL) was stirred under an atmosphere of hydrogen for 2 h. The reaction mixture was filtered through Celite and washed successively with 2N ammonia in methanol, triethylamine, and dichloromethane to give 1.05 g (83%) of the title compound as a white sticky solid.

MS (ES+) m/z 313 [M+H]. ¹H NMR (400 MHz, CDCl₃): δ 1.15–1.50 (m, 7H); 1.70–2.00 (m, 3H); 2.80–3.10 (m, 10H); 3.50–4.00 (m, 2H); 4.20–4.40 (m, 3H); 7.32 (d, 1H, J=9 Hz); 7.20–7.50 (m, 2H); 7.65 (s, 1H); 7.66–8.10 (m, 3H). HPLC: Retention time=2.39 min (Method E).

E.

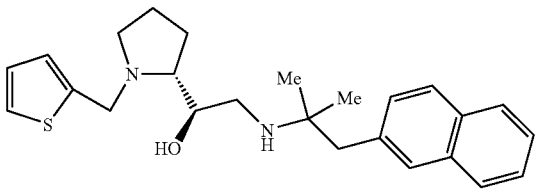

To a solution of 2-thiophenecarboxaldehyde (4.5 mg, 0.04 mmol) in a 1:1 solution of methanol and THF (100 μL) under argon were added successively a solution of the Part D compound (4.7 mg, 0.015 mmol) in 1:1 methanol/THF (100 μL) and a solution of titanium isopropoxide in THF (50 μL, 0.4 M, 0.02 mmol). After 4 h of stirring, a solution of sodium cyanoborohydride in THF (50 µL, 1M, 0.05 mmol) was added and stirring continued for 16 h. Aqueous 1N HCl (200 µl) was added and the mixture was applied to a cation exchange resin cartridge, and washed with methanol (2×3 mL). Elution with 1.5 mL of a solution of ammonia in methanol (3.5N), followed by concentration under reduced pressure provided the title compound (4.5 mg, 73%) as a white foam.

MS (ES+) m/z 409 [M+H].

Alternative Synthesis of the Example 7 Part B1 Compound

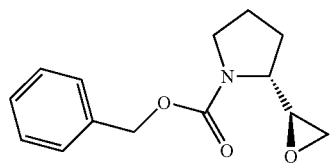

A mixture of (+)-carbobenzyloxy-D-proline (50 g, 200.6 mmol) and chlorotrimethylsilane (25.5 mL, 200.6 mL) in dry MeOH (600 mL) was stirred at room temperature overnight (~18 h), then concentrated in vacuo at room temperature to provide a colorless oil. Toluene (300 mL) was added and the mixture was concentrated to provide a colorless oil (53 g), which was utilized without further purification.

A mixture of the methyl ester prepared above (52 g) and chloroiodomethane (57.5 mL, 790 mmol) in anhydrous THF (1000 mL) was cooled to −78° C. and a solution of LDA (395 mL, 2.0M in THF, 790 mmol) was added dropwise at such a rate to maintain the reaction temperature ≦−70° C. Upon completion of addition, the reaction mixture was stirred at −78° C. for 1 h, then quenched by addition of a solution of AcOH/THF (1:1, 230 mL) at such a rate to maintain the reaction temperature <−70° C. The reaction mixture was gradually warmed to room temperature, followed by addition of brine (1.2 L). The mixture was extracted with EtOAc (3×800 mL), and the combined organic extracts were washed with saturated $NaHCO_3$, 5% $NaHSO_3$, and brine, then dried over $Na_2SO_4$. Evaporation of the solvent provided a brown oil, which was purified by passing through a plug of silica gel (1 kg), eluting with a step gradient of 25% EtOAc/hexane to 30% EtOAc/hexane, to provide the chloromethyl ketone (35 g, 62%, two steps) as a colorless oil.

A solution of the chloromethyl ketone prepared above (35 g, 124 mmol) in anhydrous THF (2 L) was cooled to −78° C., and a solution of L-Selectride (186 mL, 1.0M in THF, 186 mmol) was added dropwise at such a rate to maintain the reaction temperature ≦−68° C. Upon completion of addition, the reaction mixture was stirred at −78° C. for 45 min. Acetic acid (21.4 mL) was added, followed by LiOH monohydrate (26.8 g) and $H_2O_2$ (30%, 560 mL). After warming to room temperature, the majority of the THF was removed in vacuo from the reaction mixture. The resulting slurry was diluted with brine and extracted with EtOAc (3×750 mL). The combined organic extracts were washed with 1N HCl and brine, then dried over $Na_2SO_4$. Evaporation provided the alcohol (36.2 g) as an oil, which was utilized without further purification.

To a stirred solution of the alcohol (36 g) prepared above in isopropyl alcohol (1.1 L) was added 1N aqueous KOH (360 mL). The mixture was stirred at room temperature for 30 min, then the organic solvent was removed in vacuo at room temperature. The resulting slurry was diluted with saturated NaHCO3 and extracted with EtOAc (3×750 mL). The combined organic extracts were washed washed with brine and dried over MgSO4. The resulting oil was purified by flash chromatography on silica gel (1 kg), eluting with a step gradient of 25% EtOAc/hexane to 30% EtOAc/hexane, to provide the title compound (25.4 g, 83%, two steps) as a colorless oil.

General Procedure 1

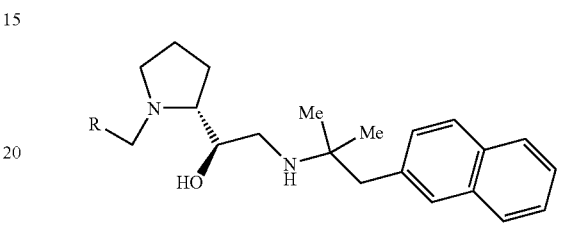

To a solution/suspension of the appropriate aldehyde (40 µmol) in a 1:1 solution of methanol and THF (100 µL) under argon were added successively a solution of the Example 7 part D compound (4.7 mg, 15 µmol) in 1:1 methanol/THF (100 µL) and a solution of the appropriate Lewis acid (50 µL of 0.5M zinc chloride in THF or 50 µL of 0.4M titanium isopropoxide in THF). After 4 h of stirring, 50 µL of a 1M solution of sodium cyanoborohydride in THF was added and stirring continued for 16 h. Aqueous HCl (200 µL, 1N) was added and the mixture was applied to a cation exchange resin cartridge, and washed with methanol (2×3 mL). Elution with 1.5 mL of a solution of ammonia in methanol (3.5N), followed by concentration under reduced pressure provided the title compounds indicated in the following table. Compounds with less than 70% HPLC purity were purified by preparative HPLC (Method 5, gradient elution 30–100% B/A over 8 min).

Examples 8 to 107 set out in Table 1 were prepared by employing the General Procedure 1 described above.

TABLE 1

| Example No. | R | [M + H]⁺ |
|---|---|---|
| 8 |  (2-methylphenyl) | 417 |
| 9 |  (5-ethylfuryl) | 421 |

TABLE 1-continued

[Structure: R-CH2-pyrrolidine-CH(OH)-CH2-NH-C(Me)2-CH2-naphthalene]

| Example No. | R | [M + H]+ |
|---|---|---|
| 10 | 2-methoxyphenyl | 433 |
| 11 | 5-(HO2C)-furan-2-yl | 437 |
| 12 | 2,3-difluorophenyl | 439 |
| 13 | 2,6-difluorophenyl | 439 |
| 14 | 2,4-difluorophenyl | 439 |
| 15 | 3-nitrophenyl | 448 |
| 16 | 2-fluoro-6-chlorophenyl | 455 |
| 17 | 2-(CO2Me)phenyl | 461 |

TABLE 1-continued

[Structure: R-CH2-pyrrolidine-CH(OH)-CH2-NH-C(Me)2-CH2-naphthalene]

| Example No. | R | [M + H]+ |
|---|---|---|
| 18 | 2-(OCHF2)phenyl | 469 |
| 19 | 2-(CF3)phenyl | 471 |
| 20 | 2,6-dichlorophenyl | 471 |
| 21 | 3-HO-4-MeO-5-MeO-phenyl | 477 |
| 22 | 2-bromophenyl | 481 |
| 23 | 3-nitro-4-chlorophenyl | 482 |
| 24 | 4-bromothien-2-yl | 489 |
| 25 | 2-fluoro-3-(CF3)phenyl | 489 |

TABLE 1-continued

[Structure: pyrrolidine-N-CH2-R with CH(OH)-CH2-NH-C(Me)2-CH2-(2-naphthyl)]

| Example No. | R | [M + H]+ |
|---|---|---|
| 26 | 4-hydroxy-3-methoxy-2-nitrophenyl (HO, OMe, NO2 substituted phenyl) | 494 |
| 27 | 4-bromo-2-fluorophenyl | 499 |
| 28 | 5-(3-nitrophenyl)furan-2-yl | 514 |
| 29 | 2-iodophenyl | 529 |
| 30 | 1-(phenylsulfonyl)pyrrol-2-yl | 532 |
| 31 | 4-ethyl-3-methyl-5-(benzyloxycarbonyl)-1H-pyrrol-2-yl | 568 |

TABLE 1-continued

[Same core structure]

| Example No. | R | [M + H]+ |
|---|---|---|
| 32 | 1-(4-methylphenylsulfonyl)-1H-indol-3-yl | 596 |
| 33 | 5-bromo-2-ethoxyphenyl | 525 |
| 34 | 2,3,4-trifluorophenyl | 457 |
| 35 | 4,5-dibromothien-2-yl | 567 |
| 36 | 2,4,6-trifluorophenyl | 457 |
| 37 | 2-benzyloxy-3-methoxyphenyl | 539 |
| 38 | 5-bromofuran-2-yl | 471 |

TABLE 1-continued

[Structure: R-CH2-N(pyrrolidine)-CH(OH)-CH2-NH-C(Me)(Me)-CH2-naphthalene]

| Example No. | R | [M + H]+ |
|---|---|---|
| 39 | 4-(MeO2S)-phenyl | 481 |
| 40 | 5-methylfuran-2-yl | 407 |
| 41 | 2,5-dimethoxyphenyl (MeO at 5, OMe at 2) | 463 |
| 42 | 2,3,4-trifluorophenyl | 457 |
| 43 | thiazol-2-yl | 410 |
| 44 | 3-nitro-4-methylphenyl | 462 |
| 45 | 2-nitro-3-methoxyphenyl | 478 |
| 46 | 2-hydroxyphenyl | 419 |
| 47 | 2-chloro-3,4-dimethoxyphenyl | 497 |
| 48 | 2-chloro-5-(trifluoromethyl)phenyl | 505 |
| 49 | 4-methylphenyl | 417 |
| 50 | 3-hydroxyphenyl | 419 |
| 51 | 3-fluorophenyl | 421 |
| 52 | 5-methylthiophen-2-yl | 423 |
| 53 | 2-chlorophenyl | 437 |

TABLE 1-continued

| Example No. | R | [M + H]+ |
|---|---|---|
| 54 | 3-chlorophenyl | 437 |
| 55 | 4-chlorophenyl | 437 |
| 56 | 3,4-difluorophenyl | 439 |
| 57 | 2-fluorophenyl | 421 |
| 58 | 3-methyl-2-hydroxyphenyl | 433 |
| 59 | 3-fluoro-2-hydroxyphenyl | 437 |
| 60 | 3,5-difluorophenyl | 439 |
| 61 | 4-nitrophenyl | 448 |
| 62 | 2-nitro-5-hydroxyphenyl | 464 |
| 63 | 3,5-dichloro-4-hydroxyphenyl | 487 |
| 64 | 5-bromothiophen-2-yl | 489 |
| 65 | 4-[(furan-2-ylmethyl)thio]-3-nitrophenyl | 560 |
| 66 | 4-(benzylthio)-3-nitrophenyl | 570 |
| 67 | pentafluorophenyl | 493 |

TABLE 1-continued

| Example No. | R | [M + H]+ |
|---|---|---|
| 68 | 4-Cl, 2-NO2-phenyl | 482 |
| 69 | 2-Cl-quinolin-3-yl | 488 |
| 70 | 3-Me-thiophen-2-yl | 423 |
| 71 | quinolin-3-yl | 454 |
| 72 | 4-F, 3-NO2-phenyl | 466 |
| 73 | 3-NO2, 4-OH, 5-OMe-phenyl | 494 |
| 74 | 3-NO2, 4-piperidin-1-yl-phenyl | 531 |
| 75 | 3-NO2, 4-morpholin-4-yl-phenyl | 533 |
| 76 | 3-NO2, 4-(4-Cl-phenoxy)-phenyl | 575 |
| 77 | 3-NO2, 4-(3-CF3-phenoxy)-phenyl | 608 |
| 78 | 3-NO2, 4-[4-(2-OMe-phenyl)-piperidin-1-yl]-phenyl | 637 |
| 79 | 2-CN, 3-F, 6-NMe2-phenyl | 489 |
| 80 | 3-CN, 4-F-phenyl | 446 |
| 81 | 2-Cl, 6-OMe-quinolin-3-yl | 519 |
| 82 | 3-NO2, 4-Cl-phenyl | 483 |
| 83 | 4-(2-hydroxyethoxy)-phenyl | 463 |
| 84 | 2-F, 6-OMe-phenyl | 451 |

TABLE 1-continued
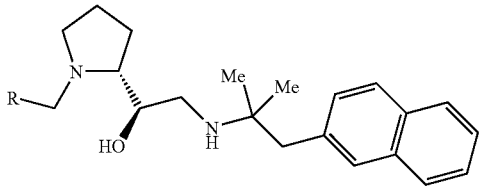
| Example No. | R | [M + H]+ |
|---|---|---|
| 85 | 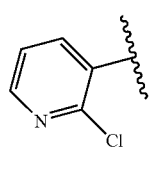 | 404 |
| 86 | 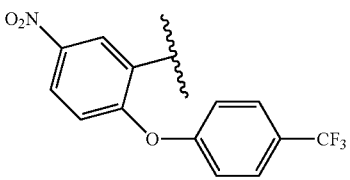 | 439 |
| 87 | 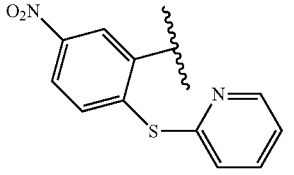 | 608 |
| 88 | 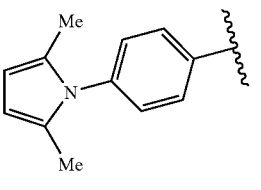 | 557 |
| 89 | 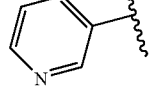 | 496 |
| 90 | 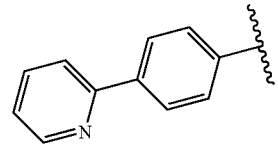 | 404 |
| 91 | 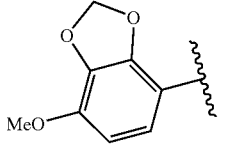 | 480 |
| 92 | 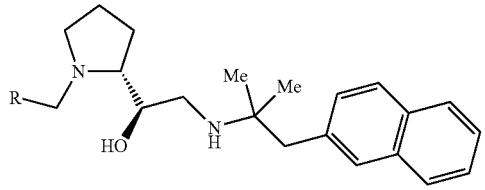 | 477 |
TABLE 1-continued
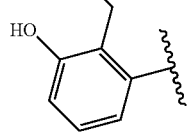
| Example No. | R | [M + H]+ |
|---|---|---|
| 93 | 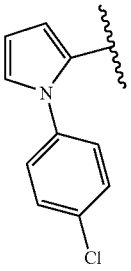 | 459 |
| 94 | 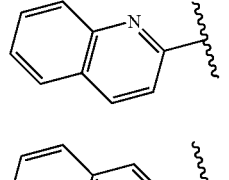 | 503 |
| 95 | 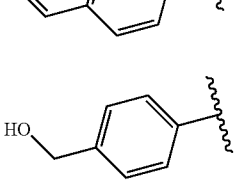 | 454 |
| 96 | 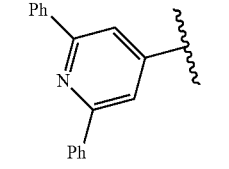 | 453 |
| 97 | 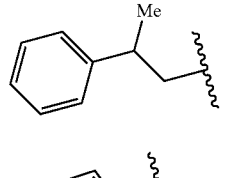 | 433 |
| 98 | 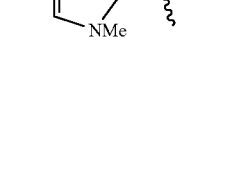 | 556 |
| 99 | 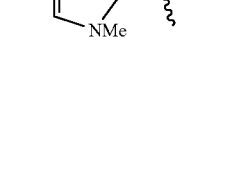 | 431 |
| 100 | 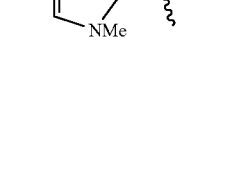 | 406 |

TABLE 1-continued

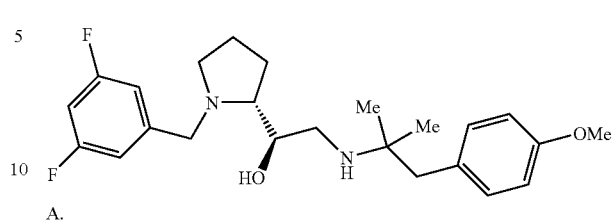

| Example No. | R | [M + H]+ |
|---|---|---|
| 101 | (pyrazole-thiophene with MeN, F3C) | 557 |
| 102 | (MeO-naphthyl) | 483 |
| 103 | (bithiophene) | 491 |
| 104 | (Cl-phenyl-NH2) | 453 |
| 105 | (Ph-CH(Me)-CH2-) | 445 |
| 106 | (F-phenyl-C(O)-pyrrole-NMe) | 528 |
| 107 | (methylenedioxy-benzofused with Me) | 489 |

EXAMPLE 108

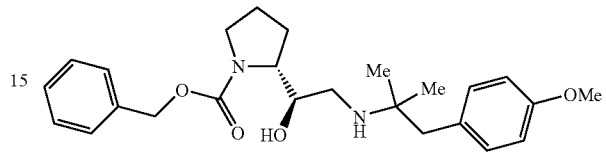

A.

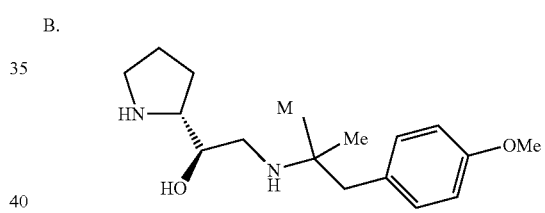

According to the procedure for the preparation of the Example 7 Part C compound, the Example 7 Part B1 compound (2.21 g, 8.90 mmol) and 2-(4-methoxyphenyl)-1,1-dimethylethylamine (1.60 g, 8.94 mmol) were coupled to give the title compound (1.63 g, 45%) as a colorless gum.

MS (ES+) m/z 427 [M+H]. $^1$H NMR (400 MHz, CDCl$_3$): δ 1.00–1.20 (m,6H); 1.75–2.20 (m,4H); 2.45–2.80 (m,3H); 3.30–3.90 (m,8H); 4.00–4.10 (m, 1H); 4.20–4.40 (m, 1H); 5.10–5.20 (m, 2H); 6.82 (d, 2H, J=7 Hz); 7.07 (d, 2H, J=7 Hz); 7.30–7.40 (m, 5H). HPLC: Retention time=2.92 min (Method D).

B.

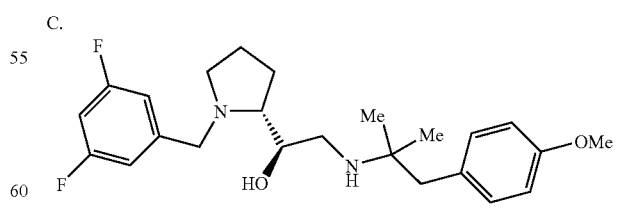

According to the procedure for the preparation of the Example 7 Part D compound, the Part A compound (1.58 g, 3.70 mmol) was hydrogenolyzed to give the title compound (1.12 g, 100%) as a light brown oil.

MS (ES+) m/z 293 [M+H]. $^1$H NMR (400 MHz, CDCl$_3$): δ 1.00–1.50 (m, 6H); 1.60–2.10 (m, 3H); 2.75–2.90 (m, 5H); 3.00–3.20 (m, 1H); 3.30–3.90 (m, 5H); 4.20–4.40 (m, 1H); 4.60–5.00 (m, 3H); 6.83 (d, 1H, J=8 Hz); 7.10 (d, 1H, J=8 Hz); HPLC: Retention time=1.78 min (Method E).

C.

According to the procedure for the preparation of the Example 7 compound, the Part B compound (4.4 mg, 0.015 mmol) was reacted with 3,5-difluorobenzaldehyde to give the title compound (4.0 mg, 64%) as a white foam.

MS (ES+) m/z 419 [M+H].

Examples 109 to 122 set out in Table 2 were prepared by employing the General Procedure 1 utilizing the Example 108 Part B compound.

TABLE 2

| Example No. | R | [M + H]⁺ |
|---|---|---|
| 109 | 3-hydroxy-4-nitrophenyl | 444 |
| 110 | 2,4,5-trifluorophenyl | 437 |
| 111 | 2-chloroquinolin-3-yl | 468 |
| 112 | 4-fluoro-2-nitrophenyl | 446 |
| 113 | 3-methylthien-2-yl | 403 |
| 114 | 4-(furan-2-ylmethylthio)-3-nitrophenyl | 540 |
| 115 | quinolin-3-yl | 434 |
| 116 | 4-chloro-3-nitrophenyl | 463 |
| 117 | 4-methyl-3-nitrophenyl | 442 |

TABLE 2-continued

| Example No. | R | [M + H]⁺ |
|---|---|---|
| 118 | 3-methyl-4-(4-isopropylphenyl)butyl | 467 |
| 119 | 3-phenyl-1H-pyrazol-4-yl | 449 |
| 120 | 6,8-dimethyl-4-oxo-4H-chromen-3-yl | 479 |
| 121 | 5-(1-methyl-5-trifluoromethyl-1H-pyrazol-3-yl)thien-2-yl | 537 |
| 122 | 1H-indol-3-yl | 422 |

EXAMPLE 123

A.

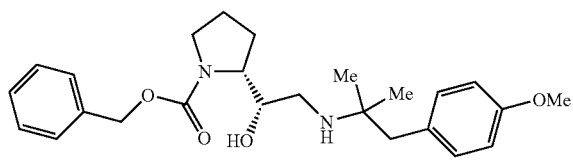

According to the procedure for the preparation of the Example 7 Part C compound, the Example 7 Part B2 compound (1.10 g, 4.50 mmol) and 2-(4-methoxyphenyl)-1,1-dimethylethylamine (0.8 g, 4.47 mmol) were coupled to give the title compound (1.35 g, 71%) as a colorless gum.

MS (ES+) m/z 427 [M+H]. $^1$HNMR (400 MHz, CDCl$_3$): δ 1.00–1.20 (m,6H); 1.75–2.20 (m,4H); 2.45–2.80 (m,3H); 3.30–3.70 (m,5H); 3.80–4.00 (m, 4H); 5.10–5.20 (m, 2H); 6.82 (d, 2H, J=7 Hz); 7.07 (d, 2H, J=7 Hz); 7.30–7.40 (m, 5H). HPLC: Retention time=2.92 min (Method D).

B.

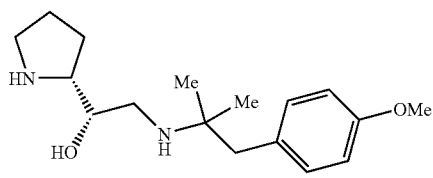

According to the procedure for the preparation of the Example 7 Part D compound, the Part A compound (0.8 g, 2.10 mmol) was hydrogenolyzed to give the title compound (0.55 g, 100%) as a light brown oil.

MS (ES+) m/z 293 [M+H]. $^1$HNMR (400 MHz, CDCl$_3$): δ 1.04 (s, 3H); 1.13 (s, 3H); 1.50–2.0 (m, 1H); 2.50–3.10 (m, 7H); 3.00–3.20 (m, 1H); 3.79 (s, 3H); 4.20–4.40 (m, 3H); 6.85 (d, 1H, J=9 Hz); 7.09 (d, 1H, J=9 Hz); HPLC: Retention time=1.84 min (Method E).

C.

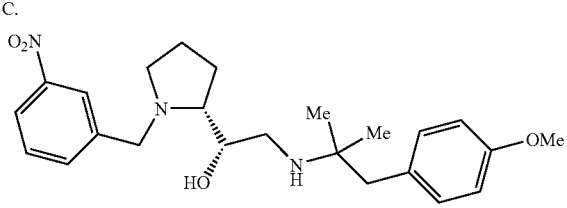

According to the procedure for the preparation of the Example 7 compound, the Part B compound (4.4 mg, 0.015 mmol) was reacted with 3-nitrobenzaldehyde to give the title compound (5.6 mg, 87%) as a white foam.

MS (ES+) m/z 428 [M+H].

Examples 124 to 133 set out in Table 3 were prepared by employing the General Procedure 1 utilizing the Example 123 Part B compound.

TABLE 3

| Example No. | R | [M + H]+ |
|---|---|---|
| 124 | 5-chloro-2-hydroxyphenyl | 433 |
| 125 | 2-methylphenyl | 397 |
| 126 | 2-bromophenyl | 461 |
| 127 | 2-chloroquinolin-3-yl | 468 |
| 128 | 5-bromothien-2-yl | 469 |
| 129 | 4-(benzylthio)-3-nitrophenyl | 550 |
| 130 | 4-(furan-2-ylmethylthio)-3-nitrophenyl | 540 |
| 131 | quinolin-3-yl | 434 |
| 132 | 4-chloro-3-nitrophenyl | 463 |

TABLE 3-continued

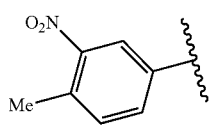

| Example No. | R | [M + H]+ |
|---|---|---|
| 133 | (O2N, Me-substituted phenyl group) | 442 |

EXAMPLE 134

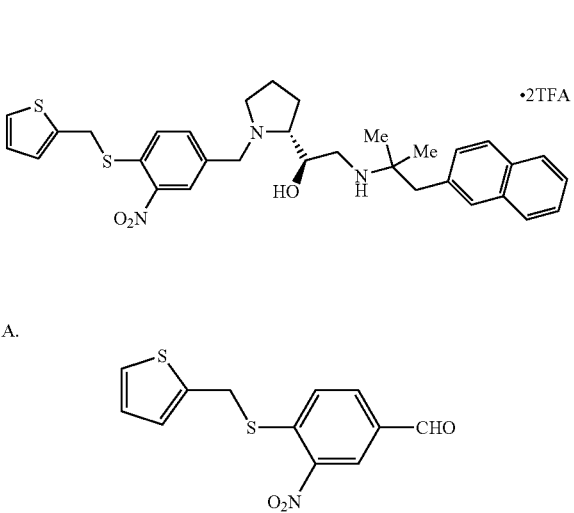

A.

(structure: 2-thienylmethylthio-nitro-benzaldehyde)

To a clear, slightly yellow solution of 4-fluoro-3-nitrobenzaldehyde (100 mg, 0.59 mmol) in dimethylformamide (2 mL) was added triethylamine (0.25 mL, 1.77 mmol) and 2-thenylmercaptan (72 µL, 0.89 mmol). The resulting clear, dark yellow solution was stirred at room temperature for 15 min. The reaction was cooled to 0° C. and water (5 mL) was added giving a milky yellow suspension. Dichloromethane (10 mL) was added resulting in a biphasic mixture. The layers were separated and the organic layer was washed with brine (5 mL), dried over $Na_2SO_4$, filtered and concentrated to give an orange residue weighing 184 mg. Purification by flash chromatography eluting with 3:1 hexane:ethyl acetate gave the title compound (134 mg, 81%) as a yellow solid.

HRMS m/z calc'd for $C_{12}H_8NO_3S_2$[M–H]: 277.9946. Found 277.9953. $^1$H NMR (400 MHz, DMSO-$d_6$): δ 4.76 (s, 2H); 6.99 (dd, J=5.3, 3.5 Hz, 1H); 7.19 (d, J=3.5 Hz, 1H); 7.46 (dd, J=5.3, 0.9 Hz, 1H); 7.97 (d, J=8.4 Hz, 1H); 8.13 (dd, J=8.4, 1.8 Hz, 1H); 8.69 (d, J=1.8 Hz, 1H); 10.04 (s, 1H). $^{13}$C NMR (100 MHz, DMSO-$d_6$): δ 30.69; 126.23; 127.05; 127.10; 127.82; 128.16; 132.53; 132.85; 137.74; 143.03; 145.17; 190.90.

B.

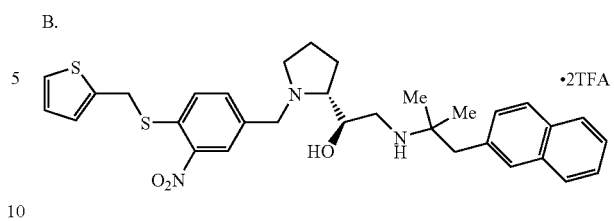

According to the procedure described in Example 7, the Part A compound (21 mg, 0.075 mmol) was reacted to provide the title compound (14 mg, 58%).

MS (ES+) m/z 576.3 [M+H]+.

Examples 135 to 157 set out in Table 4 were prepared by employing the general procedure described above in Example 34, and utilizing the appropriate 3-substituted-4-fluorobenzaldehyde and the appropriate thiol, amine, or alkoxide.

TABLE 4

(general structure with R-X, Y substituents on pyrrolidine-naphthalene scaffold)

| Example No. | R | X | Y | [M + H]+ |
|---|---|---|---|---|
| 135 | 4-bromophenyl | S | NO2 | 636.2 |
| 136 | pyrazinylmethyl | S | NO2 | 572.4 |
| 137 | pyrazinylmethyl | S | CN | 552.4 |
| 138 | HO-CH2CH2- | S | NO2 | 524.4 |
| 139 | HO-CH(Me)-CH2- | S | NO2 | 538.4 |
| 140 | HO-CH(Me)-CH2- | S | CN | 518.4 |
| 141 | MeO2C-CH2- | S | NO2 | 552.3 |

TABLE 4-continued

| Example No. | R | X | Y | [M + H]⁺ |
|---|---|---|---|---|
| 142 | MeO₂C- | S | CN | 532.4 |
| 143 | MeHN-C(O)- | S | NO₂ | 551.4 |
| 144 | MeHN-C(O)- | S | CN | 531.4 |
| 145 | 2-pyridyl-CH₂- | S | NO₂ | 571.4 |
| 146 | 2-pyridyl-CH₂- | S | CN | 551.4 |
| 147 | cyclohexyl- | S | NO₂ | 562.4 |
| 148 | 2-pyridyl- | S | NO₂ | 557.4 |
| 149 | 5-CF₃-2-pyridyl- | S | NO₂ | 625.4 |
| 150 | 4-Me-C₆H₄- | S | NO₂ | 570.4 |
| 151 | 4-Cl-C₆H₄- | S | NO₂ | 590.4 |
| 152 | Et | S | NO₂ | 508.4 |
| 153 | 2-furyl-CH₂- | S | CN | 540.4 |
| 154 | 2-furyl-CH₂- | NH | CN | 523.5 |
| 155 | Me | NH | CN | 457.5 |
| 156 | 2-furyl-CH₂- | O | NO₂ | 544.4 |
| 157 | 2-furyl-CH₂- | NH | NO₂ | 543.4 |

EXAMPLE 158

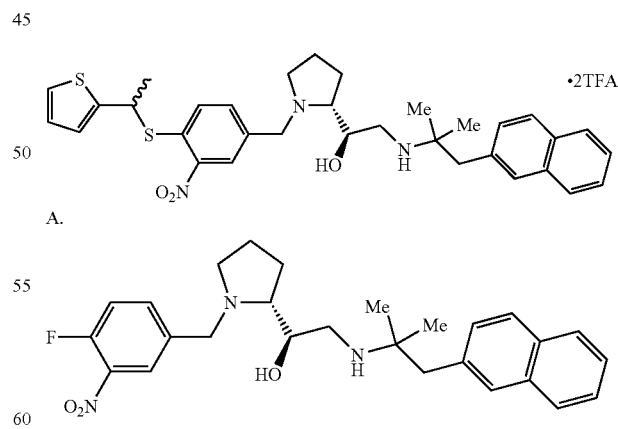

A.

According to the procedure in Example 7, reductive amination of 4-fluoro-3-nitrobenzaldehyde with the Example 7 Part D compound provided the title compound (38 mg, 26%) as a yellow-orange oil.

MS (ES+) m/z 466.3 [M+H]⁺.

B.

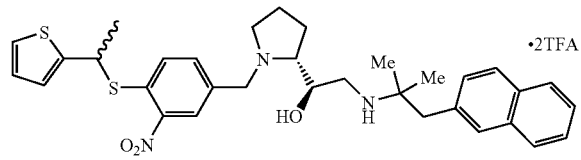

To a clear orange-yellow solution of the Part A compound (16 mg, 0.034 mmol) in dimethylformamide (0.34 mL) was added triethylamine (24 μL, 0.17 mmol) and 1-(2'-thienyl) ethyl mercaptan (21.5 μL, 0.17 mmol). After 8.5 h, excess solvent was removed in vacuo. The resulting residue was purified by preparative HPLC (Method 2, gradient elution 30–100% B/A over 10 min) to give the title compound (13.6 mg, 88% pure). The product was repurified by preparative HPLC (Method 3, gradient elution 50–100% B/A over 20 min) to give the title compound (9.7 mg, 35%) as a clear yellow gum.

HRMS m/z calc'd for $C_{33}H_{40}N_3O_3S_2$ [M+H]$^+$: 590.2511. Found 590.2491.

EXAMPLE 159

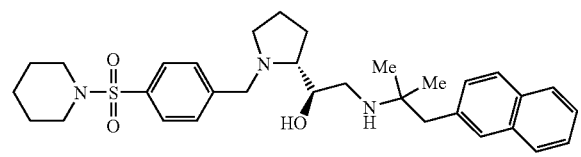

A.

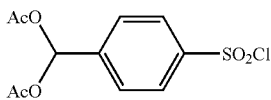

A mixture of of p-toluenesulfonylchloride (1.71 g, 8.97 mmol), acetic acid (14.2 mL) and acetic anhydride (14.2 mL) was cooled to 0° C. of Concentrated sulfuric acid (2.15 g) followed by powdered $CrO_3$ (2.5 g, 25 mmol) were introduced while the temperature was maintained below 10° C. The mixture was stirred at that temperature for an additional 0.5 h and quenched with ice, resulting in a white precipitate. The aqueous phase was extracted with cold 1,2-dichloroethane. Evaporation of the solvent gave a mixture of the target compound together with the starting material and 4-chlorosulfonylbenzoic acid. The crude product was triturated with acetone/petroleum ether (1:9), followed by filtration. The filtrate was concentrated to provide the title compound (896 mg, 33%) as a semi-crystalline oil.

$^1$H NMR (400 MHz, CDCl$_3$): □ 2.14 (s, 6H); 7.71 (s, 1H) 7.75 (d, 1H, J=8.4 Hz); 8.06 (d, 2H, J=8.4 Hz). $^{13}$C NMR (400 MHz, CDCl$_3$): □ 20.74; 88.22; 127.38; 128.19; 142.61; 145.3; 168.51.

B.

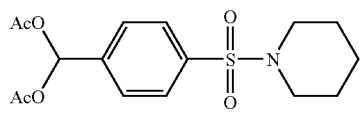

To a mixture of the Part A compound (451 mg, 1.47 mmol) and acetone (2.5 mL) was added dropwise piperidine (252 mg, 2.96 mmol) in acetone (1.5 mL). A white precipitate formed immediately. The mixture was stirred at room temperature for 1 h. The solvent was evaporated and CH$_2$Cl$_2$ (5 mL) was added. The organic phase was washed 1N HCl (2×5 mL) and water (5 mL), dried over MgSO$_4$ and concentrated in vacuo to give 526 mg of an oil. The crude product was used in the next step without further purification.

$^1$H NMR (400 MHz, CD$_3$OD): □ 1.38 (m, 2H); 1.56 (m, 4H); 2.12 (s, 6H); 2.93 (m, 2H); 7.71 (s, 1H); 7.74 (d, 2H, J=8.04 Hz); 7.80 (d, 2H, J=8.04 Hz). $^{13}$C NMR (400 MHz, CD$_3$OD): □ 20.69; 24.31; 26.22; 48; 89.78; 128.48; 129; 138.69; 141.5; 170.18. MS (ES+) m/z 356 [M+H].

C.

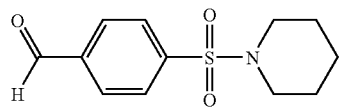

The Part B compound (525.7 mg, 1.48 mmol) was mixed with EtOH (2 mL), water (2 mL), and concentrated H$_2$SO$_4$ (200 μL). The solution was refluxed for 1 h. Upon cooling, a precipitate formed, which was filtered, rinsed with water and EtOH to provide the title compound (179 mg, 48%) as a white solid.

$^1$H NMR (400 MHz, CDCl$_3$): □ 1.44 (m, 2H); 1.59–1.67 (m, 4H); 3.02–3.05 (m, 4H); 2.93 (m, 2H); 7.92 (d, 2H, J=8.08 Hz); 8.04 (d, 2H, J=8.08 Hz); 10.12 (s, 1H) $^{13}$C NMR (400 MHz, CDCl$_3$): □ 23.44; 25.16; 46.93; 128.22; 130.04; 190.84. MS (ES+) m/z 254 [M+H].

D.

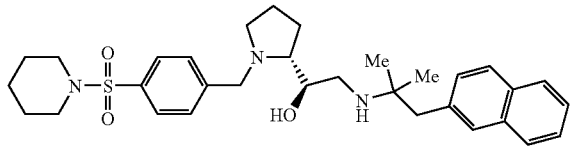

To a mixture of the Example 7 Part D compound (92.8 mg, 0.314 mmol) and THF/MeOH (1:1, 3 mL) was added the Part C compound (156.4 mg, 0.62 mmol). To the homogenous mixture was added titanium(IV) isopropoxyde (203 μL, 0.68 mmol) and the reaction was stirred for 4 h at room temperature. Sodium cyanoborohydride solution (0.68 mL, 1.0 M in THF, 0.68 mmol) and the reaction mixture was stirred for an additional 1 h at room temperature. The reaction was quenched with 1N HCl (2 mL) and the mixture stirred overnight. The heterogeneous media was loaded in a UCT CUBCX 1 HL 10M 75 cartridge and filtered by gravity. The resin was washed with 7N NH$_3$/MeOH solution. The eluent was concentrated and further purified by preparative HPLC (Method 2, gradient elution 35–100% B/A over 25 min) to give title compound (17 mg, 7%) as the bis-TFA salt.

$^1$H NMR (400 MHz, CD$_3$OD): □ 1.39 (s, 3H); 1.40 (s, 3H); 1.44 (m, 2H); 1.63 (m, 4H); 1.87 (m, 1H); 2.06 (m, 1H); 2.18 (m, 1H); 2.39 (m, 1H); 2.99 (m, 4H); 3.15–3.45(m, 5H); 3.78 (m, 1H); 3.98 (s, 1H); 4.19 (t, 1H, J=7 Hz); 4.39 (d, 1H, J=7 Hz); 4.93 (d, 1H, J=12.9 Hz); 7.4 (d, 1H, J=8.6 Hz); 7.5 (m, 2H); 7.78–7.89 (m, 8H). $^{13}$C NMR (400 MHz, CD$_3$OD): □ 26.29; 26.44; 27.18; 27.39; 29.27; 31.5; 47.7;

49; 58; 58.8; 64.04; 65.16; 72.22; 74.62; 130.14; 130.39; 131.57; 131.64; 132.14; 132.43; 132.58; 133.66; 135.75; 136.19; 137.04; 137.73; 139.55; 142.55. MS (ES+) m/z 550.4 [M+H]. HPLC retention time=4.40 min (Method F).

EXAMPLE 160

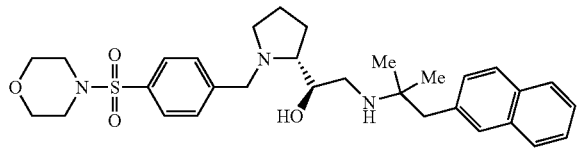

The title compound was prepared according to the procedure for Example 159.

MS (ES+) m/z 552.4 [M+H]. HPLC retention time=3.83 min (Method F).

EXAMPLE 161

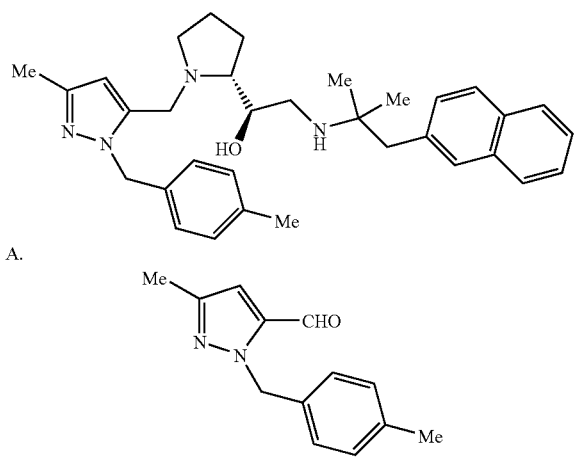

A.

3-Methyl-1H-pyrazole-5 carboxylic acid ethyl ester (617 mg, 4 mmol) and potassium carbonate (829 mg, 6 mmol) were mixed in dry DMF (10 mL) at room temperature and stirred for 30 min. 4-Methylbenzyl bromide (755 mg, 4.08 mmol) was added and the reaction mixture was heated to 50° C. for 4 h. The reaction was cooled to room temperature and 30 mL of water was added. The solution was extracted with 2×20 mL ethyl acetate. The combined organic extracts were washed with 15 mL portions of water and brine, then dried over MgSO$_4$. The mixture was filtered and the filtrate concentrated to an oil, which was purified by silica gel flash chromatography elution with 3% ethyl acetate in hexanes to provide 390 mg of the alkylated product as a colorless oil.

The alkylated product was dissolved in 10 mL of dry tetrahydrofuran at room temperature. A solution of LiAlH$_4$ in THF (1.5 mL, 1M, 1.5 mmol) was added. The reaction was stirred at room temperature for 1 h. Sodium sulfate decahydrate was added to quench excess hydride and the resulting suspension was filtered through Celite and washed with ethyl acetate. The filtrate was concentrated to afford 313 mg (96%) of the alcohol product as a white solid.

The alcohol was dissolved in 20 mL dioxane, to which manganese (IV) oxide (1.0 g, 7.69 mmol) was added. The reaction mixture was heated to reflux for 2 days, at which time an additional 0.5 g (3.84 mmol) of MnO$_2$ was added. The reaction was heated at reflux for 3 more days. Suspended solids were removed by filtration and the filtrate concentrated to afford 290 mg (93%) of the desired aldehyde as an oil.

MS (ES+) m/z 215 [M+H].

B.

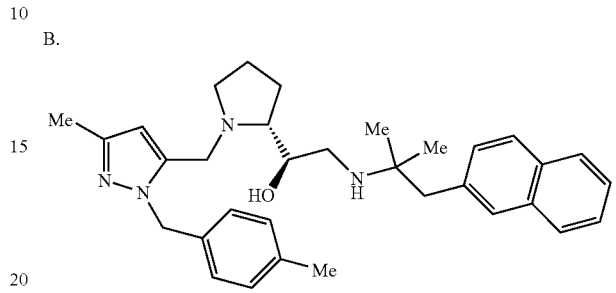

A mixture of the Example 7 Part D compound (47 mg, 0.15 mmol) and the Part A compound (32 mg, 0.15 mmol) were dissolved in methylene chloride (2 mL) containing 10 drops of glacial acetic acid. The solution was stirred at room temperature for 30 min before sodium triacetoxyborohydride (44 mg (0.21 mmol) was added. The reaction mixture was stirred at room temperature overnight before it was concentrated and purified by preparative HPLC (Method 4, gradient elution 20–100% B/A over 15 min) to provide the title compound as the bistrifluoroacetate salt (53 mg, 48%) as an oil.

MS (ES+) m/z 511 [M+H]. $^1$H NMR (500 MHz, CD$_3$OD): □ 1.39 (s,6H); 1.80–1.83 (m, 1H); 1.99–2.04 (m,1H); 2.09–2.14 (m,1H); 2.28 (s, 3H); 2.31–2.35 (m, 2H); 3.15–3.20 (m,1H); 3.20 (s,3H); 3.25–3.30 (m, 3H); 3.47–3.52 (m,1H); 3.68–3.72 (m, 1H); 4.21 (t, 1H, J=6.6 Hz); 4.41 (d, 1H, J=14.5 Hz); 4.78 (d, 1H, J=14.5 Hz); 5.43 (AB quartet, 2H, J=16.3 Hz); 6.49 (s, 1H); 6.96 (d, 2H, J=8.9 Hz); 7.12 (d, 2H, J=8.9 Hz); 7.40 (dd, 1H, J=1.7, 8.3 Hz); 7.47–7.49 (m, 2H); 7.77 (s, 1H); 7.83–7.87 (m, 3 H). HPLC retention time=2.5 min (Method A).

Examples 162 to 163 set out in Table 5 were prepared by employing the general procedure described above in Example 161.

TABLE 5

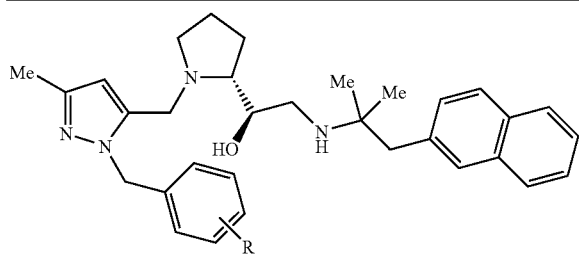

| Example No. | R | [M + H]$^+$ |
|---|---|---|
| 162 | 3-CN | 522 |
| 163 | H | 497 |

EXAMPLE 164

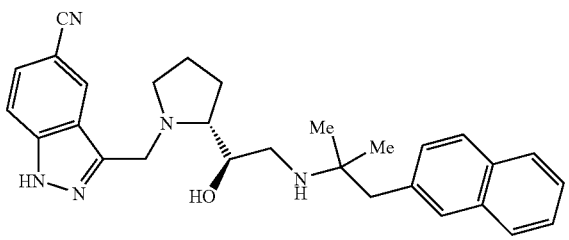

5-Cyanoindole (0.71 g, 5 mmol) and sodium nitrite (3.45 g, 50 mmol) were suspended in 100 mL distilled water with stirring. 7.5 mL of 6N hydrochloric acid was added dropwise over 15 minutes. The reaction was stirred at room temperature for a further 2 h before being extracted with EtOAc (2×15 mL). The combined organic extracts were washed with water and brine, then dried over anhydrous sodium sulfate. The mixture was filtered and the filtrate was concentrated to a semisolid. This material was passed through a silica gel plug, eluting with 5% MeOH in methylene chloride to provide partially purified 6-cyanoindazole-3-carboxaldehyde, which was used without further purification.

A mixture of 6-cyanoindazole-3-carboxaldehyde (52 mg, 0.30 mmol) and the Example 7 Part D compound (47 mg, 0.15 mmol) were dissolved in a mixture of 3 mL methylene chloride and 12 drops of glacial acetic acid at room temperature. The solution was stirred for 30 minutes before sodium triacetoxyborohydride (64 mg, 0.30 mmol) was added. The reaction was stirred at room temperature for 4 h, then concentrated to a solid which was purified by preparative HPLC (Method 4, gradient elution 20–100% B/A over 15 min) to furnish the desired product as a pink oil as the bistrifluoroacetate salt (25 mg).

MS (ES+) m/z 468 [M+H]. $^1$H NMR (500 MHz, CD$_3$OD): ☐ 1.38 (s,3H); 1.39 (s, 3H); 1.85–1.89 (m, 1H); 2.01–2.20 (m,2H); 2.36–2.40 (m,1H); 3.20 (s,2H); 3.21–3.30 (m,1H); 3.56–3.61 (m, 2H); 3.90–3.94 (m, 1H); 4.21 (t, 1H, J=6.3 Hz); 4.82 (d, 1H, J=14.4 Hz); 5.19 (d, 1H, J=14.4 Hz); 7.41 (dd, 1H, J=1.7, 7.2 Hz); 7.46–7.52 (m, 2H); 7.70 (dd, 1H, J=1.1, 10 Hz); 7.72–7.80 (m, 2H); 7.85–7.88 (m, 3H); 8.42 (s, 1H). HPLC retention time=2.0 min (Method A).

EXAMPLE 165

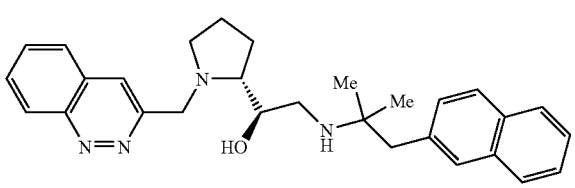

A mixture of the Example 7 Part D compound (51 mg, 0.16 mmol) and cinnoline-3-aldehyde (64 mg, 0.41 mmol) were dissolved in a mixture of 1 mL methanol and 1 mL THF at room temperature. Titanium tetraisopropoxide (116 mg, 0.41 mmol) was added and the solution was stirred at room temperature for 3 h. The pH of the reaction mixture was adjusted to pH 4 by addition of glacial acetic acid. Sodium cyanoborohydride (0.41 mmol, 410 µl of a 1.0 M solution in THF) was added. The reaction was stirred at room temperature overnight. The reaction solution was concentrated to dryness leaving a brown solid. The residue was dissolved in 15 mL 1N HCl and extracted with 3×15 mL EtOAc. The organic extracts were discarded. The pH of the aqueous layer was adjusted to 11 with solid NaOH and was extracted with 4×15 mL EtOAc. The combined organic extracts were washed with water (2×10 mL) and brine (2×10 mL), dried over MgSO$_4$ and concentrated to give an oil which was purified by preparative HPLC (Method 4, gradient elution 20–100% B/A over 15 min) to furnish 16 mg of the bistrifluoroacetate salt as an oil.

MS (ES+) m/z 455 [M+H]. $^1$H NMR (500 MHz, CD$_3$OD): ☐ 1.27 (s,3H); 1.28 (s, 3H); 1.71–1.75 (m, 1H); 1.99–2.10 (m,2H); 2.24–2.28 (m,1H); 3.08 (s,2H); 3.08–3.14 (m,1H); 3.19–3.21 (m,1H); 3.61–3.67 (m, 1H); 3.92 (d, 1H, J=15.4 Hz),4.10–4.14 (m,1H); 4.31 (d, 1H, J=15.4 Hz); 6.67 (d, 1H, J=7.2 Hz); 6.81 (t, 1H, J=8 Hz); 6.92 (d, 1H, J=7.2 Hz); 7.01 (t, 1H, J=7.2 Hz); 7.29 (d, 1H, J=6 Hz); 7.36–7.41 (m, 2H); 7.66 (s, 1H); 7.73–7.77 (m, 4H). HPLC retention time=2.2 min (Method A).

EXAMPLE 166

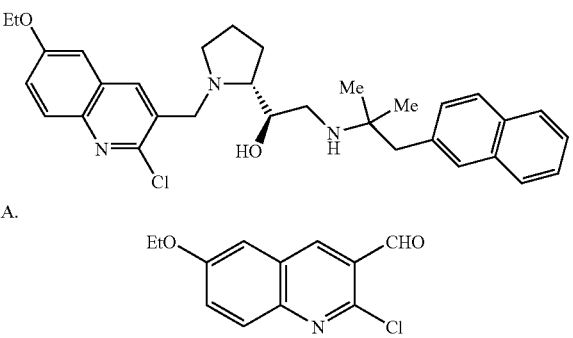

A.

To cold DMF (3.4 mL, 44 mmol) at 0° C. was added POCl$_3$ (10.3 mL, 110 mmol) dropwise through an addition funnel. The resulting clear colorless solution was warmed slowly to room temperature upon which p-acetophenetidide (3.94 g, 22 mmol) was added in one portion. The reaction turned orange immediately and was heated at 70° C. overnight. The reaction was then cooled to room temperature and was added to ice water dropwise, then the mixture was stirred for 2 h. The resulting precipitate was filtered, washed with water, EtOH, and diethyl ether, then dried over P$_2$O$_5$ in a vacuum oven at 60° C. to give the aldehyde as a yellow solid (2.54 g, 45%).

MS (ES+) m/z 236.2 [M+H]. HPLC retention time=2.73 min (Method A). $^1$H NMR (400 MHz, CDCl$_3$): ☐ 1.51 (t, J=7.0 Hz, 3H), 4.17 (qt, J=7.0, 2H), 7.18 (d, J=2.8 Hz, 1H), 7.51 (dd, J=9.2, 2.8 Hz, 1H), 7.96 (d, J=9.2 Hz, 1H), 8.62 (s, 1H), 10.48 (s, 1H).

B.

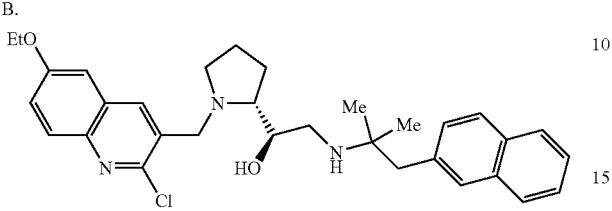

According to the procedure described in Example 7, the Part A compound (938 mg, 4.0 mmol) was reacted to provide the title compound (316 mg, 37%) as a pale yellow solid.

MS (ES+) m/z 532.3 [M+H].

Examples 167 to 174 set out in Table 6 were prepared by employing the general procedure described above in Example 166.

TABLE 6

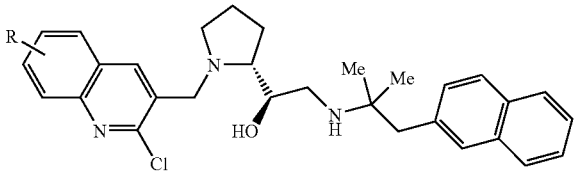

| Example No. | R | [M + H]+ |
|---|---|---|
| 167 | 6-Et | 516.3 |
| 168 | 7-OMe | 518.4 |
| 169 | 6-F | 506.3 |
| 170 | 6,7-OCH$_2$O— | 532.4 |
| 171 | 6-Br | 566.2 |
| 172 | 6-SMe | 534.2 |
| 173 | 7-Cl | 522.2 |
| 174 | 7-Me | 502.2 |

EXAMPLE 175

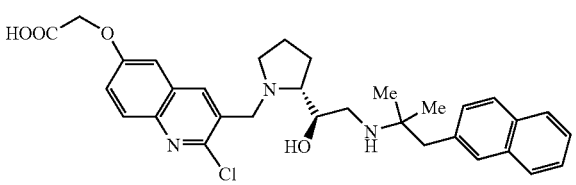

A.

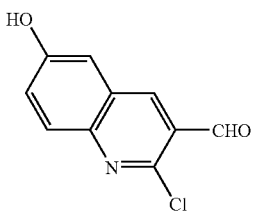

To a solution of 2-chloro-6-methoxy-3-quinolinecarboxaldehyde (510 mg, 2.3 mmol) in dry CH$_2$Cl$_2$ (100 mL) at −78° C. under argon was added BBr$_3$ (0.47 mL, 5 mmol) over 1 min. The reaction was warmed to room temperature upon which a large quantity of white precipitate formed. Ice was added to quench the reaction and the resulting orange solution was stirred at room temperature for 30 min. The reaction mixture was extracted with EtOAc (3×30 mL), dried over MgSO$_4$, filtered and concentrated. Purification by flash chromatography eluting with hexane/EtOAc (1:3) gave the phenol (269 mg, 56%) as a yellow solid.

MS (ES+) m/z 207 [M+H]. HPLC retention time=2.63 min (Method B). $^1$H NMR (400 MHz, CD$_3$OD): □ 7.15 (d, J=2.6 Hz, 1H), 7.48 (dd, J=2.6, 9.1 Hz, 1H), 7.84 (d, J=9.1 Hz, 1H), 8.60 (s, 1H), 10.42 (s, 1H).

B.

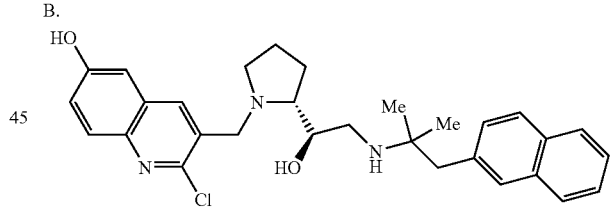

According to the procedure described in Example 7, the Part A compound (269 mg, 1.30 mmol) was reacted with the Example 7 Part D compound (162 mg, 0.52 mmol) to provide the title compound (85 mg, 13%) as a yellow solid.

MS (ES+) m/z 504.2 [M+H]. HPLC retention time=2.68 min (Method B). $^1$H NMR (400 MHz, DMSO-d6): □ 0.99 (s, 3H), 1.00 (s, 3H), 1.67–1.73 (m, 3H), 1.85–1.90 (m, 1H), 2.28 (m, 1H), 2.61 (t, J=9.4 Hz, 1H), 2.81–3.00 (m, 5H), 3.17 (s, 2H), 3.61 (brs, 1H), 3.65 (d, J=15.1 Hz, 1H), 4.25 (d,=15.1 Hz, 1H), 7.17 (d, J=2.6 Hz, 1H), 7.30 (dd, J=2.6, 9.1 Hz, 1H), 7.34 (dd, J=1.2, 8.4 Hz, 1H), 7.42–7.47 (m, 2H), 7.65 (s, 1H), 7.76–7.86 (m, 4H), 8.28 (s, 1H).

C.

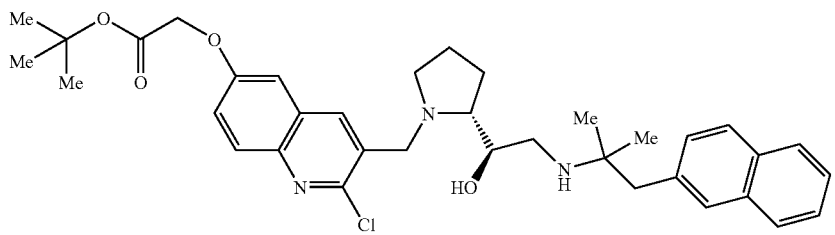

To a solution of the Part B compound (66 mg, 0.13 mmol) and t-butyl chloroacetate (18 □l, 0.13 mmol) in acetone (5 mL) was added $Cs_2CO_3$ (85 mg, 0.25 mmol). The reaction mixture was heated at 55° C. for 4 h. The reaction mixture was concentrated and partitioned between water and EtOAc. The organic layer was dried over $MgSO_4$, filtered and concentrated to yield the tert-butyl ester as a pale yellow solid (67 mg, 83%).

MS (ES+) m/z 618.3 [M+H]. HPLC retention time=3.21 min (Method B). $^1$H NMR (400 MHz, $CD_3OD$): □ 1.03 (s, 3H), 1.05 (s, 3H), 1.46 (s, 9H), 1.75–1.82 (m, 3H), 1.96–2.02 (m, 1H), 2.36–2.42 (m, 1H), 2.64 (dd, J=9.7, 11.4 Hz, 1H), 2.74–3.06 (m, 5H), 3.63–3.67 (m, 1H), 3.79 (d, J=15.4 Hz, 1H), 4.23 (d,=15.4 Hz, 1H), 4.62 (d, J=1.3 Hz, 2H), 7.17 (d, J=2.6 Hz, 1H), 7.28 (dd, J=1.3, 8.3 Hz, 1H), 7.36–7.42 (m, 3H), 7.60 (s, 1H), 7.69–7.81 (m, 4H), 8.35 (s, 1H).

D.

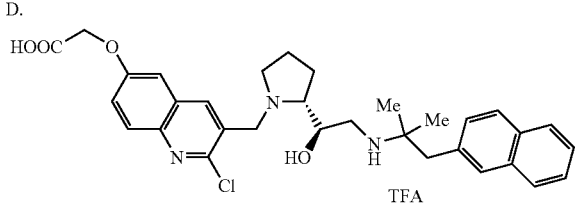

To a solution of the Part C compound (62 mg, 0.1 mmol) in dry $CH_2Cl_2$ (5 mL) was added TFA (1 mL). The reaction mixture was stirred at room temperature for 4 h, concentrated and purified by preparative HPLC (Method 1, gradient elution 40–100% B/A over 20 min) to yield the acid as a white solid (12 mg, 15%).

MS (ES+) m/z 562.2 [M+H]. HPLC retention time=2.68 min (Method B). $^1$H NMR (400 MHz, $CD_3OD$): □ 1.39 (s, 6H), 1.88–1.96 (m, 1H), 2.02–2.12 (m, 1H), 2.19–2.29 (m, 1H), 2.39–2.48 (m, 1H), 3.19 (s, 2H), 3.25 (d, J=9.2 Hz, 1H), 3.24 (d, J=2.2 Hz, 1H), 3.32–3.53 (m, 2H), 3.88 (qt,=8.7 Hz, 1H), 4.21 (t, J=9.1 Hz, 1H), 4.65 (d, J=13.6 Hz, 1H), 5.09 (d, J=13.3 Hz, 1H), 7.31 (d, J=2.5 Hz, 1H), 7.39 (d, J=8.4 Hz, 1H), 7.48–7.50 (m, 2H), 7.59 (dd, J=2.6, 9.2 Hz, 1H), 7.77 (s, 1H), 7.84–7.87 (m, 3H), 7.92 (d, J=9.2 Hz, 1H), 8.56 (s, 1H).

EXAMPLE 176

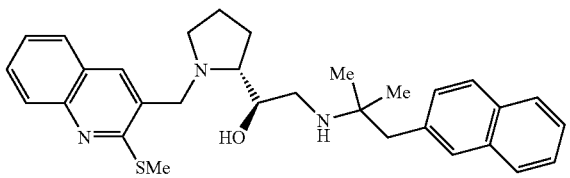

A.

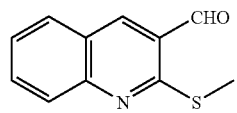

To a solution of 2-chloro-3-quinolinecarboxaldehyde (520 mg, 2.71 mmol) in MeOH (10 mL) was added sodium thiomethoxide (1.17 mL, 15% in $H_2O$, 2.71 mmol). The clear yellow solution was heated at reflux overnight. The resulting precipitate was filtered and rinsed with minimal MeOH, then dried to give the desired product as a pale yellow solid (233 mg, 42%).

MS (ES+) m/z 203 [M+H]. HPLC retention time=3.01 min (Method A). $^1$H NMR (400 MHz, $CDCl_3$): □ 2.73 (s, 3H), 7.51 (dt, J=8.4, 1.3 Hz, 1H), 7.80 (dt, J=8.4, 1.3 Hz, 1H), 7.87 (dd, J=1.3, 0.9 Hz, 1H), 7.99 (d, J=8.4 Hz, 1H), 8.47 (s, 1H), 10.33 (s, 1H).

B.

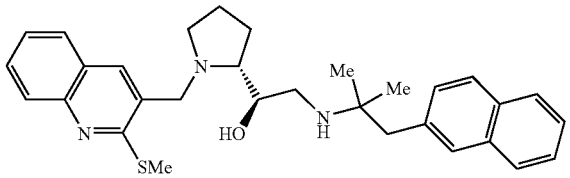

According to the procedure described in Example 7, the Part A compound (43.5 mg, 0.139 mmol) was reacted to provide the title compound (30 mg, 43%) as a white foam.

MS (ES+) m/z 500.4 [M+H].

EXAMPLE 177

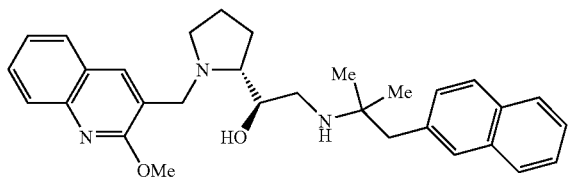

According to the procedure described for the Example 176 compound, 2-chloro-3-quinolinecarboxaldehyde was reacted with NaOMe, followed by reductive amination to provide the title compound as a white foam.

HPLC retention time=2.49 min (Method A). MS (ES+) m/z 484.5 [M+H].

EXAMPLE 178

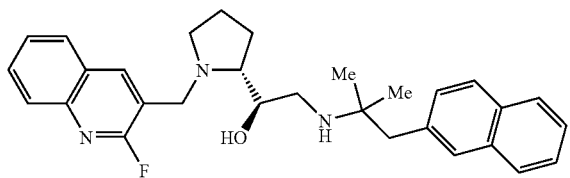

According to the procedure described for the Example 176 compound, 2-chloro-3-quinolinecarboxaldehyde was reacted with KF and tetramethylammonium chloride, followed by reductive amination to provide the title compound as a white solid.

MS (ES+) m/z 472.4 [M+H].

EXAMPLE 179

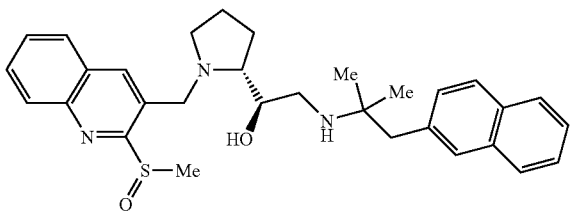

A.

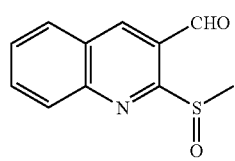

To a solution of the Example 176 Part A compound (225 mg, 1.11 mmol) in CH$_2$Cl$_2$ at 0° C. was added mCPBA (383 mg, 2.22 mmol) in one portion, upon which a white precipitate formed. After one hour, Na$_2$S$_2$O$_3$ (15 mL) and saturated NaHCO$_3$ (5 mL) were added. The mixture was extracted with CH$_2$Cl$_2$ (30 mL), washed with brine, dried, concentrated and purified by flashed chromatography on silica gel eluting with 1% MeOH/CH$_2$Cl$_2$ to give a pale yellow solid (187 mg, 77%).

HPLC retention time=1.43 min (Method A). MS (ES+) m/z 220.3 [M+H]. $^1$H NMR (400 MHz, CDCl$_3$): □ 2.83 (s, 3H), 7.63 (t, J=7.9, Hz, 1H), 7.84 (t, J=8.4 Hz, 1H), 7.96 (d, J=7.9 Hz, 1H), 8.23 (d, J=8.4 Hz, 1H), 8.72 (s, 1H), 10.26 (s, 1H).

B.

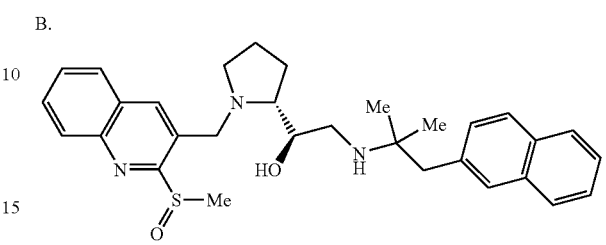

According to the procedure described in Example 7, the Part A compound (79.6 mg, 0.362 mmol) was reacted to provide the title compound (22 mg, 29%) as a yellow foam.

MS (ES+) m/z 516.4 [M+H].

EXAMPLE 180

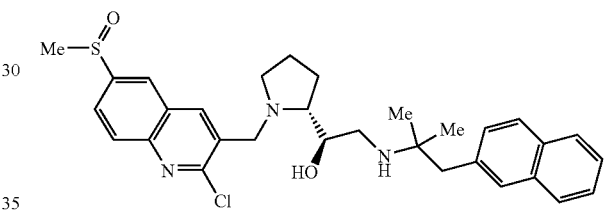

A.

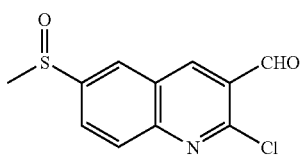

According to the procedure described for the Example 179 Part A compound, 2-chloro-6-methylthio-3-quinolinecarboxaldehyde (201 mg, 0.85 mmol) was oxidized to provide a mixture of the title compound (135 mg, 59%) and the sulfone A2 (78 mg, 36%) both as white solids.

A2

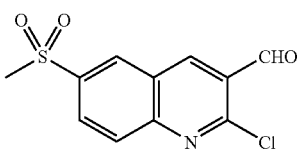

B.

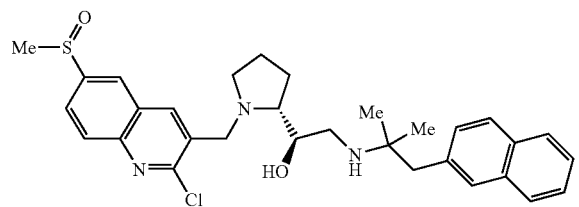

According to the procedure described in Example 7, the Part A compound (78 mg, 0.31 mmol) was reacted to provide the title compound (23 mg, 35%) as a yellow foam.

HPLC retention time=2.51 min (Method B). MS (ES+) m/z 550.3 [M+H].

EXAMPLE 181

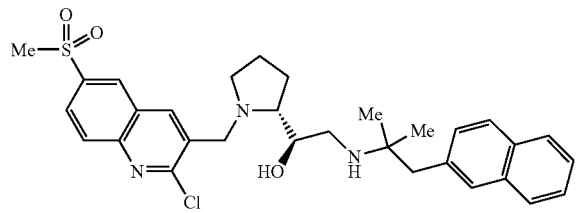

According to the procedure described in Example 7, the Example 180 Part A2 compound (135 mg, 0.50 mmol) was reacted to provide the title compound (42 mg, 37%) as a white solid.

HPLC retention time=2.58 min (Method B). MS (ES+) m/z 566.3 [M+H].

EXAMPLE 182

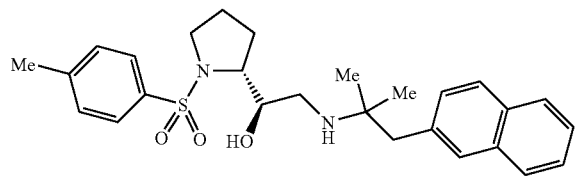

To a clear, colorless solution of the Example 7 Part D compound (44 mg, 0.14 mmol) in dichloromethane (0.5 mL) was added pyridine (14 μL, 0.17 mmol) and p-toluenesulfonyl chloride (30 mg, 0.16 mmol). After several minutes, a white solid precipitated from the clear, slightly yellow solution. In order to push the reaction to completion, p-toluenesulfonyl chloride (32 mg, 0.17 mmol) and triethylamine (18 μL, 0.17 mmol) were added. After 4 h, the reaction was diluted with dichloromethane and washed with saturated NaHCO$_3$, water, and brine, dried over MgSO$_4$, then filtered and concentrated to give a clear, yellow oil. Flash chromatography on silica gel (5% MeOH in dichloromethane to 10% MeOH in dichloromethane) gave the title compound (24.5 mg, 37%) as a clear, yellow oil.

MS (ES+) m/z 467 [M+H]. HRMS m/z Calc'd for C$_{27}$H$_{35}$N$_2$O$_3$S (M+H): 467.2368. Found 467.2351. $^1$H NMR (400 MHz, CDCl$_3$): □ 1.19 (s, 3H); 1.21 (s, 3H); 1.25–1.37 (m, 1H); 1.46–1.57 (m, 1H); 1.72–1.81 (m, 2H); 2.43 (s, 3H), 2.85 (dd, J=11.4, 7.9 Hz, 1H); 2.99–3.04 (m, 3H), 3.31–3.43 (m, 2H); 3.79–3.88 (m, 2H); 7.30 (d, J=8.4 Hz, 2H); 7.35 (dd, J=8.4, 1.3 Hz, 1H); 7.42–7.48 (m, 2H); 7.68 (s, 1H); 7.72 (d, J=8.4 Hz, 2H); 7.77 (d, J=8.4 Hz, 1H); 7.79–7.83 (m, 2H). HPLC retention time=6.20 min (Method C). [□]$_D$:+71.98 (c=6.6, MeOH)

Examples 183 to 188 set out in Table 7 were prepared by employing the general procedure described above in Example 182.

TABLE 7

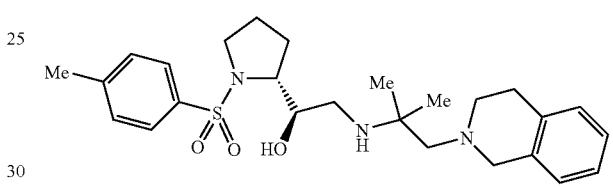

| Example No. | R | [M + H]$^+$ |
|---|---|---|
| 183 | 2-CN | 478.3 |
| 184 | 4-CN | 478.3 |
| 185 | 4-OMe | 483.4 |
| 186 | 3-CN | 478.3 |
| 187 | H | 453.3 |
| 188 | 3-NO$_2$ | 498.3 |

EXAMPLE 189

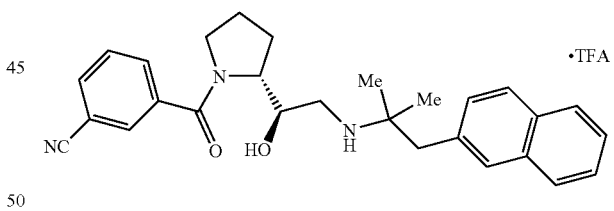

According to the procedure for Example 182, the Example 218 Part D compound was reacted with toluenesulfonyl chloride to provide the title compound (32 mg, 47%) as a white foam.

MS (ES+) m/z 472.4 [M+H].

EXAMPLE 190

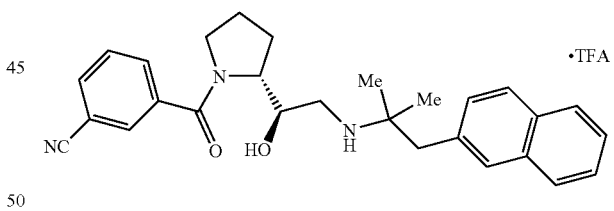

To a cooled (0° C.), clear, colorless solution of the Example 7 Part D (50 mg, 0.16 mmol) in chloroform (0.98 mL) was added triethylamine (22 μL, 0.16 mmol) and m-cyanobenzoyl chloride (24.7 mg, 0.16 mmol). After 1 h, the reaction was diluted with dichloromethane and washed with saturated NaHCO$_3$, water, and brine, dried over MgSO$_4$, then filtered and concentrated to give 46 mg of a clear, slightly yellow oil. Purification by preparative HPLC (Method 4, gradient elution 20–100% B/A over 15 min) gave the title compound (21.9 mg, 25%) as a clear, colorless oil.

MS (ES+) m/z 442.4 [M+H]. $^1$H NMR (400 MHz, CD$_3$OD): □ 1.37 (s, 3H); 1.40 (s, 3H); 1.73–1.86 (m, 1H); 2.00–2.10 (m, 2H), 2.14–2.26 (m, 1H); 3.17–3.25 (m, 4H); 3.40–3.48 (m, 1H); 3.56–3.65 (m, 1H); 4.10–4.16 (m, 1H); 4.43–4.50 (m, 1H); 7.36–7.43 (m, 1H); 7.46–7.52 (m, 2H);

7.62–7.69 (m, 1H); 7.77 (s, 1H); 7.82–7.91 (m, 6H). HPLC retention time=5.46 min (Method C). [□]$_D$:+70.32 (c=4.2, CH$_2$Cl$_2$)

Examples 191 to 197 set out in Table 8 were prepared by employing the general procedure described above in Example 190.

TABLE 8

| Example No. | R | [M + H]$^+$ |
|---|---|---|
| 191 | 3-O$_2$N-C$_6$H$_4$-CH$_2$- | 462.4 |
| 192 | C$_6$H$_5$-CH$_2$- | 431 |
| 193 | 4-Me-C$_6$H$_4$-CH$_2$- | 445 |
| 194 | 3,5-F$_2$-C$_6$H$_3$-CH$_2$- | 467 |
| 195 | 3,4-Cl$_2$-C$_6$H$_3$-CH$_2$- | 465 |
| 196 | 2,6-F$_2$-C$_6$H$_3$-CH$_2$- | 467 |
| 197 | 2-OH-3-NO$_2$-C$_6$H$_3$- | 478.2 |

EXAMPLE 198

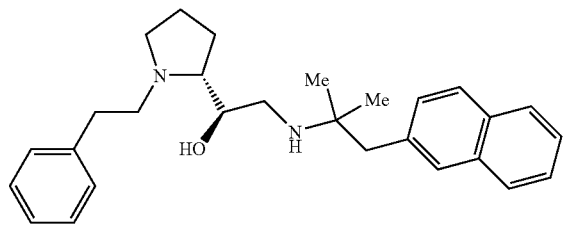

To a mixture of 2-phenylethanol (31 mg, 0.26 mmol) and the Example 7 Part D comopund (40 mg, 0.18 mmol) in propionitrile (4 mL) was added (cyanomethyl)trimethylphosphonium iodide (62 mg, 0.26 mmol) and diisopropylethylamine (29 mg, 0.26 mmol) [see Zaragosa, F., and Stephensen, H., *J. Org. Chem.* 2001, 67, 2518]. The reaction was heated to 90° C. overnight. The mixture was cooled to room temperature, concentrated, and purified by preparative HPLC (Method 4, gradient elution 20–100% B/A over 15 min) to provide the title compound as a trifluoroacetate salt (41 mg, 43%) as a pale yellow oil.

MS (ES+) m/z 417 [M+H]. $^1$H NMR (500 MHz, CD$_3$OD): □ 1.28 (s,3H); 1.29 (s, 3H); 1.75 (ddd, 1H, J=6.6, 9.5, 9.9 Hz); 1.98 (ddd,1H, J=6.2, 13.2, 13.2 Hz); 2.07 (ddd,1H, J=6.6, 13,2, 13.2 Hz); 2.22 (ddd,1H, J=6.6, 14.2, 15.4 Hz); 3.00 (ddd,2H, J=6.0, 11.0, 12.5 Hz); 3.10–3.17 (m, 3H); 3.21–3.20 (m,4H); 3.57–3.66 (m,2H); 3.70–3.77 (m, 1H); 4.06 (ddd, 1H, J=2.2, 9.0, 10.0 Hz); 7.12–7.26 (m,5H); 7.30 (dd, 1H, J=1,2, 8.2 Hz); 7.35–7.39 (m,2H); 7.68 (s,1H); 7.73–7.76 (m,3H).

HPLC retention time=2.2 min (Method A).

Examples 199 to 205 set out in Table 9 were prepared by employing the general procedure described above in Example 198.

TABLE 9

| Example No. | R | [M + H]$^+$ |
|---|---|---|
| 199 | 4-OMe | 447 |
| 200 | 4-Cl | 452 |
| 201 | 3-NO$_2$ | 462 |
| 202 | 4-CN | 442 |
| 203 | 2-OMe | 447 |
| 204 | 2-Me | 431 |
| 205 | 2,6-diCl | 486 |

EXAMPLE 206

A.

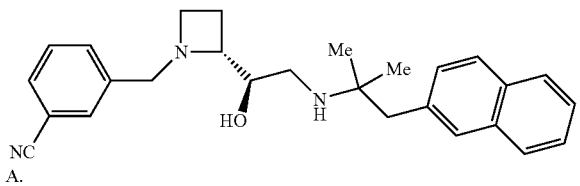

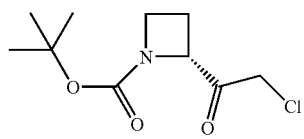

According to the procedure described for the preparation of the Example 7 Part A compound, (R)-N-Boc-azetidinecarboxylic acid (250 mg, 1.24 mmol) was transformed to the chloromethyl ketone (228 mg, 79% yield).

B.

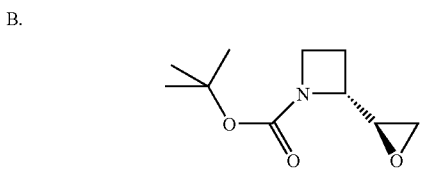

According to the procedure described in for the preparation of the Example 7 Part B1 compound, the Part A compound (210 mg, 0.90 mmol) was reacted with L-Selectride to provide the epoxide as a oil (41 mg, 23%) as the major diastereomer.

$^1$H NMR (400 MHz, CDCl$_3$): □ 1.45 (s, 9H); 2.12–2.2 (m, 2H); 2.25–3.35 (m, 1H); 2.76 (broad s, 1H); 2.82 (t, 1H, J=4.84 Hz); 3.13 (q, 1H, J=6.96 and 3.2 Hz); 3.72–3.78 (m, 1H,); 3.78–3.8 (m, 1H); 4.38 (broad s,1H).

C.

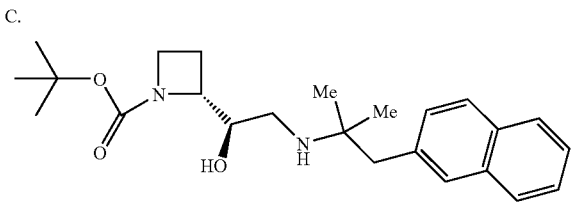

According to the procedure described for the preparation of the Example 1 Part C compound, the Part B compound (41 mg, 0.206 mmol) prepared as above was reacted with 1,1-dimethyl-2-(2-naphthyl)ethylamine (41 mg, 0.206 mmol) to provide the title compound (74 mg, 90%) as a colorless oil.

$^1$H NMR (400 MHz, CDCl$_3$): □ 1.14 (s, 3H); 1.15 (s, 3H); 1.43 (s, 9H); 2.1–2.2 (m, 2H); 2.75–2.85(m, 2H); 2.94 (q, 2H); 3.78–3.86 (m, 2H); 3.95 (broad s, 1H); 4.32–4.36 (m, 1H); 7.36 (d, 1H); 7.35–7.45 (m, 2H); 7.66 (s, 1H); 7.75 (d, 1H); 7.75–7.85 (m, 2H). $^{13}$C NMR (400 MHz, CDCl$_3$): □ 18.59; 26.06; 28.28; 29.73; 43.80; 46.73; 42.24; 54.74; 65.13; 73.25; 80.38; 125.3; 125.8; 127.3; 127.45; 127.56; 128.94; 129.12; 132.09; 132.26; 135.28; MS (ES+) m/z 399.2 [M+H]. HPLC retention time=6.16 min (Method C).

D.

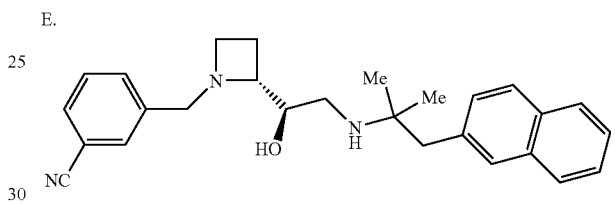

The Part C compound (68 mg, 0.17 mmol) was dissolved in TFA/CH$_2$Cl$_2$ (1:1, 1 mL). The reaction mixture was stirred for 3 h at room temperature, then concentrated to dryness. The residue was dissolved in EtOAc (2 mL), washed with saturated NaHCO$_3$ solution (2×1 mL), dried over MgSO$_4$ and evaporated. The crude compound was purified by preparative HPLC (Method 1, gradient elution 0–100% B/A over 20 min), then free-based to provide the title compound (12 mg, 24%) as a colorless oil.

E.

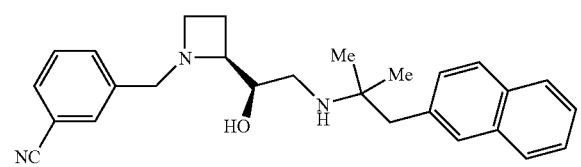

According to the reductive amination procedure described in Example 7, the Part D compound (12 mg, 0.04 mmol) was alkylated to provide the title compound (5.5 mg, 33% yield) as a white lyophilate.

$^1$H NMR (500 MHz, CD$_3$OD): □ 1.34 (s, 6H); 2.44 (m, 1H); 2.6 (m, 1H); 2.85 (t, 1H, J=8 Hz); 3.12 (m, 1H); 3.96 (m, 1H); 4.11 (m, 1H); 4.33 (t, 1H); 4.46 (d, 1H, J=8 Hz); 4.53 (m, 1H); 4.63 (d, 1H, J=8 Hz); 7.38 (q, 1H); 7.47–7.54 (m, 2H); 7.68 (t, 1H, J=4.8 Hz); 7.76 (s, 1H); 7.82–7.9 (m, 5H); 7.93 (s, 1H). MS (ES+) m/z 414.2 [M+H]. HPLC retention time=4.09 min (Method C).

EXAMPLE 207

A.

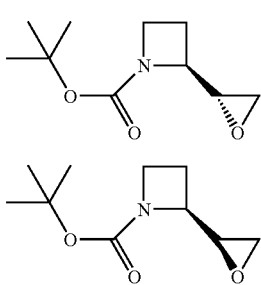

According to the procedure described in Example 206, (S)-N-Boc-azetidinecarboxylic acid was transformed into a diastereomeric mixture of the epoxides A1 and A2.

Compound A1:

$^1$H NMR (500 MHz, CDCl$_3$): ☐ 1.35 (s, 9H); 2.05 (m, 1H); 2.22 (m, 1H); 2.65 (broad s, 1H); 2.72 (t, 1H, J=5 Hz); 3.03 (m, 1H); 3.64 (m, 1H); 3.75 (m, 1H); 4.28 (broad s, 1H).

Compound A2:

$^1$H NMR (500 MHz, CDCl$_3$): ☐ 1.33 (s, 9H); 1.95 (m, 1H); 2.04 (m, 1H); 2.46 (broad s, 1H); 2.74 (t, 1H, J=5 Hz); 3.19 (broad s, 1H); 3.70–3.72 (m, 2H); 4.06 (broad s, 1H).

B.

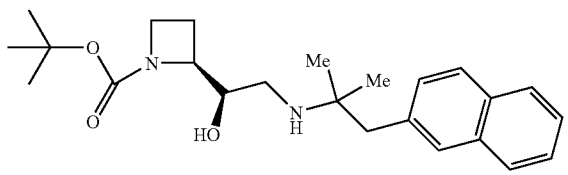

According to the procedure in Example 206, the Part A2 compound was reacted to provide the title compound (26%) as a white lyophilate.

$^1$H NMR (500 MHz, CDCl$_3$): ☐ 1.09 (s, 3H); 1.10 (s, 3H); 1.44 (s, 9H); 2.07 (m, 1H); 2.17 (m, 1H);2.76(m, 1H); 2.77 (q, 1H); 2.87 (q, 1H) 3.78 (m, 1H); 3.85 (m, 2H); 4.32–4.35 (m, 1H); 7.34 (d, 1H, J=5 Hz); 7.4–7.46 (m, 2H); 7.65 (s, 1H; 7.75 (d, 1H, J=5 Hz); 7.79 (m, 2H). $^{13}$C NMR (500 MHz, CDCl$_3$): ☐ 18.65; 26.45; 26.56; 28.25; 43.67; 46.97; 53.80; 65.35; 74.09; 80.35; 125.18; 125.71; 127.17; 127.41; 127.52; 128.78; 129.18; 131.98; 133.22; 135.77. MS (ES+) m/z 399.0 [M+H]. HPLC retention time=6.13 min (Method C).

C.

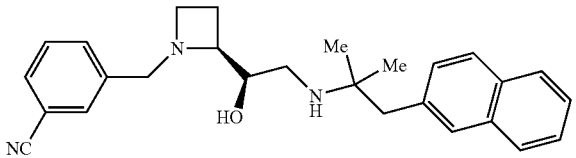

According to the procedure in Example 206, the Part B compound was hydrolyzed and alkylated in two steps to provide the title compound (11%) as a white lyophilate.

$^1$H NMR (400 MHz, CD$_3$OD): ☐ 1.33 (s, 6H); 2.4–2.5 (m, 1H); 2.56–2.66 (m, 1H); 2.84 (q, 1H, J=10.2 Hz); 3.09–3.12 (m, 4H); 3.92–4.0 (m, 1H); 4.11 (m, 1H); 4.34 (t, 1H, J=7.52 Hz); 4.46 (d, 1H, J=13.2); 4.55 (m, 1H); 4.63 (d, 1H, J=13.2); 7.4 (d, 1H); 7.49 (m, 2H); 7.7 (t, 1H); 7.75 (s, 1H); 7.87 (m, 5H); 7.93 (s, 1H). $^{13}$C NMR (400 MHz, CD$_3$OD): ☐ 20.11; 23.36; 44; 45; 53; 54; 59; 62; 69; 72; 110.48; 127.25; 127.49; 128.65; 129.22; 129.67; 130.73; 131.65; 132.6; 133.4; 134; 134.84; 135.5; 136.38; 160. MS (ES+) m/z 414.2 [M+H]. HPLC retention time=4.06 min (Method C).

EXAMPLE 208

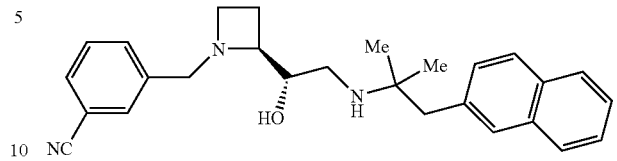

According to the procedure for the preparation of the Example 207 compound, the Example 207 Part A1 compound was reacted to give the title compound as a white lyophilate.

$^1$H NMR (400 MHz, CD$_3$OD): ☐ 1.33 (s, 6H); 2.46 (m, 1H); 2.72 (m, 1H); 2.90 (t, 1H); 3.13–3.16 (m, 4H); 4.0–4.15 (m, 2H); 4.5 (m, 2H); 4.75 (m, 1H); 7.36 (q, 1H, J=8.4 and 1.5 Hz); 7.46–7.52 (m, 2H); 7.66 (t, 1H, J=7.9 Hz); 7.75 (s, 1H); 7.84–7.86 (m, SH); 7.94 (s, 1H). MS (ES+) m/z 414.2 [M+H]. HPLC retention time=3.91 min (Method C).

EXAMPLE 209

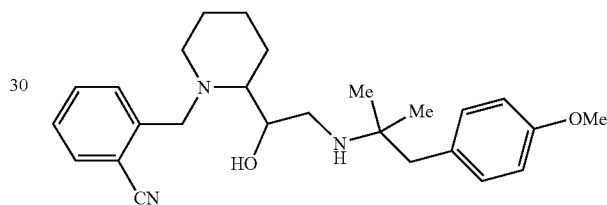

A.

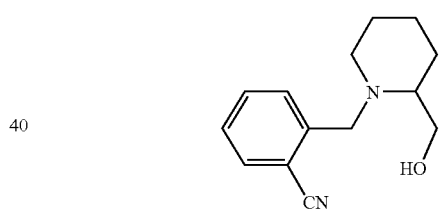

To a solution of 2-piperidinemethanol (1.15 g, 10 mmol) and 2-cyanobenzyl bromide (1.96 g, 10 mmol) in DMF (10 mL) was added potassium carbonate (4.15 g, 30 mmol) at 80° C. under argon. Stirring was continued at 80° C. for 48 h. The reaction mixture was allowed to cool to room temperature and water was added. Extraction with ethyl acetate and concentration of the organic layer provided the title compound (2.17 g, 94%) as an oil.

MS (ES+) m/z 231 [M+H]. HPLC retention time: 0.60 min (Method A).

B.

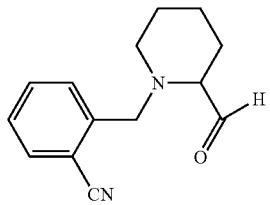

To a stirred solution of DMSO (606 μL, 8.5 mmol) and oxalyl chloride (373 μL, 4.3 mmol) in methylene chloride (24 mL) at −78° C. under argon was added a solution of the Part A compound (0.89 g, 3.88 mmol) in methylene chloride (4 mL). After 25 min of stirring, triethylamine (2.7 mL, 19.4 mmol) was added and the cooling bath was removed. After an additional 30 min of stirring, the reaction mixture was poured into ether. The layers were separated after addition of water. The organic layer was extracted with ether, washed with water, dried over MgSO₄, and concentrated to afford the product as an oil (815 mg, 92%).

MS (ES+) m/z 229 [M+H]. HPLC retention time: 1.04 min (Method A).

C.

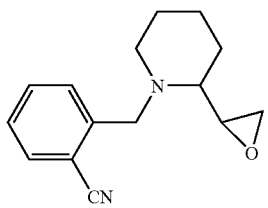

To a stirred suspension of 60 wt % sodium hydride in mineral oil (496 mg, 12.4 mmol) in 10 mL DMSO under argon at ambient temperature was added trimethylsulfonium iodide (3.0 g, 13.6 mmol). After 15 min of stirring, the Part B aldehyde (457 mg, 2 mmol) was added dropwise as a solution in 3 mL DMSO. After 3 h of stirring, water and ethyl acetate were added. Extraction of the organic layer was followed by washing with water, drying over MgSO₄, and concentration of the organic layer to provide the crude product (460 mg, 100%).

MS (ES+) m/z 243 [M+H]. HPLC retention time: 0.96 min (Method A).

D.

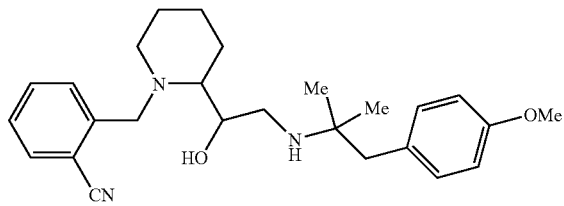

A solution of 2-(4-methoxyphenyl)-1,1-dimethyl-ethylamine (30 mg, 0.17 mmol) and the Part C epoxide (120 mg, 0.5 mmol) in 1 mL ethanol was heated under argon in a pressure tube at 110° C. for 72 h. The reaction mixture was concentrated and purified by preparative HPLC (Method 3, gradient elution 40–100% B/A over 15 min) to afford the desired product (6 mg, 8%) as a TFA salt.

MS (ES+) m/z 422 [M+H]. ¹H NMR (500 MHz, CD₃OD): δ 1.35 (s,6H); 1.20–2.10 (m, 6H); 2.90–3.60 (m,8H); 3.79 (s,3H); 4.40–5.10 (m,2H); 6.91 (d,2H); 7.20 (d,2H); 7.60–7.95 (m,4H). HPLC retention time.=1.45 min (Method A).

EXAMPLE 210

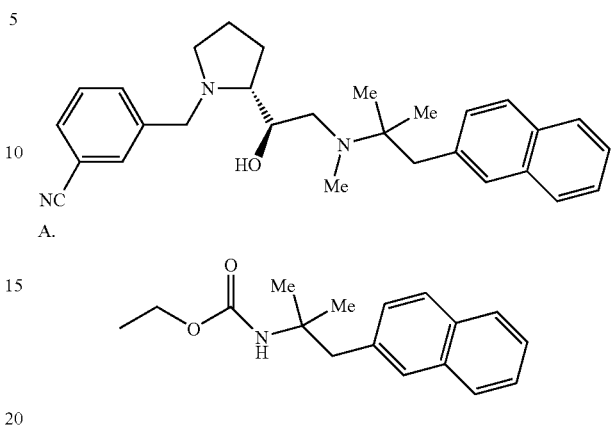

A.

To a solution of 1,1-dimethyl-2-(2-naphthyl)ethylamine (100 mg, 0.5 mmol) and ethyl chloroformate (57 μl, 0.6 mmol) in CH₂Cl₂ (5 mL) was added a solution of K₂CO₃ (350 mg, 2.5 mmol) in H₂O (5 mL). The reaction mixture was stirred vigorously at room temperature for 15 min. The layers were separated and the aqueous layer was washed with CH₂Cl₂ (2×10 mL), dried over MgSO₄, filtered and concentrated to yield a pale yellow oil (179 mg, 100%).

HPLC retention time=3.44 min (Method A). ¹H NMR (400 MHz, CDCl₃): δ 1.28 (t, J=7.0 Hz, 3H); 1.34 (s, 6H); 3.15 (s, 2H); 4.14 (dd, J=7.0, 14 Hz, 2H); 4.44 (s, 1H); 7.30 (dd, J=6.1, 7.5 Hz, 1H); 7.45 (m, 2H); 7.59 (s, 1H); 7.75–7.83 (m, 3H). ¹³C NMR (100.40 MHz, CDCl₃): δ 14.76, 27.53, 53.25, 125.38, 125.87, 127.33, 128.96, 129.07, 133.29, 135.54.

B.

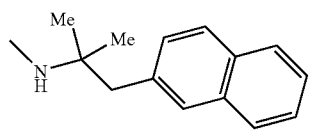

To a solution of LAH (0.6 mL, 1M in THF) at 0° C. under argon was added a solution of the Part A compound (134 mg, 0.52 mmol) in THF (5 mL) portionwise over 3 min. The reaction became clear and colorless. The ice bath was removed and the reaction was stirred at room temperature for 1 h then refluxed at 64° C. for 14 hr. The reaction mixture was cooled to 0° C., then water (5 mL) and 1N NaOH (5 mL) were added sequentially. The resulting mixture was stirred at room temperature to give a white precipitate which was filtered and rinsed with THF. The filtrate was condensed and acidified with 10% HCl to pH ~2, then washed with CH₂Cl₂ (3×10 mL). The aqueous layer was treated with aqueous 10% NaOH to pH ~10, extracted with CH₂Cl₂ (3×10 mL), dried over MgSO₄, and condensed to yield a yellow oil (23 mg, 21%).

HPLC retention time=2.07 min (Method A).

$^1$H NMR (400 MHz, CDCl$_3$): □ 1.10 (s, 6H); 2.43 (s, 3H) 2.86 (s, 2H); 7.30 (dd, J=1.7, 8.4 Hz, 1H); 7.45 (m, 2H); 7.61 (s, 1H); 7.78 (m, 3H).

C.

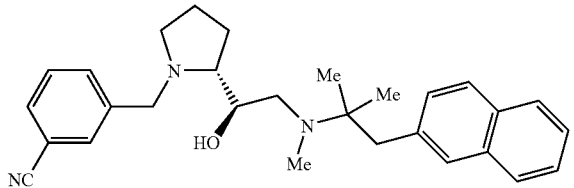

A mixture of the Part B compound (20 mg, 0.09 mmol) and the Example 3 Part D1 compound (17 mg, 0.07 mmol) was heated at 90° C. in a one dram vial under argon overnight. The reaction mixture was cooled to room temperature and purified by silica gel flash chromatography eluting with 5–10% MeOH in CH$_2$Cl$_2$ to give the title compound as a yellow gum (10 mg, 33%).

MS (ES+) m/z 441 [M+H]. HPLC retention time=2.55 min (Method E). $^1$H NMR (400 MHz, CD$_3$OD): □ 1.10 (d, J=8.7 Hz, 6H); 1.63–1.69 (m, 3H); 1.82–1.95 (m, 1H); 2.22 (m, 1H); 2.48 (s, 3H); 2.58 (m, 1H); 2.68 (m, 2H); 2.80–3.01 (m, 3H); 3.42 (d, J=13.7 Hz, 1H); 3.63 (m, 1H); 4.24 (d, 1H); 7.34–7.80 (m, 11H). $^{13}$C NMR (400 MHz, CD$_3$OD): □ 24.98, 25.19, 28.24, 36.47, 44.85, 55.20, 56.12, 61.17, 68.81, 72.86, 113.60, 120.27, 126.79, 127.31, 128.61, 128.91, 128.96, 130.58, 130.75, 132.07, 133.88, 134.01, 135.08, 135.20, 143.51.

EXAMPLES 211 TO 217

Examples 211 to 217 set out in Table 10 were prepared by employing the general procedure described in Examples 4 and 5.

TABLE 10

| Example No. | R | Q | [M + H]$^+$ |
|---|---|---|---|
| 211 | 2-CN | benzothiophen-2-yl | 434 |
| 212 | 3-CN | benzothiophen-2-yl | 434 |
| 213 | 2-CN | indol-2-yl | 417 |

TABLE 10-continued

| Example No. | R | Q | [M + H]$^+$ |
|---|---|---|---|
| 214 | 3-CN | indol-2-yl | 417 |
| 215 | 2-CN | 2-MeO-phenyl | 408 |
| 216 | 3-CN | 2-MeO-phenyl | 408 |
| 217 | 3-CN | 6-MeO-naphthalen-2-yl | 458 |

EXAMPLE 218

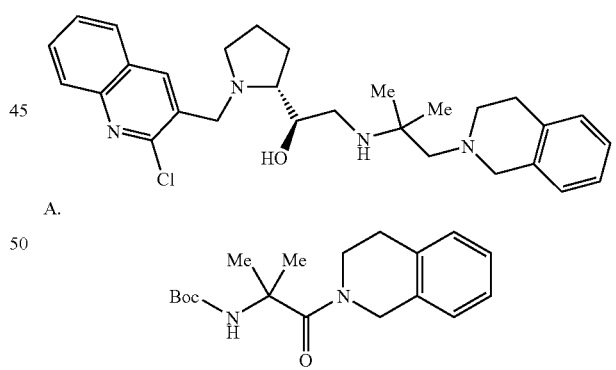

A.

To a solution of Boc-□-methylalanine (609 mg, 3 mmol) and tetrahydroisoquinoline (400 mg, 3 mmol) in CH$_2$Cl$_2$ (25 mL) was added 1-hydroxy-7-azabenzotriazole (408 mg, 3 mmol) and 1-(3-dimethylaminopropyl)-3-ethylcarbodiimide hydrochloride (575 mg, 3 mmol). The resulting brownish solution was stirred at room temperature overnight. The reaction was concentrated and purified by silica gel flash chromatography eluting with 50% ethyl acetate in hexane to give the crude product as a white foam (548 mg, 57%).

MS (ES+) m/z 341.3 [M+Na]. HPLC retention time=2.93 min (Method A). $^1$H NMR (400 MHz, CDCl$_3$): (mixture of rotamers) major: ☐ 1.31 (s, 9H), 1.54 (s, 6H), 2.88 (t, J=5.5 Hz, 2H), 3.93 (s, 2H), 4.84 (s, 2H), 7.12–7.18 (m, 4H).

B.

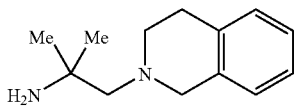

To a solution of the Part A compound (1.19 g, 3.74 mmol) in THF (15 mL) at 0° C. was added borane-methyl sulfide complex (1.5 mL, 15 mmol). The reaction mixture was refluxed for 3 h before it was cooled to 0° C. and MeOH (2 mL) was added. The mixture was stirred at room temperature for 1 hr. Hydrochloric acid (4 mL, 2N in ether) was added and the reaction mixture was refluxed for 1.5 hrs. After being cooled down to room temperature, more MeOH was added. After concentration, NaOH (10 mL, 10 N) was added and the mixture was extracted with EtOAc (3×35 mL). The combined EtOAc layers were washed with brine, dried over $MgSO_4$, and concentrated to give a light yellow foam (583 mg, 76%).

MS (ES+) m/z 493.4 [M+H]. $^1$H NMR (400 MHz, $CDCl_3$): ☐ 1.11 (s, 6H), 2.39 (s, 2H), 2.88 (s, 4H), 3.79 (s, 2H), 6.98–7.12 (m, 4H).

C.

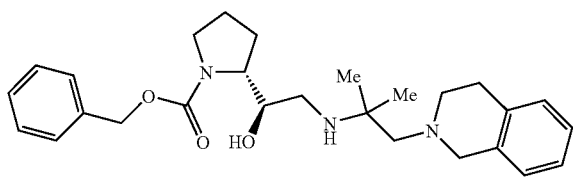

A mixture of the Example 7 Part B1 compound (368 mg, 1.49 mmol) and the Part B compound (304 mg, 1.49 mmol) was heated at 85° C. in a pressure tube under argon overnight. The reaction mixture was cooled to room temperature and purified by silica gel flash chromatography, eluting with 10% methanol in dichloromethane to give the product as a white foam (317 mg, 47%).

HPLC retention time=2.75 min (Method A). MS (ES+) m/z 452.4 [M+H]. $^1$H NMR (400 MHz, $CDCl_3$): ☐ 1.05 (s, 6H), 1.94 (m, 4H), 2.42–2.70 (m, 4H), 2.87 (s, 4H), 3.33 (m, 1H), 3.60 (m, 1H), 3.76 (m, 2H), 3.95 (m, 1H), 5.13 (s, 2H), 6.99 (m, 1H), 7.09 (m, 3H), 7.35 (m, 5H).

D.

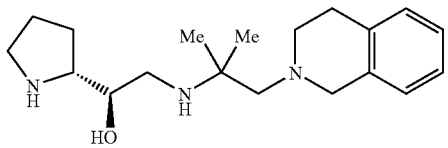

A mixture of the Part C compound (270 mg, 0.6 mmol) and 10% palladium on carbon (27 mg) in MeOH (4 mL) was maintained under an atmosphere of hydrogen overnight. The catalyst was filtered and the filtrate was concentrated to give a slight yellowish oil (190 mg, 100%).

HPLC retention time=0.373 min (Method A). MS (ES+) m/z 318.4 [M+H]. $^1$H NMR (400 MHz, $CD_3OD$): ☐ 1.12 (s, 3H), 1.13 (s, 3H), 1.58–1.93 (m, 4H), 2.52–2.74 (m, 4H), 2.87 (brs, 5H), 2.89–3.22 (m, 1H), 3.58–3.81 (m, 4H), 6.97–7.08 (m, 4H).

E.

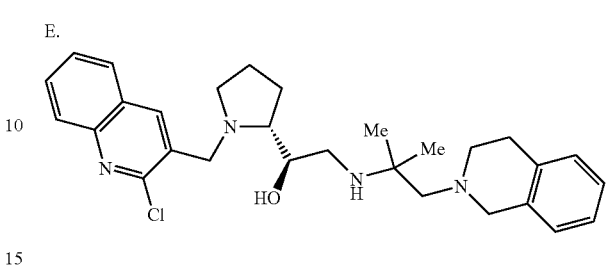

According to the procedure described in Example 7, reductive amination of 2-chloro-3-quinolinecarboxaldehyde and the Part D compound (18.9 mg, 0.06 mmol) provided the title compound as a off-white solid which was purified by preparative HPLC (Method 2, gradient elution 0–100% B/A over 20 min) to give the title compound (14.6 mg, 29%) as a white foam.

HPLC retention time=1.78 min (Method A). MS (ES+) m/z 483.4 [M+H].

Examples 219 to 225 set out in Table 11 were prepared by employing the general procedure described in Example 218.

TABLE 11

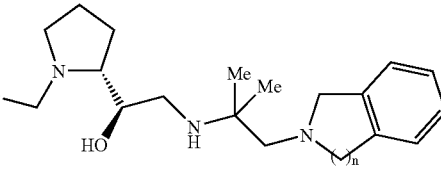

| Example No. | Ar$^1$ | n | [M + H]$^+$ |
|---|---|---|---|
| 219 | 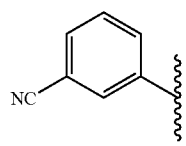 | 2 | 433.5 |
| 220 | 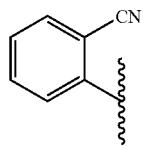 | 2 | 433.5 |
| 221 | 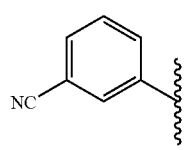 | 1 | 419.4 |
| 222 | 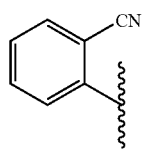 | 1 | 419.4 |

TABLE 11-continued

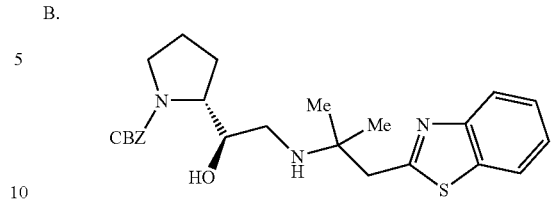

| Example No. | Ar¹ | n | [M + H]⁺ |
|---|---|---|---|
| 223 | ![furan-CH2-S-phenyl with O2N] | 2 | 565.4 |
| 224 | ![F, OH phenyl] | 2 | 442.4 |
| 225 | ![OEt quinoline with Cl] | 2 | 537.3 |

EXAMPLE 226

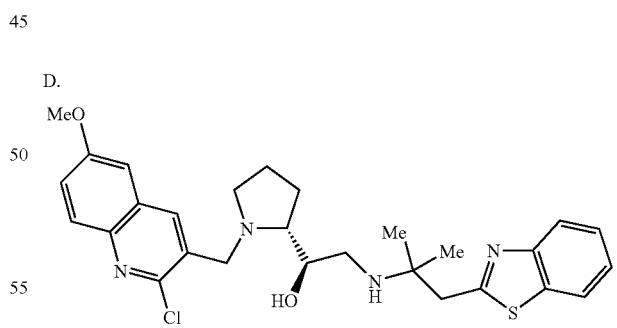

A.

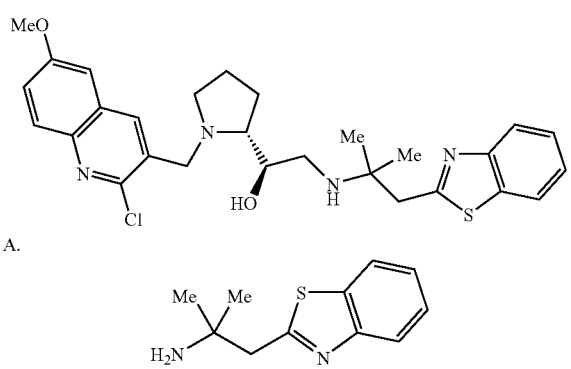

The Part A compound was prepared following the literature procedure (Liebigs. Ann. Chem., 1976, 336–347).

B.

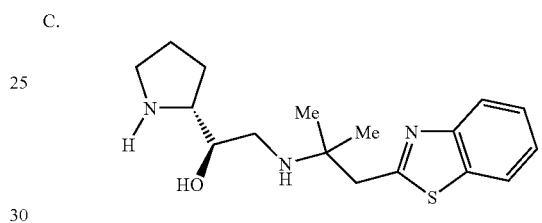

According to the procedure described for the Example 218 Part C compound, coupling of the Part A compound (348 mg, 1.69 mmol) with the Example 7 Part B1 compound (417 mg, 1.69 mmol) provided the title compound as a colorless oil (560 mg, 75%).

HPLC retention time=2.70 min (Method A). MS (ES+) m/z 454.3 [M+H].

C.

To a solution of the Part B compound (525 mg, 1.16 mmol) in CH$_2$Cl$_2$ (10 mL) at room temperature was added HBr in acetic acid (2.1 mL, 10.4 mmol). After 4 h, the reaction mixture was poured into H$_2$O (30 mL) and washed with CH$_2$Cl$_2$ (3×20 mL). The aqueous layer was basified with aqueous NaOH (1N, 25 mL) upon which a white precipitate formed. The mixture was extracted with CH$_2$Cl$_2$ (3×20 mL), and the organic layers were combined and dried over MgSO$_4$, then concentrated to give a colorless oil (286 mg, 77%).

HPLC retention time=1.02 min (Method A).

D.

According to the procedure described for the Example 218 Part E compound, reductive amination of 2-chloro-6-methoxy-3-quinolinecarboxaldehyde (248 mg, 1.12 mmol) and the Part C compound (143 mg, 0.45 mmol) provided the title compound as a white foam (160 mg, 68%).

HPLC retention time=2.11 min (Method A). MS (ES+) m/z 525.4 [M+H].

EXAMPLE 227

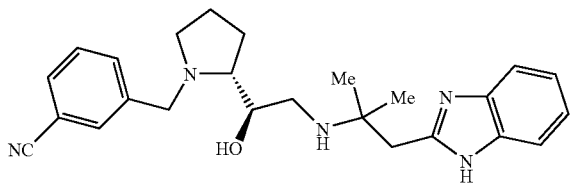

The title compound was prepared in 16% yield according to the procedure described in Example 228.

HPLC retention time=1.41 min (Method A). MS (ES+) m/z 418.4 [M+H].

EXAMPLE 228

A.

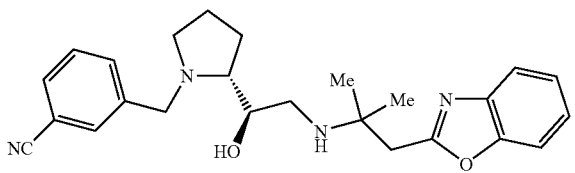

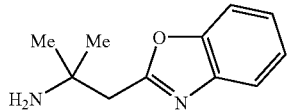

To a solution of 2-methoxy-4,4-dimethylazetine (225 mg, 2 mmol) in absolute EtOH (2 mL) was added aminophenol (327 mg, 3 mmol) followed by toluenesulfonic acid (38 mg, 0.2 mmol). The dark red solution was stirred at room temperature overnight. EtOH was removed and the residue was redissolved in $CHCl_3$ (50 mL), washed with NaOH (2×15 mL, 1N), brine (15 mL), dried and concentrated to give a brownish solid (254 mg, 67%).

HPLC retention time=1.16 min (Method A). MS(ES+) m/z 191.3 [M+H]. $^1$H NMR (400 MHz, $CD_3OD$): □ 1.25 (s, 6H), 3.05 (s, 2H), 7.34–7.37 (m, 2H), 7.57–7.59 (s, 1H), 7.65–7.67 (m, 1H).

B.

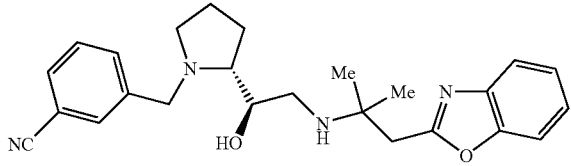

According to the procedure described in Example 3, coupling of the Part A compound (14.4 mg, 0.08 mmol) and the Example 3 Part D1 compound (17.3 mg, 0.08 mmol) provided the title compound as a white foam (17.7 mg, 37%).

MS(ES+) m/z 419.4 [M+H]. HPLC retention time=1.43 min (Method A).

EXAMPLE 229

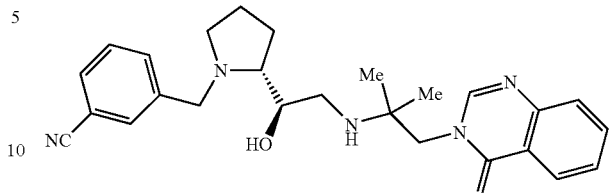

A.

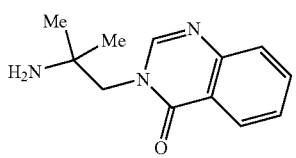

A mixture of 2-aminobenzoic acid (1 g, 7.29 mmol) and triethylorthoformate (3 mL) was refluxed overnight. The reaction mixture was cooled to room temperature and triturated with 10 mL of hexane. The resulting solid was filtered and further washed with hexane to yield 1.1 g of the expected benzo[d][1,3]oxazin-4-one.

A mixture of the above solid, 1,2-diamino-2-methyl propane (1.6 mL, 15.2 mmol) and toluene (10 mL) was refluxed overnight. Volatiles were evaporated and the residue was dissolved in 15 mL of $CH_2Cl_2$. The solution was washed with water, dried over $MgSO_4$ and concentrated to dryness. Purification was performed by flash chromatography on silica gel, eluting first with 5% MeOH/$CH_2Cl_2$ solution and then with 10% MeOH/1% $NH_4OH$/$CH_2Cl_2$ solution to give the desired compound as a colorless oil.

B.

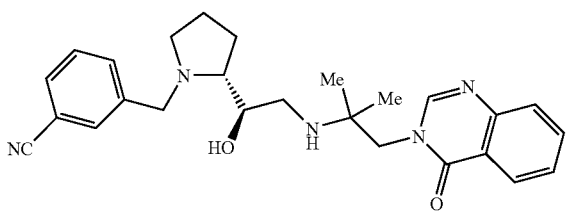

A mixture of the Example 3 Part D1 compound (21 mg, 0.09 mmol) and the Part A compound (25 mg, 0.09 mmol) was heated to 90° C. overnight. The reaction mixture was cooled to room temperature, then purified by preparative HPLC (Method 1, gradient elution 0–100% B/A over 20 min) to yield the expected compound.

MS (ES+) m/z 446.4 [M+H]. $^1$H NMR (400 MHz, $CD_3OD$): □ 1.50 (s, 6H); 2.04–2.18 (m, 2H); 2.18–2.29 (m, 1H); 2.38–2.5 (m, 1H); 3.21(q, 1H, J=9.68 and 12.4 Hz); 3.34–3.47 (m, 3H); 3.59 (q, 1H, J=9.68 and 2.68 Hz); 3.72–3.78 (m,1H) 4.2(d, 1H, J=15.60 Hz); 4.22–4.28 (m, 1H); 4.38 (d, 1H, J=12.9 Hz); 4.56 (d, 1H, J=15.6 Hz); 4.92 (d, 1H, J=12.9 Hz); 7.60 (t, 1H, J=7.52 Hz); 7.69 (t, 1H, J=7.52 Hz); 7.75 (d, 1H, J=8.08 Hz); 7.85–7.93 (m, 4H). 7.97 (s, 1H); 8.27 (d, 1H, J=6.96 Hz); 8.32 (s, 1H). HPLC retention time=2.46 min (Method C).

Examples 230 to 231 set out in Table 12 were prepared by employing the general procedure described above in Example 229.

TABLE 12

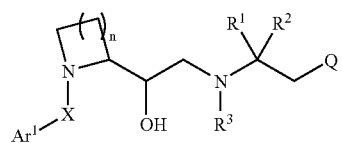

| Example No. | X | [M + H]+ |
|---|---|---|
| 230 | H | 446 |
| 231 | OMe | 506 |

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound of the formula I wherein:
Ar$^1$ is a substituted or unsubstituted heteroaryl, wherein heteroaryl contains one nitrogen and five carbons and may optionally be part of a bicyclic ring system;
X is a linking group selected from the group consisting of alkylene, CO, alkyleneCO, OCO, alkyleneOCO, SO$_2$ and alkyleneSO$_2$;
n is an integer from 1 to 4;
R$^1$ and R$^2$ are each independently substituted or unsubstituted C$_1$–C$_4$ alkyl, or R$^1$ can be cyclized with R$^2$ to form (—CH$_2$—)$_m$ where m is an integer from 2 to 5;
R$^3$ is hydrogen(H) or alkyl;
Q is substituted or unsubstituted aryl, excluding heteroaryl;
including all prodrug esters, pharmaceutically acceptable salts or stereoisomers thereof.

2. The compound as defined in claim 1 wherein:
X is alkylene
n is an integer from 1 to 3;
R$^3$ is hydrogen(H) or methyl; and
Q is selected from substituted or unsubstituted phenyl, or substituted or unsubstituted naphthyl;
including all prodrug esters, pharmaceutically acceptable salts or stereoisomers thereof.

3. The compound as defined in claim 1 wherein:
X is alkylene;
n is 2;
R$^1$ and R$^2$ are methyl, or R$^1$ can be cyclized with R$^2$ to form a cyclopropyl ring;
R$^3$ is hydrogen; and
Q is substituted or unsubstituted phenyl or substituted or unsubstituted naphthyl.

4. The compound as defined in claim 1 wherein:
X is alkylene;
n is 2;
R$^1$ and R$^2$ are methyl, or R$^1$ can be cyclized with R$^2$ to form a cyclopropyl ring; and
R$^3$ is hydrogen.

5. The compound as defined in claim 1 wherein the compound is selected from:

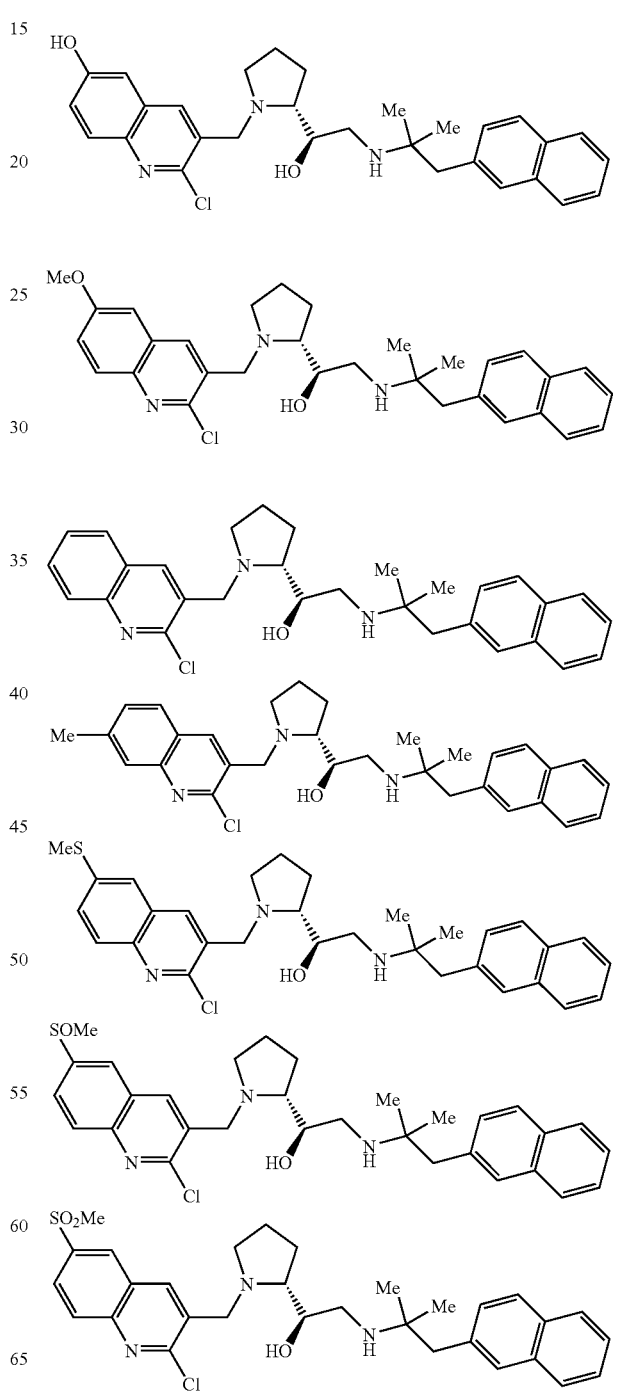

-continued
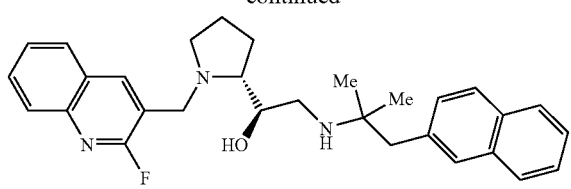
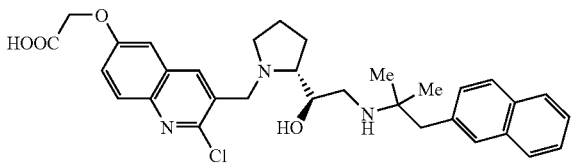
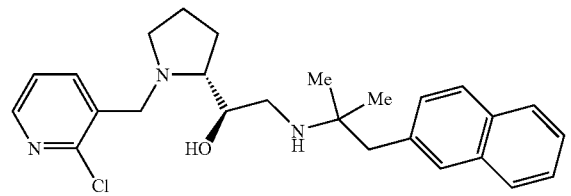
and
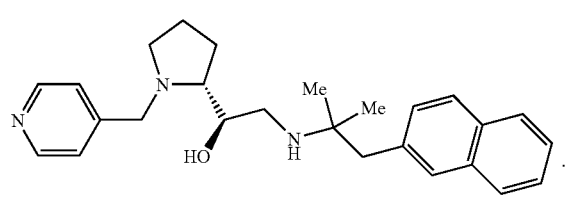
6. The compound as defined in claim 1 wherein the compound is selected from:
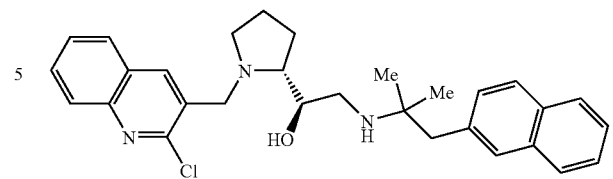
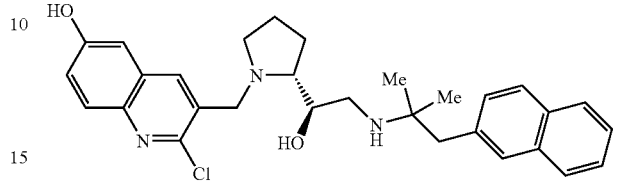
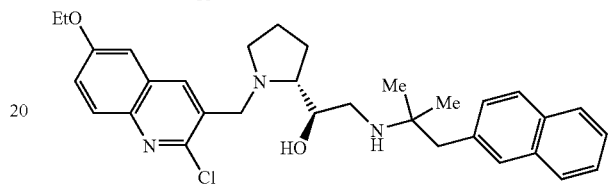
and
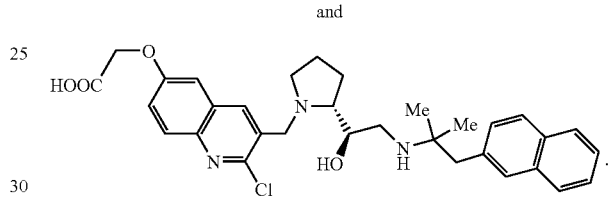
7. A pharmaceutical composition comprising a compound as defined in claim 1 and a pharmaceutically acceptable carrier therefor.
* * * * *